United States Patent
Finlay et al.

(10) Patent No.: US 9,242,966 B2
(45) Date of Patent: Jan. 26, 2016

(54) PHTHALAZINES AS POTASSIUM ION CHANNEL INHIBITORS

(71) Applicant: BRISTOL-MYERS SQUIBB COMPANY, Princeton, NJ (US)

(72) Inventors: Heather Finlay, Skillman, NJ (US); Ashok Kumar Adisechan, Pondicherry (IN); Prashantha Gunaga, Bangalore (IN); John Lloyd, Yardley, PA (US); Pothukanuri Srinivasu, Bangalore (IN)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/200,063

(22) Filed: Mar. 7, 2014

(65) Prior Publication Data
US 2014/0303168 A1    Oct. 9, 2014

Related U.S. Application Data

(60) Provisional application No. 61/775,748, filed on Mar. 11, 2013.

(51) Int. Cl.
| | |
|---|---|
| C07D 405/14 | (2006.01) |
| C07D 401/14 | (2006.01) |
| C07D 401/04 | (2006.01) |
| C07D 401/12 | (2006.01) |
| C07D 403/04 | (2006.01) |
| A61K 31/502 | (2006.01) |
| A61K 31/506 | (2006.01) |

(52) U.S. Cl.
CPC ............ *C07D 405/14* (2013.01); *A61K 31/502* (2013.01); *A61K 31/506* (2013.01); *C07D 401/04* (2013.01); *C07D 401/12* (2013.01); *C07D 401/14* (2013.01); *C07D 403/04* (2013.01)

(58) Field of Classification Search
CPC .. C07D 405/14; C07D 401/14; C07D 401/04; A61K 30/502; A61K 31/506
USPC .......................................... 514/248; 544/237
See application file for complete search history.

(56) References Cited

U.S. PATENT DOCUMENTS

| | | | |
|---|---|---|---|
| 6,331,543 | B1 | 12/2001 | Garvey et al. |
| 8,575,184 | B2 | 11/2013 | Johnson et al. |
| 2005/0277772 | A1 | 12/2005 | Carreira |
| 2012/0232068 | A1 | 9/2012 | Johnson et al. |
| 2014/0031345 | A1 | 1/2014 | Johnson et al. |

FOREIGN PATENT DOCUMENTS

| | | |
|---|---|---|
| EP | 1 326 134 A1 | 7/2003 |
| EP | 1 454 908 A1 | 9/2004 |
| EP | 1 454 910 A1 | 9/2004 |
| WO | WO 2005/030130 | 4/2005 |
| WO | WO 2005/121157 | 12/2005 |
| WO | WO 2006/097441 | 9/2006 |
| WO | WO 2006/127329 | 11/2006 |
| WO | WO 2011/028741 | 3/2011 |
| WO | WO 2012/075393 | 6/2012 |
| WO | WO 2013/083741 | 6/2013 |

OTHER PUBLICATIONS

Eguchi, Y. et al., "Studies on Antiatherosclerotic Agents. Synthesis and Inhibitory Activities on Platelet Aggregation of 4-Aryl Derivatives of 7-Ethoxycarbonyl-6,8-dimethyl-1(2H)-phthalazinone", Chem. Pharm. Bull., vol. 39, No. 8, pp. 2009-2015 (1991).
Yassin, F.A. et al., "Synthesis of 4,5,6,7-Tetraphenyl-8-(substituted)-3(2H)-phthalazinone Derivatives Likely to Possess Antihypertensive Activity", Bull. Korean Chem. Soc., vol. 11, No. 1, pp. 7-10 (1990).
Yassin, F.A. et al., "Synthesis of 4,5,6,7-Tetraphenyl-8-(substituted)-3-(2H)-Phthalazinone Derivatives Likely to Possess Antihypertensive Activity", Egypt. J. Chem., vol. 33, No. 2, pp. 199-208 (1991).
Yassin, F.A. et al., "Synthesis of 4,5,6,7-Tetraphenyl-8-substituted-3(2H)-Phthalazinone Derivatives with Potential Antihypertensive Activity", Revue Roumaine de Chimie, vol. 36, Nos. 1-3, pp. 201-208 (1991).
Finlay et al., U.S. Appl. No. 14/200,055, filed Mar. 7, 2013.
Finlay et al., U.S. Appl. No. 61/775,735, filed Mar. 11, 2013.
Finlay et al., U.S. Appl. No. 61/775,742, filed Mar. 11, 2013.
Finlay et al., U.S. Appl. No. 61/775,750, filed Mar. 11, 2013.

*Primary Examiner* — Paul V Ward
(74) *Attorney, Agent, or Firm* — Mary K. VanAtten

(57) ABSTRACT

A compound of formula (I)

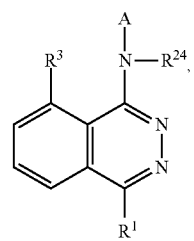

(I)

wherein A, $R^1$, $R^3$, and $R^{24}$ are described herein. The compounds are useful as inhibitors of potassium channel function and in the treatment and prevention of arrhythmia, $I_{Kur}$-associated disorders, and other disorders mediated by ion channel function.

17 Claims, No Drawings

PHTHALAZINES AS POTASSIUM ION CHANNEL INHIBITORS

CROSS-REFERENCE TO RELATED APPLICATIONS

This application claims the benefit of U.S. Provisional Application No. 61/775,748 filed Mar. 11, 2013, whose contents are hereby incorporated by reference.

FIELD OF THE INVENTION

The present invention provides for phthalazines useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such compounds in the treatment and prevention of arrhythmia, $I_{Kur}$-associated disorders, and other disorders mediated by ion channel function.

BACKGROUND OF THE INVENTION

The ultra-rapidly activating delayed rectifier $K^+$ current ($I_{Kur}$) is believed to represent the native counterpart to a cloned potassium channel designated $K_v1.5$ and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves' ophthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (PROGRAF®) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of $K_v1.3$, for example, are immunosuppressive. See Wulff et al., "Potassium channels as therapeutic targets for autoimmune disorders", *Curr. Opin. Drug Discov. Devel.*, 6(5):640-647 (September 2003); Shah et al., "Immunosuppressive effects of a $K_v1.3$ inhibitor", *Cell Immunol.*, 221(2):100-106 (February 2003); Hanson et al., "UK-78,282, a novel piperidine compound that potently blocks the $K_v1.3$ voltage-gated potassium channel and inhibits human T cell activation", *Br. J. Pharmacol.*, 126(8):1707-1716 (April 1999).

Inhibitors of $K_v1.5$ and other $K_v1.x$ channels stimulate gastrointestinal motility. Thus, the compounds of the invention are believed to be useful in treating motility disorders such as reflux esophagitis. See Frey et al., "Blocking of cloned and native delayed rectifier K channels from visceral smooth muscles by phencyclidine", *Neurogastroenterol. Motil.*, 12(6):509-516 (December 2000); Hatton et al., "Functional and molecular expression of a voltage-dependent K(+) channel ($K_v1.1$) in interstitial cells of Cajal", *J. Physiol.*, 533(Pt 2):315-327 (Jun. 1, 2001); Vianna-Jorge et al., "Shaker-type $K_v1$ channel blockers increase the peristaltic activity of guinea-pig ileum by stimulating acetylcholine and tachykinins release by the enteric nervous system", *Br. J. Pharmacol.*, 138(1):57-62 (January 2003); Koh et al., "Contribution of delayed rectifier potassium currents to the electrical activity of murine colonic smooth muscle", *J. Physiol.*, 515(Pt. 2):475-487 (Mar. 1, 1999).

Inhibitors of $K_v1.5$ relax pulmonary artery smooth muscle. Thus, the compounds of the invention are believed to be useful in treating hypertension and otherwise improving vascular health. See Davies et al., "$K_v$ channel subunit expression in rat pulmonary arteries", *Lung*, 179(3):147-161 (2001), Epub. Feb. 4, 2002; Pozeg et al., "In vivo gene transfer of the O2-sensitive potassium channel $K_v1.5$ reduces pulmonary hypertension and restores hypoxic pulmonary vasoconstriction in chronically hypoxic rats", *Circulation*, 107(15):2037-2044 (Apr. 22, 2003), Epub. Apr. 14, 2003.

Inhibitors of $K_v1.3$ increase insulin sensitivity. Hence, the compounds of the invention are believed to be useful in treating diabetes. See Xu et al., "The voltage-gated potassium channel $K_v1.3$ regulates peripheral insulin sensitivity", *Proc. Natl. Acad. Sci. USA*, 101(9):3112-3117 (Mar. 2, 2004), Epub. Feb. 23, 2004; MacDonald et al., "Members of the $K_v1$ and $K_v2$ voltage-dependent K(+) channel families regulate insulin secretion", *Mol. Endocrinol.*, 15(8):1423-1435 (August 2001); MacDonald et al., "Voltage-dependent K(+)

channels in pancreatic beta cells: role, regulation and potential as therapeutic targets", *Diabetologia*, 46(8):1046-1062 (August 2003), Epub. Jun. 27, 2003.

Stimulation of $K_v1.1$ is believed to reduce seizure activity by hyperpolarizing neurons. Thus, the compounds of the invention are believed to be useful in treating seizures, including seizures associated with epilepsy and other neurological diseases. See Rho et al., "Developmental seizure susceptibility of kv1.1 potassium channel knockout mice", *Dev. Neurosci.*, 21(3-5):320-327 (November 1999); Coleman et al., "Subunit composition of $K_v1$ channels in human CNS", *J. Neurochem.*, 73(2):849-858 (August 1999); Lopantsev et al., "Hyperexcitability of CA3 pyramidal cells in mice lacking the potassium channel subunit $K_v1.1$", *Epilepsia*, 44(12): 1506-1512 (December 2003); Wickenden, "Potassium channels as anti-epileptic drug targets", *Neuropharmacology*, 43(7):1055-1060 (December 2002).

Inhibition of $K_v1.x$ channels improves cognition in animal models. Thus, the compounds of the invention are believed to be useful in improving cognition and/or treating cognitive disorders. See Cochran et al., "Regionally selective alterations in local cerebral glucose utilization evoked by charybdotoxin, a blocker of central voltage-activated $K^+$-channels", *Eur. J. Neurosci.*, 14(9):1455-1463 (November 2001); Kourrich et al., "Kaliotoxin, a $K_v1.1$ and $K_v1.3$ channel blocker, improves associative learning in rats", *Behav. Brain Res.*, 120(1):35-46 (Apr. 8, 2001).

SUMMARY OF THE INVENTION

In accordance with the present invention, acyclic compounds and related compounds are provided that have the general structure of formula (I):

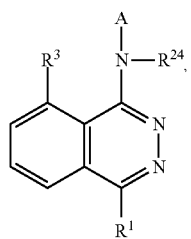

(I)

wherein A, $R^1$, $R^3$, and $R^{24}$ are defined below.

By use of a respective effective amount of at least one compound described herein, provided are methods of treating (including ameliorating), reducing the risk of or preventing arrhythmias, atrial fibrillation, atrial flutter, supraventricular arrhythmias, gastrointestinal disorders (such as reflux esophagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as apixaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Another aspect of this invention is directed to methods of treating, inhibiting, or ameliorating the symptoms of a disease or disorder that is modulated or otherwise affected by inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels), comprising administering to a subject in need thereof a therapeutically effective amount of a compound of the present invention or an individual isomer or mixture of isomers or a pharmaceutically acceptable salt thereof.

Another aspect of this invention is directed to methods of treating, inhibiting, or ameliorating arrhythmia, or maintaining normal sinus rhythm, comprising administering to a subject in need thereof a therapeutically effective amount of a compound of the present invention or an individual isomer or mixture of isomers or a pharmaceutically acceptable salt thereof.

Another aspect of this invention is directed to methods of controlling heart rate, comprising administering to a subject in need thereof a therapeutically effective amount of a compound of the present invention or an individual isomer or mixture of isomers or a pharmaceutically acceptable salt thereof.

Definitions

The terms "alk" or "alkyl" refer to straight or branched chain hydrocarbon groups having 1 to 12 carbon atoms, or 1 to 8 carbon atoms, 1 to 6 carbon atoms, 1 to 4 carbon atoms, or 1 to 3 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The term "haloalkyl" is intended to include both branched and straight-chain saturated aliphatic hydrocarbon groups, for example $CF_3$, having the specified number of carbon atoms, substituted with 1 or more halogen, up to and including perhalo alkyls (where all hydrogen atoms are replaced with a halogen).

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

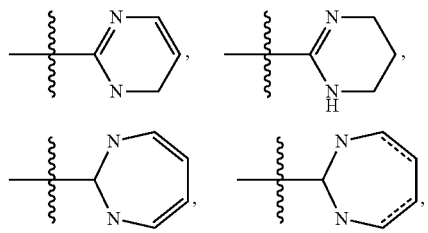

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl]), or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

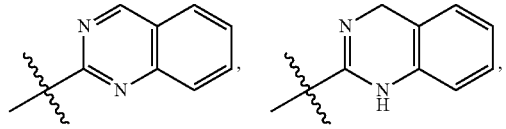

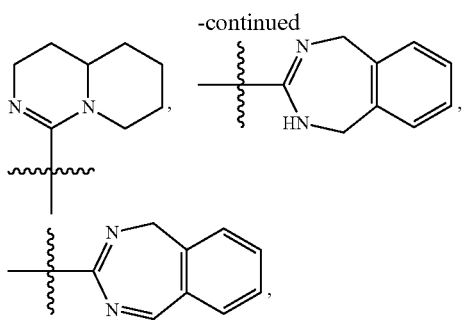

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e., —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

Compounds described herein may form salts or solvates which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. In one embodiment, the salts are pharmaceutically acceptable (i.e., non-toxic, physiologically acceptable), although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

The present invention is intended to cover the compounds in their neutral state, salts of those compounds, or mixtures of the compounds in their neutral state with one or more salt forms, or mixtures of salt forms.

The compounds described herein which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds described herein which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Any compound that can be converted in vivo to provide the bioactive agent (i.e., the compound of formula (I)) is a prodrug within the scope and spirit of the invention.

The term "prodrugs" as employed herein includes esters and carbonates formed by reacting one or more hydroxyls of compounds of formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, H. Bundgaard, ed., Elsevier (1985);

c) Bundgaard, H., Chapter 5, "Design and Application of Prodrugs", Krosgaard-Larsen, P. et al., eds., *A Textbook of Drug Design and Development, pp.* 113-191, Harwood Academic Publishers (1991); and d) Testa, B. et al., *Hydrolysis in Drug and Prodrug Metabolism*, Wiley-VCH (2003).

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds may be prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H or D and $^3$H or T, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H or D, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

To the extent that compounds described herein, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms are contemplated within the scope of this invention. Individual stereoisomers of the compounds of the invention may, for example, be substantially free of other isomers, or may be admixed, for example, as racemates or with all other, or other selected, stereoisomers.

"Stable compound" and "stable structure" are meant to indicate a compound that is sufficiently robust to survive isolation to a useful degree of purity from a reaction mixture, and formulation into an efficacious therapeutic agent. The present invention is intended to cover stable compounds.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

When any variable (e.g., $R^{13}$) occurs more than one time in any constituent or formula for a compound, its definition at each occurrence is independent of its definition at every other occurrence. Thus, for example, if a group is shown to be substituted with 0-2 $R^{13}$, then said group may optionally be substituted with up to two $R^{13}$ groups and $R^{13}$ at each occurrence is selected independently from the definition of $R^{13}$. Also, combinations of substituents and/or variables are permissible only if such combinations result in stable compounds.

"Treating" or "treatment" as used herein covers the treatment, prophylaxis, and/or reducing the risk, of a disease or disorder described herein, or treatment, prophylaxis, or reducing the risk of a symptom of a disease or disorder, in a subject, such as a human, and includes:

i. inhibiting a disease or disorder, i.e., arresting its development; or ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

The terms "including", "such as", "for example" and the like are intended to refer to exemplary embodiments and not to limit the scope of the present invention.

DETAILED DESCRIPTION OF THE INVENTION

In accordance with the present invention, compounds of formula (I) are provided

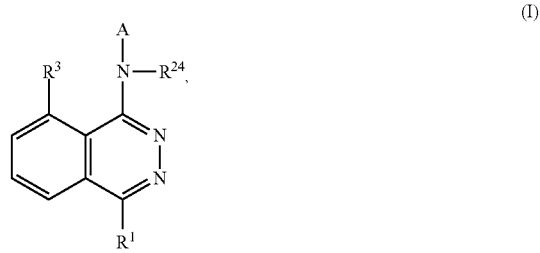

or enantiomers, diastereomers, tautomers, prodrugs or salts thereof, wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

R$^1$ is C$_{1-10}$ alkyl substituted with 1-2 —OH, haloC$_{1-10}$ alkyl, C$_{2-12}$ alkenyl, or C$_{3-10}$ cycloalkyl, wherein the cycloalkyl may be substituted with 0-2 R$^{13}$; or R$^1$ is

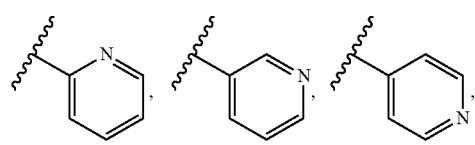

-continued

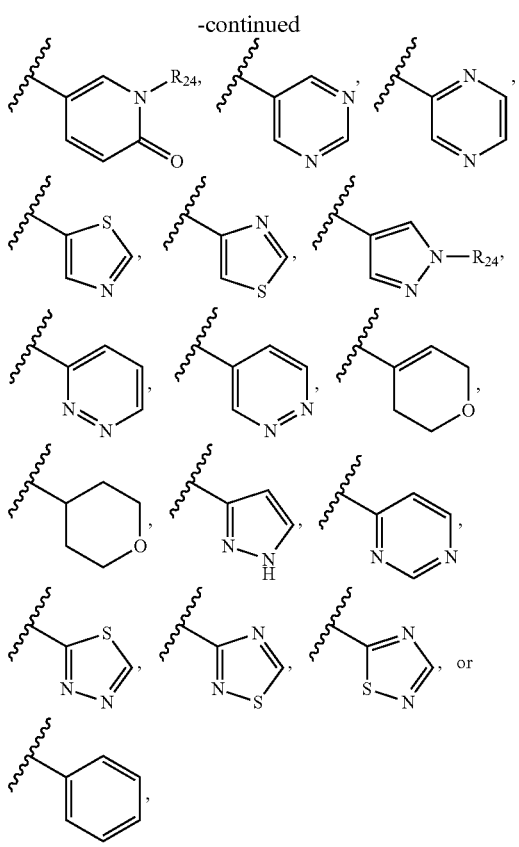

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyran, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^1$$_4$, —CO$_2$NR$^{14}$R$^{14}$, —NR$^{14}$CO$_2$NR$^{14}$R$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NCOR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—C$_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NCOR$^{14}$, OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n−1 is 2 to 4.

In another aspect, the present invention provides compound of formula (I), or enantiomers, diastereomers, tautomers, prodrugs or salts thereof, wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^1$ is $C_{1-10}$ alkyl substituted with 1-2 —OH, halo$C_{1-10}$ alkyl, $C_{2-12}$ alkenyl, or $C_{3-10}$ cycloalkyl, wherein the cycloalkyl may be substituted with 0-2 $R^{13}$; or $R^1$ is

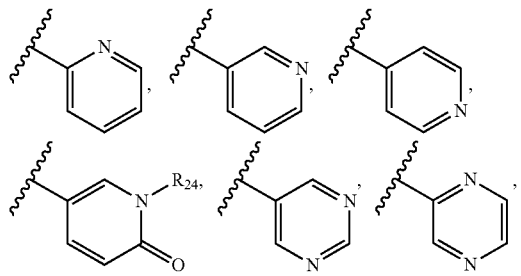

-continued

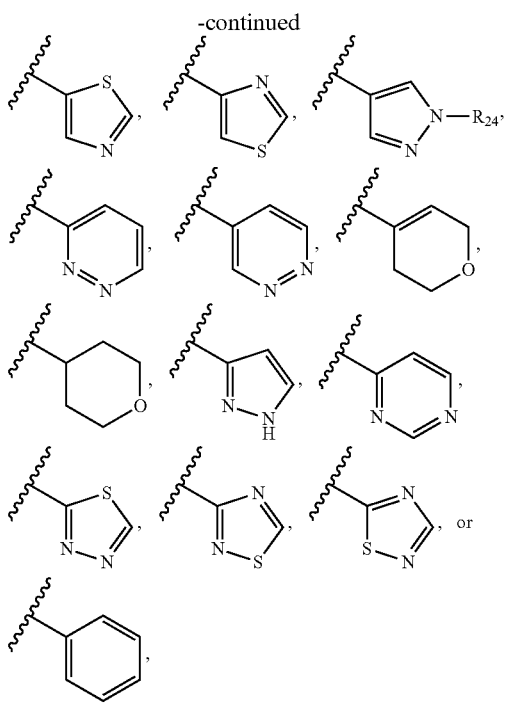

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyran, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^1_4$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NR$^{14}$COR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—C$_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NR$^{14}$COR$^{14}$, OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (I), or enantiomers, diastereomers, tautomers, prodrugs or salts thereof, wherein:

A is —(CH$_2$)$_m$—R$^2$, —CH(R$^{26}$)—R$^2$, —C(R$^{26}$)$_2$—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^1$ is $C_{1-10}$ alkyl substituted with 1-2 —OH, halo$C_{1-10}$ alkyl, $C_{2-12}$ alkenyl, or $C_{3-10}$ cycloalkyl, wherein the cycloalkyl may be substituted with 0-2 $R^{13}$; or $R^1$ is

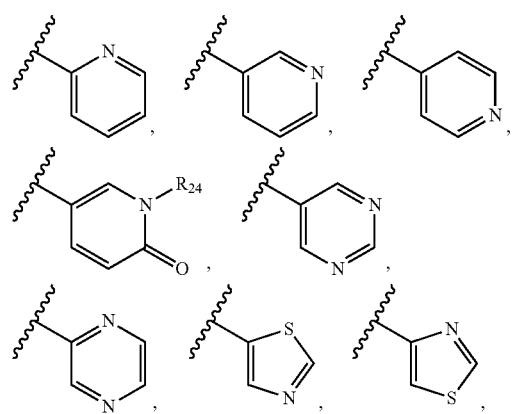

-continued

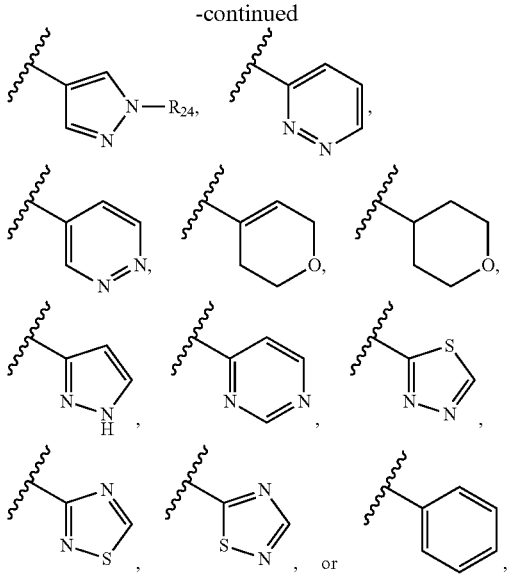

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyran, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^1_4$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NR$^{14}$COR$^{14}$, wherein the alkyl, cycloalkyl, alkenyl, alkoxy, aryl, heteroaryl and heterocyclyl may be substituted with 0-2 $R^{14a}$ and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—$C_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$, —NR$^{14}$COR$^{14}$, or OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O; or $R^{13}$ is SO$_2$NHP(O)(OH)$_2$;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O, and wherein the aryl and heteroaryl is optionally substituted with 0-1 of: halo, $C_{1-3}$alkyl, $C_{1-3}$haloalkyl, —O—$C_{1-3}$alkyl, or —O—$C_{1-3}$haloalkyl;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{1-6}$haloalkyl, $C_{3-6}$cycloalkyl, —(CH$_2$)-phenyl, or phenyl;

$R^{26}$, at each occurrence, is independently selected from hydrogen, —OH, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (Ia), or enantiomers, diastereomers, tautomers, prodrugs or salts thereof, wherein:

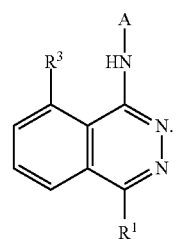

(Ia)

In another aspect, the present invention provides compound of formula (I) or (Ia), or enantiomers, diastereomers, tautomers, prodrugs or salts thereof, wherein:

A is —(CH$_2$)$_m$—R$^2$;

$R^1$ is $C_{1-6}$alkyl substituted with 1-2 —OH, $C_{2-6}$alkenyl, or $C_{3-6}$cycloalkyl, wherein the cycloalkyl may be substituted with 0-2 $R^{13}$; or $R^1$ is

[structures: 2-pyridinyl, 3-pyridinyl, 4-pyridinyl, or phenyl]

any of which may be substituted with 0-2 $R^{13}$;

$R^2$ is phenyl or pyridinyl;

$R^3$ is phenyl;

$R^{13}$, at each occurrence, is independently H, $C_{1-6}$alkyl, —$NR^{14}SO_2R^{14}$, —$CONR^4R^4$, —$SO_2NR^4R^4$, —$NR^4CO_2NR^4R^4$, —$NR^4COR^4$, or —$NR^4R^4$, wherein the alkyl may be substituted with 0-2 $R^{14a}$;

$R^{14}$, at each occurrence, is independently selected from hydrogen, $C_{1-6}$ alkyl, or phenyl, wherein the alkyl and phenyl may be substituted with 0-3 $R^{14a}$, and the heterocyclyl is pyrrolidinyl, or dioxanyl;

$R^{14a}$, at each occurrence, is independently selected from F, Cl, Br, I, $C_{1-6}$ alkyl, phenyl, $C_{3-6}$cycloalkyl, —$OR^{25}$ or dioxanyl;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 2; and n–1 is 2 to 4.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, or $C_{3-10}$ cycloalkyl, wherein the cycloalkyl may be substituted with 0-2 $R^{13}$; or $R^1$ is

[structures: pyridinyl isomers, N-substituted pyridinone, pyrimidinyl, pyrazinyl, pyridazinyl isomers, pyrimidinyl, or phenyl]

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, or $C_{3-10}$ cycloalkyl, wherein the cycloalkyl may be substituted with 0-1 $R^{13}$; or $R^1$ is

[structures: 2-pyridinyl, 3-pyridinyl, 4-pyridinyl, pyrimidinyl, pyrazinyl, or phenyl]

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, $C_{3-10}$ cycloalkyl, wherein the cycloalkyl may be substituted with 0-1 $R^{13}$; or $R^1$ is

[structures: 3-pyridinyl, or pyrazinyl]

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is

[structures: pyridinyl with $(R^{13})_{0-1}$, pyridinyl with $(R^{13})_{0-1}$, pyrazinyl with $(R^{13})_{0-1}$, or pyrazinyl with $(R^{13})_{0-1}$]

In another aspect, the present invention provides compound of formula (I) or (Ia), or enantiomers, diastereomers, tautomers, prodrugs or salts thereof, wherein:

$R^{13}$, at each occurrence, is independently H, —OH, F, Cl, Br, I, $C_{1-6}$ alkyl, $C_{1-6}$ alkoxy, halo$C_{1-6}$ alkyl, $C_{3-6}$cycloalkyl, phenyl, a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 R$^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$cycloalkyl, phenyl, wherein the alkyl, cycloalkyl, and phenyl, may be substituted with 0-3 R$^{14a}$; or alternatively, two R$^{14b}$'s are taken together with the atoms to which they are attached to form a cyclic ring, wherein the cyclic ring is morpholinyl, piperidinyl, or piperazinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs or salts thereof, wherein:

$R^{13}$, at each occurrence, is independently H, $C_{1-6}$ alkyl, a 4- to 12-membered heteroaryl, wherein the heteroaryl is selected from tetrazolyl, —CN, —NR$^{14}$SO$_2$R$^{14}$, —CONR$^{14}$R$^{14}$, —SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —CO$_2$R$^{14}$, or —NR$^{14}$R$^{14}$, wherein the alkyl, and heteroaryl may be substituted with 0-2 R$^{14a}$;

$R^{14}$, at each occurrence, is independently selected from hydrogen, $C_{1-6}$ alkyl, $C_{3-6}$cycloalkyl, or phenyl, wherein the alkyl, cycloalkyl, and phenyl, may be substituted with 0-3 R$^{14a}$; or two R$^{14b}$'s are taken together with the atoms to which they are attached to form a cyclic ring, wherein the cyclic ring is morpholinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), wherein:

$R^{13}$, at each occurrence, is independently H, —OH, F, Cl, Br, I, $C_{1-6}$ alkyl, $C_{1-6}$ alkoxy, halo$C_{1-6}$ alkyl, $C_{3-6}$cycloalkyl, phenyl, a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14}$R$^{1b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 R$^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$alkyl, $C_{3-6}$cycloalkyl, phenyl, wherein the alkyl, cycloalkyl, and phenyl, may be substituted with 0-3 R$^{14a}$; or alternatively, two R$^{14}$'s are taken together with the atoms to which they are attached to form a cyclic ring, wherein the cyclic ring is morpholinyl, piperidinyl, or piperazinyl, and may be substituted with 0-1 $C_{1-6}$alkyl;

$R^{14a}$, at each occurrence, is independently selected from F, Cl, Br, I, $C_{1-6}$ alkyl, halo$C_{1-6}$alkyl, phenyl, $C_{3-6}$cycloalkyl.

In another aspect, the present invention provides compound of formula (I) or (Ia), or enantiomers, diastereomers, tautomers, prodrugs or salts thereof, wherein:

$R^{13}$, at each occurrence, is independently H, —CN, —NHSO$_2$R$^{14}$, —CONH$_2$, —SO$_2$NR$^{14}$R$^{14}$, —NHCO$_2$NR$^{14b}$R$^{14b}$, —NHCOR$^{14}$, or —NH$_2$; and $R^{14}$, at each occurrence, is independently selected from hydrogen, or methyl.

In another aspect, the present invention provides compound of formula (I) or (Ia), or enantiomers, diastereomers, tautomers, prodrugs or salts thereof, wherein:

$R^{13}$, at each occurrence, is —SO$_2$NH$_2$.

In another aspect, the present invention provides compound of formula (I) or (Ia), or enantiomers, diastereomers, tautomers, prodrugs or salts thereof, wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^2$ is phenyl, pyridinyl, pyrazinyl, pyrimidinyl, piperidinyl, or pyridinone, any of which are substituted with 0-2 R$^{2a}$; and $R^{2a}$, at each occurrence, is independently H, —OH, F, $C_{1-6}$alkyl, $C_{1-6}$ alkoxy, or 6-SO$_2$NR$^{14}$R$^{14}$.

In another aspect, the present invention provides compound of formula (I) or (Ia), or enantiomers, diastereomers, tautomers, prodrugs or salts thereof, wherein:

A is —(CH$_2$)—R$^2$;

$R^2$ is phenyl,

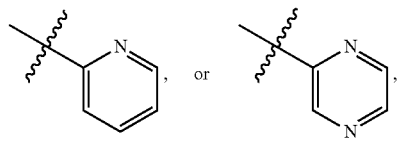 [SMILES: *c1ccccn1 ; *c1cnccn1]

any of which are substituted with 0-1 R$^{2a}$ and $R^{2a}$, at each occurrence, is independently H, —OH, F, $C_{1-6}$alkyl, $C_{1-6}$ alkoxy, $C_{1-6}$haloalkoxy, or SO$_2$NR$^{14}$R$^{14}$.

In another aspect, the present invention provides compound of formula (I) or (Ia), or enantiomers, diastereomers, tautomers, prodrugs or salts thereof, wherein:

A is —(CH$_2$)—R$^2$;

$R^2$ is phenyl,

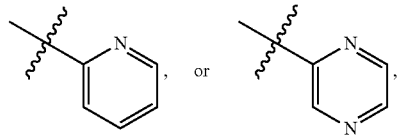 [SMILES: *c1ccccn1 ; *c1cnccn1]

any of which are substituted with 0-1 R$^{2a}$; or $R^{2a}$, at each occurrence, is independently H, —OH, F, $C_{1-6}$alkyl, $C_{1-6}$ alkoxy, $C_{1-6}$haloalkoxy, or SO$_2$NR$^{14}$R$^{14}$.

In another aspect, the present invention provides compound of formula (I) or (Ia), or enantiomers, diastereomers, tautomers, prodrugs or salts thereof, wherein:

A is —(CH$_2$)—R$^2$; and
R$^2$ is phenyl or

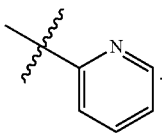 [SMILES: *c1ccccn1]

In another aspect, the present invention provides compound of formula (I) or (Ia), or enantiomers, diastereomers, tautomers, prodrugs or salts thereof, wherein:
A is —(CH$_2$)—R$^2$;
R$^2$ is phenyl,

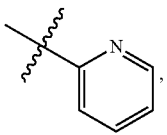

or C$_{1-6}$alkyl, any of which are substituted with 0-1 R$^{2a}$; and
R$^{2a}$, at each occurrence, is independently H or F.

In another aspect, the present invention provides compound of formula (I) or (Ia), or enantiomers, diastereomers, tautomers, prodrugs or salts thereof, wherein:
R$^3$ is phenyl.

In another aspect, the present invention provides compound of formula (I) or (Ia), or enantiomers, diastereomers, tautomers, prodrugs or salts thereof, wherein:
R$^{24}$, at each occurrence, is independently selected from hydrogen, C$_{1-6}$alkyl, C$_{3-6}$cycloalkyl, or phenyl;
R$^{25}$, at each occurrence, is independently selected from hydrogen, C$_{1-6}$alkyl, C$_{3-6}$cycloalkyl, or phenyl; and
R$^{26}$, at each occurrence, is independently selected from hydrogen, C$_{1-6}$alkyl, C$_{3-6}$cycloalkyl, or phenyl.

In another aspect, the present invention provides compound of formula (I) or (Ia), or enantiomers, diastereomers, tautomers, prodrugs or salts thereof, wherein:
R$^{24}$, at each occurrence, is independently selected from hydrogen, methyl or ethyl;
R$^{25}$, at each occurrence, is independently selected from hydrogen methyl or ethyl; and
R$^{26}$, at each occurrence, is independently selected from hydrogen, methyl or ethyl.

In another aspect, the present invention provides compound of formula (I) or (Ia), or enantiomers, diastereomers, tautomers, prodrugs or salts thereof, wherein:
m is 0-2; and
n–1 is 1-2.

In another aspect, the present invention provides compound of formula (I) or (Ia), or enantiomers, diastereomers, tautomers, prodrugs or salts thereof, wherein:
m is 1 or 2;
n–1 is 2; and
n is 1.

In another aspect, the present invention provides compound of formula (I) or (Ia), or salts thereof, wherein:
R$^{13}$ is SO$_2$NHP(O)(OH)$_2$.

In another aspect, the present invention provides compound of formula (I) or (Ia), or salts thereof, wherein:
R$^1$ pyridinyl substituted with 1 R$^{13}$; and
R$^{13}$ is SO$_2$NHP(O)(OH)$_2$.

In another aspect, the present invention provides compound of formula (I) or (Ia), or salts thereof, wherein:
R$^1$ is

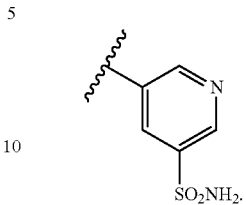

In another aspect, the present invention provides compound of formula (I) or (Ia), or salts thereof, wherein:
R$^1$ is

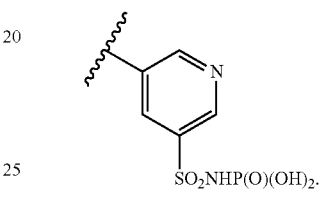

In another embodiment, compounds, enantiomers, diastereomers, tautomers, or salt thereof, of the present invention are selected from the compounds exemplified in the examples.

In one embodiment, pharmaceutical compositions comprising a therapeutically effective amount of at least one compound of formula (I), (Ia), and/or compounds exemplified in the examples.

In another embodiment, pharmaceutical compositions comprising a therapeutically effective amount of at least one compound of formula (I), (Ia), and/or compounds exemplified in the examples, and at least one other therapeutic agent, for example, anti-arrhythmic agents, calcium channel blockers, anti-platelet agents, anti-hypertensive agents, anti thrombotic/anti thrombolytic agents, anti coagulants, HMG-CoA reductase inhibitors, anti diabetic agents, thyroid mimetics, mineralocorticoid receptor antagonists, and cardiac glycosides, are provided.

In yet another embodiment, pharmaceutical compositions comprising a therapeutically effective amount of at least one compound of formula (I), (Ia), or compounds exemplified in the examples, and at least one other therapeutic agent, for example, sotalol, dofetilide, diltiazem, verapamil, clopidogrel, cangrelor, ticlopidine, CS-747, ifetroban, aspirin, a beta adrenergic blocker, an ACE inhibitor, an A II antagonist, an ET antagonist, a dual ET/A II antagonist, a vasopepsidase inhibitor, tPA, recombinant tPA, TNK, nPA, a factor VIIa inhibitor, a factor Xa inhibitor, a factor XIa inhibitor, a thrombin inhibitor, warfarin, a heparin, pravastatin, lovastatin, atorvastatin, simvastatin, NK-104, ZD-4522, a biguanide, a biguanide/glyburide combination, spironolactone, eplerinone, digitalis and ouabain, are provided.

In still yet another embodiment, pharmaceutical compositions comprising a therapeutically effective amount of at least one compound of formula (I), (Ia), or compounds exemplified in the examples, and at least one other therapeutic agent, for example, captopril, zofenopril, fosinopril, enalapril, ceranopril, cilazopril, delapril, pentopril, quinapril, ramipril, lisinopril, omapatrilat, gemopatrilat, and apixaban, are provided.

In one embodiment, methods of treating or preventing arrhythmia comprising administering to a patient in need thereof an effective amount of at least one compound of formula (I), (Ia), or compounds exemplified in the examples, are provided.

In another embodiment, methods of treating or preventing supraventricular arrhythmia, for example, atrial fibrillation and atrial flutter, comprising administering to a patient in need thereof an effective amount of at least one compound of formula (I), (Ia), or compounds exemplified in the examples, are provided.

In one embodiment, a method of controlling heart rate comprising administering to a patient in need thereof an effective amount of at least one compound of formula (I), (Ia), or compounds exemplified in the examples, is provided.

In another embodiment, methods of treating an $I_{Kur}$-associated conditions, for example, gastrointestinal disorders, such as reflux esophagitis and a motility disorder; inflammatory and/or immunological diseases, such as chronic obstructive pulmonary disease; diabetes; cognitive disorders; migraines; epilepsy; and hypertension, comprising administering to a patient in need thereof an effective amount of at least one compound of formula (I), (Ia), or compounds exemplified in the examples, are provided.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to treatment of diseases or disorders associated with inhibition of potassium channel function, wherein the disease or disorder is atrial fibrillation, controlling heart rate, and/or prophylactically treating arrhythmia, comprising administering a therapeutically effective amount of a compound of the present invention or an individual isomer or mixture of isomers or a pharmaceutically acceptable salt thereof.

The compounds of the invention may be useful in therapy.

The compounds of the invention may be used for the manufacture of a medicament for the treatment and/or prophylaxis of diseases or disorders associated with inhibition of potassium channel function, of the $K_v1$ subfamily of voltage gated $K^+$ channels, of $K_v1.5$ (which have been linked to the ultra-rapidly activating delayed rectifier $K^+$ current $I_{Kur}$, and/or $K_v1.3$ channels, and/or $K_v1.1$ channels.

The compounds of the invention can be used alone, in combination with other compounds of the present invention, or in combination with one or more, preferably one to two other agent(s).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis*, Third Edition, Wiley (1999). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*, Fourth Edition, Wiley & Sons, New York, N.Y. (1992); Katritzky, A. R. et al., eds., *Comprehensive Organic Functional Groups Transformations*, First Edition, Elsevier Science Inc., Tarrytown, N.Y. (1995); Larock, R. C., *Comprehensive Organic Transformations*, VCH Publishers, Inc., New York, N.Y. (1989); and references therein.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "Rt" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below $X^1$, $X^2$, A and $R^1$ are as described for a compound of Formula (I). The following are the definitions of symbols used in the Examples:

$Al_2O_3$ Aluminum oxide
Ar Aryl
$BF_3.OEt_2$ Boron trifluoride etherate
$CH_2Cl_2$ Dichloromethane
$CHCl_3$ Chloroform
$CDCl_3$ Deuterated chloroform
$CD_3OD$ Deuterated methanol
DCM Dichloromethane
DIPEA N,N-Diisopropylethylamine
DMAP 4-Dimethylaminopyridine
DMF N,N-dimethyl formamide
DMSO Dimethyl sulfoxide
DMSO-$d_6$ Deuterated dimethyl sulfoxide
Et Ethyl
EtOAc Ethyl acetate
EtOH Ethanol
HATU (O-(7-azabenzotriazol-1-yl)-N,N,N',N'-tetramethyluronium hexafluorophosphate)
HCl Hydrochloric acid
HCOOH Formic acid
$HCOONH_4$ Ammonium formate
KI Potassium iodide
$K_2CO_3$ Potassium carbonate
KOAc Potassium acetate
$K_3PO_4$ Potassium phosphate
LiOH Lithium hydroxide
Me Methyl
MeOH Methanol
NaH Sodium hydride
$NaHCO_3$ Sodium bicarbonate
$NaNO_2$ Sodium nitrite
$Na_2SO_4$ Sodium sulfate
$Na_2S_2O_3$ Sodium thiosulfate
$NH_3$ Ammonia
$NH_4OAc$ Ammonium acetate
Pd/C Palladium on carbon
$Pd_2(dba)_3$ Tris(dibenzylideneacetone)dipalladium (0)
$Pd(dppf)_2Cl_2:CH_2Cl_2$ [1,1'Bis(diphenylphosphino)ferrocene]dichloropalladium(II), complex with dichloromethane
$POCl_3$ Phosphorus oxychloride
THF Tetrahydrofuran
TFA Trifluoroacetic acid Synthesis A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Wiley and Sons (1991)).

Scheme 1

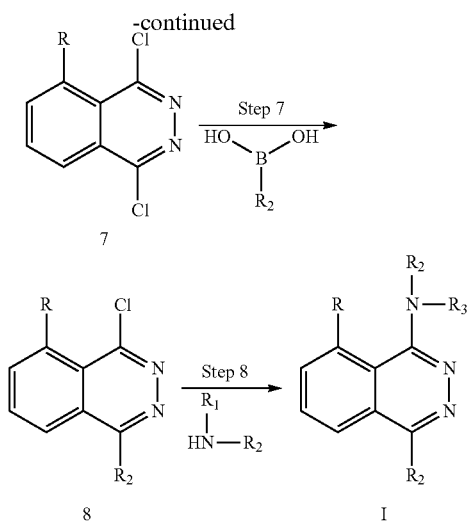

Compounds of general formula (I) may be synthesized according to Scheme 1. Commercially available nitrophthalic acid can be converted to the corresponding diester 2, using for example methyl iodide. Dimethyl 3-nitrophthalate 2, was reduced to get 3-aminodimethylphthalate 3 (for example, Thottumkara et al *Tetrahedron Letters*, 43:569-572 (2002)). Dimethyl 3-aminophthalate 3 was subjected to diazotization conditions followed by treatment with KI to afford dimethyl 3-iodophthalate 4. Suzuki mediated cross-coupling with boronic acids or esters using palladium catalysts yielded compounds shown by structure 5 where R=alkyl, optionally substituted aryl, optionally substituted heteroaryl. Treatment of compound 5 with hydrazine hydrate (for example in solvents like water, ethanol, toluene, etc.) undergoes cyclization to furnish phthalazinedioines 6. Compound 6 was converted to the corresponding dichloro phthalazine 7 using chlorinating agents for example, phosphorous oxychloride. Dichloro-5-phthalazine 7 was converted to compounds 8 under palladium mediated Suzuki cross-coupling with boronic esters or acids. Displacement of the second chloride with various amines generated compounds of the general formula (I).

EXAMPLES

The following Examples are offered to better illustrate, but not limit some of the preferred embodiments of the application and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

General Methods

The following methods were used in the working Examples, except where noted otherwise.

Analytical HPLC and HPLC/MS Methods Employed in Characterization of Examples

Preparative HPLC was carried on AGILENT® 1200 series, Shimadzu prominence or Waters systems. Preparative SFC was performed on Thar instrument. Reverse phase analytical HPLC/MS was performed on AGILENT® 1200 systems coupled with Mass Spectrometers. LCMS was performed on AGILENT® 1200 or Waters AQUITY® system coupled with Mass Spectrometer. Chiral analytical LC was performed on a Thar Analytical SFC instrument.

Condition 1:
Column=Ascentis Express C18, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.4 min; Stop time=4 min
Isocratic time=1.6 min
Flow Rate=1 mL/min; Wavelength=220 nm Condition 2:
Column=Ascentis Express C8, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm Condition 3:
Column=Ascentis Express C8, 2.1×50 mm, 2.7 μm
Solvent A=$CH_3CN$ (10%)+10 mM $NH_4COOH$ in $H_2O$ (90%)
Solvent B=$CH_3CN$ (90%)+10 mM $NH_4COOH$ in $H_2O$ (10%)
Start % B=0; Final % B=100
Gradient time=1.6 min; Stop time=4 min
Isocratic time=1.6 min
Flow Rate=1 mL/min; Wavelength=220 nm Condition 4:
Column=Ascentis Express C18 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm Condition 5:
Column=XBridge C18, 2.1×50 mm, 2.5 μm
Solvent A=$CH_3CN$ (5%)+10 mM $NH_4HCO_3$ in $H_2O$ (95%)
Solvent B=$CH_3CN$ (95%)+10 mM $NH_4HCO_3$ in $H_2O$ (5%)
Start % B=0; Final % B=100
Gradient time=1.7 min; Stop time=4 min
Isocratic time=1.5 min
Flow Rate=1 mL/min; Wavelength=220 nm Condition 6:
Column=ZORBAX® SB-Aq, 4.6×50 mm, 3.5 μm
Solvent A=$CH_3CN$ (5%)+10 mM $NH_4COOH$ in $H_2O$ (95%)
Solvent B=$CH_3CN$ (95%)+10 mM $NH_4COOH$ in $H_2O$ (5%)
Start % B=5; Final % B=95
Gradient time=1.7 min; Stop time=4 min
Isocratic time=1.5 min
Flow Rate=1 mL/min; Wavelength=220 nm Condition 7:
Column=Ascentis Express C8, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wavelength=220 nm Condition 8:
Column=XBridge BEH C18, 2.1×50 mm, 2.5 μm
Solvent A=0.1% HCOOH in $H_2O$
Solvent B=0.07% HCOOH in $CH_3CN$
Start % B=10; Final % B=100
Gradient time=2.0 min; Stop time=4.0 min
Isocratic time=1. min
Rate=1.2 mL/min; Wavelength=220 nm Condition 9:
Column=ZORBAX® SB C18, 2.1×30 mm, 3.5 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=6; Final % B=100
Gradient time=1.5 min; Stop time=3 min
Isocratic time=0.7 min
Flow Rate=1.5 mL/min; Wavelength=220 nm
Condition 10:
Column=Kinetex C-18, 2.1×50 mm, 2.6 μm
Solvent A=$CH_3CN$ (2%)+0.1% $NH_4COOH$ in $H_2O$ (98%)
Solvent B=$CH_3CN$ (98%)+0.1% $NH_4COOH$ in $H_2O$ (2%)
Start % B=0; Final % B=100
Gradient time=1.7 min; Stop time=4 min
Isocratic time=1.5 min
Flow Rate=1 mL/min; Wavelength=220 nm
Condition 11:
Column=Acquity BEH C18, 2.1×50 mm, 1.7 μm
Solvent A=Buffer: $CH_3CN$ (95:5)
Solvent B=Buffer: $CH_3CN$ (5:95)
Buffer=10 mM $NH_4OAc$ in $H_2O$ (pH 5, adjusted with HCOOH)
Start % B=5; Final % B=95
Gradient time=1.1 min; Stop time=2.4 min
Isocratic time=0.6 min
Flow Rate=0.8 mL/min; Wave length=220 nm
Condition 12:
Column: Acquity BEH C18, 2.1×50 mm, 1.7 μm
Solvent A=0.1% TFA in $H_2O$
Solvent B=0.1% TFA in $CH_3CN$
Start % B=2; Final % B=98
Gradient time=1 min; Stop time=2.2 min
Isocratic time=0.6 min
Flow Rate=0.8 mL/min; Wave length=220 nm
Condition 13:
Column=SYMMETRY® C18, 250×19 mm, 7 μm
Solvent A=10 mM $NH_4OAc$ in $H_2O$ (pH 4.5, adjusted with AcOH)
Solvent B=$CH_3CN$
Start % B=50; Final % B=90
Gradient time=10 min; Stop time=19 min
Isocratic time=5 min
Flow=17 mL/min; Wave length=220 nm
Condition 14:
Column=SunFire C18, 19×150 mm, 5 μm
Solvent A=10 mM $NH_4OAc$ in $H_2O$ (pH 4.5, adjusted with AcOH)
Solvent B=$CH_3CN$
Isocratic=A:B (20:80)
Flow=16 mL/min; Wave length=220 nm
Condition 15:
Column=XSelect C18, 19×150 mm, 5 μm
Solvent A=10 mM $NH_4OAc$ in $H_2O$
Solvent B=$CH_3CN$
Start % B=30; Final % B=70
Gradient time-1=12 min;
Start % B=70; Final % B=100
Gradient time=3 min; Stop time=19 min
Flow=16 mL/min; Wave length=220 nm
Condition 16:
Column=Inertsil ods, 19×250 mm, 5.0 μm
Solvent A=10 mM $NH_4OAc$ in $H_2O$
Solvent B=$CH_3CN$
Start % B=30; Final % B=70
Gradient time-1=5 min;
Final % B=100
Gradient time-2=8 min; Stop time=15 min
Flow=16 mL/min; Wave length=220 nm
Condition 17:
Column=Inertsil ods, 19×250 mm, 5.0 μm
Solvent A=10 mM $NH_4OAc$ in $H_2O$
Solvent B=$CH_3CN$
Start % B=30; Final % B=70
Gradient time-1=12 min;
Final % B=100
Gradient time-2=3 min; Stop time=20 min
Flow=16 mL/min; Wave length=220 nm
Condition 18:
Column=XBridge C18, 19×150 mm, 5 μm
Solvent A=10 mM $NH_4OAc$ in $H_2O$ (pH 4.5, adjusted with AcOH)
Solvent B=$CH_3CN$
Start % B=10; Final % B=40
Gradient time-1=10 min;
Final % B=100
Gradient time-2=5 min; Stop time=20 min
Flow=17 mL/min; Wave length=220 nm
Condition 19:
Column=XBridge C18, 19×150 mm, 5 μm
Solvent A=10 mM $NH_4OAc$ in $H_2O$ (pH 4.5, adjusted with AcOH)
Solvent B=$CH_3CN$
Start % B=30; Final % B=70
Gradient time-1=10 min;
Final % B=100
Gradient time-2=5 min; Stop time=20 min
Flow=16 mL/min; Wave length=220 nm
Condition 20:
Column=Kinetex C18, 19×150 mm, 5 μm
Solvent A=10 mM $NH_4OAc$ in $H_2O$
Solvent B=$CH_3CN$
Start % B=20; Final % B=50
Gradient time-1=10 min;
Final % B=100
Gradient time-2=2 min; Stop time=20 min
Flow=15 mL/min; Wave length=220 nm
Condition 21:
Column=Atlantis C18, 19×250 mm, 7 μm
Solvent A=10 mM $NH_4OAc$ in $H_2O$ (pH 4.5, adjusted with AcOH)
Solvent B=$CH_3CN$
Start % B=30; Final % B=70
Gradient time-1=11 min;
Final % B=100
Gradient time-2=4 min; Stop time=20 min
Flow=16 mL/min; Wave length=220 nm
Condition 22:
Column=SunFire C18, 19×150 mm, 5 μm
Solvent A=10 mM $NH_4OAc$ in $H_2O$ (pH 4.5, adjusted with AcOH)
Solvent B=$CH_3CN$
Start % B=20; Final % B=70
Gradient time-1=10 min;
Final % B=100
Gradient time-2=5 min; Stop time=20 min
Flow=16 mL/min; Wave length=220 nm
Condition 23:
Column=SYMMETRY® C18, 19×250 mm, 5 μm
Solvent A=10 mM $NH_4OAc$ in $H_2O$ (pH 4.5, adjusted with AcOH)
Solvent B=$CH_3CN$
Start % B=20; Final % B=90
Gradient time=10 min; Stop time=20 min
Flow=16 mL/min; Wave length=220 nm Condition 24:
Column=XBridge Phenyl, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 and 254 nm
Condition 25:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=23 min
Isocratic time=3 min
Flow Rate=1 mL/min; Wavelength=220 and 254 nm
Condition 26:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=0; Final % B=50
Gradient time-1=15 min
Final % B=100
Gradient time-2=3 min
Isocratic time=5 min
Stop time=28 min
Flow Rate=1 mL/min; Wavelength=220 and 254 nm
Condition 27:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=25 min; Stop time=30 min
Isocratic time=5 min
Flow Rate=1 mL/min; Wavelength=220 and 254 nm
Condition 28:
Column=SunFire C18, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=15 min
Isocratic time=3 min
Flow Rate=1 mL/min; Wavelength=220 and 254 nm
Condition 29:
Column=CHIRALCEL® OJH, 250×4.6 mm, 5 μm
Solvent A=$CO_2$
Solvent B=0.3% DEA in MeOH
Isocratic=A:B (85:15)
Flow=3 mL/min; Wave length=220 nm
Condition 30:
Column=SunFire C-18, 19×150 mm, 5μ
Solvent A=10 mM $NH_4OAc$ in $H_2O$ (pH 4.5, adjusted with AcOH)
Solvent B=$CH_3CN$
Start % B=10; Final % B=45
Gradient time=10 min;
Flow=16 mL/min; Wave length=220 nm Condition 31:
Column=KROMASIL® Packed C-18, 19×250 mm, 5μ
Solvent A=10 mM $NH_4OAc$ in $H_2O$ (pH 4.5, adjusted with AcOH)
Solvent B=$CH_3CN$
Start % B=40; Final % B=80
Gradient time-1=10 min;
Start % B=80; Final % B=100
Gradient time-2=5 min;
Flow=16 mL/min; Wave length=220 nm
Condition 32:
Column=XSelect C-18, 19×150 mm, 5μ
Solvent A=10 mM $NH_4OAc$ in $H_2O$ (pH 4.5, adjusted with AcOH)
Solvent B=$CH_3CN$
Start % B=30; Final % B=70
Gradient time-1=10 min;
Start % B=70; Final % B=100
Gradient time-2=5 min;
Flow=16 mL/min; Wave length=220 nm
Condition 33:
Column=SYMMETRY® C8, 19×300 mm, 7μ
Solvent A=10 mM $NH_4OAc$ in $H_2O$ (pH 4.5, adjusted with AcOH)
Solvent B=$CH_3CN$
Start % B=50; Final % B=90
Gradient time=10 min;
Flow=15 mL/min; Wave length=220 nm
Condition 34:
Column=Ascentis Express C18, 2.1×50 mm, 2.7μ
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.7 min; Stop time=4 min
Isocratic time=1.5 min
Flow Rate=1 mL/min; Wavelength=220 nm
Condition 35:
Column=XBridge Phenyl, 4.6×150 mm, 5μ
Solvent A=Buffer: $CH_3CN$ (95:5)
Solvent B=Buffer: $CH_3CN$ (5:95)
Buffer=10 mM $NH_4OAc$ in $H_2O$
Start % B=10; Final % B=100
Gradient time=25 min; Stop time=32 min
Isocratic time=5 min
Flow Rate=1 mL/min; Wavelength=220 and 254 nm
Condition 36:
Column=XBridge Prep OBD C18, 19×150 mm, 5μ
Solvent A=10 mM $NH_4OAc$ in $H_2O$ (pH 4.5, adjusted with AcOH)
Solvent B=$CH_3CN$
Start % B=10; Final % B=45
Gradient time-1=8 min;
Isocratic time=8 min;
Start % B=45; Final % B=100
Gradient time-2=2 min;
Isocratic time=3 min;
Flow=15 mL/min; Wave length=220 nm
Condition 37:
Column=Ascentis Express C18, 2.1×50 mm, 2.7μ
Solvent A=$CH_3CN$ (5%)+10 mM $NH_4OAc$ in $H_2O$ (95%)
Solvent B=$CH_3CN$ (95%)+10 mM $NH_4OAc$ in $H_2O$ (5%)
Start % B=0; Final % B=100
Gradient time=3.0 min; Stop time=4 min
Flow Rate=1.1 mL/min; Wavelength=220 nm Condition 38:
Column=Ascentis Express C18, 2.1×50 mm, 2.7μ
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.7 min; Stop time=4 min
Isocratic time=1.7 min
Flow Rate=1 mL/min; Wavelength=220 nm
Condition 39:
Column=Kinetex C-18, 2.1×50 mm, 2.6μ
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.7 min; Stop time=4 min
Isocratic time=1.5 min
Flow Rate=1 mL/min; Wavelength=220 nm
Condition 40:
Column=Ascentis Express C18, 2.1×50 mm, 2.7μ
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.7 min; Stop time=4 min
Isocratic time=1.3 min
Flow Rate=1 mL/min; Wavelength=220 nm
Condition 41:
Column=WHELK-O® 1 (R,R), 250×4.6 mm, 5μ
Solvent A=CO$_2$
Solvent B=30 mM Ammonia in MeOH
Isocratic=A:B (3:2)
Flow=4 mL/min; Wave length=210 nm
Condition 42:
Column=Gemini C18, 21.1×250 mm, 5μ
Solvent A=H$_2$O
Solvent B=CH$_3$CN
Start % B=10; Final % B=55
Gradient time=16 min;
Flow=17 mL/min; Wave length=220 nm NMR Employed in Characterization of Examples $^1$H NMR spectra were obtained with Bruker or JEOL® Fourier transform spectrometers operating at frequencies as follows: $^1$H NMR: 400 MHz or 300 MHz (Bruker). $^{13}$C NMR: 100 MHz or 75 MHz (Bruker). Spectra data are reported in the format: chemical shift (multiplicity, coupling constants, number of hydrogens). Chemical shifts are specified in ppm downfield of a tetramethylsilane internal standard (δ units, tetramethylsilane+0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

Example 1

5-(5-Phenyl-4-(pyridin-2-ylmethylamino)phthalazin-1-yl)pyridine-3-sulfonamide

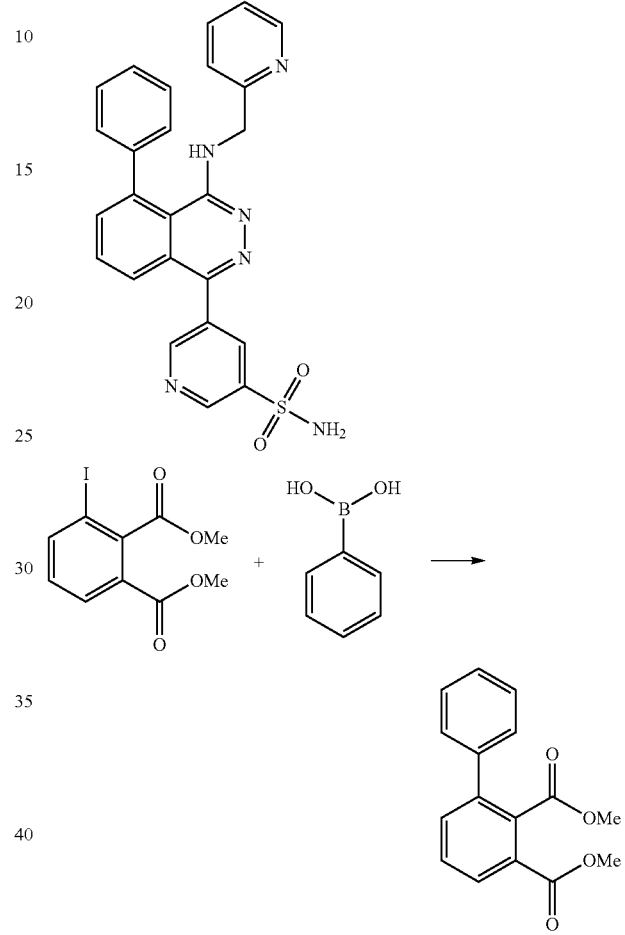

A solution of dimethyl 3-iodophthalate (WO 2008/115516) (1.00 g, 3.12 mmol), phenylboronic acid (0.571 g, 4.69 mmol), K$_2$CO$_3$ (0.880 g, 9.30 mmol) in 1,4-dioxane (15 mL) and water (4 mL) was purged with nitrogen for 30 min. Pd(dppf)Cl$_2$:DCM (0.219 g, 0.312 mmol) was added and the reaction mixture was heated at 100° C. for 12 h. The reaction mixture was filtered through a pad of CELITE® and the pad was washed with water (50 mL). The filtrate was extracted with EtOAc (2×100 mL). The combined organic extracts were dried over anhydrous Na$_2$SO$_4$, filtered and concentrated under reduced pressure. The resulting residue was purified by combiflash (REDISEP®, silica gel, 12 g, 20% EtOAc/hexanes) to obtain dimethyl [1,1'-biphenyl]-2,3-dicarboxylate (0.65 g, 77.0%) as an off-white solid. LCMS (Condition 11): retention time 0.96 min, [M-MeOH+1]=239.3. $^1$H NMR (400 MHz, DMSO-d$_6$) δ 3.59 (s, 3 H), 3.85 (s, 3 H), 7.33-7.49 (m, 5 H), 7.68-7.70 (m, 2 H), 7.95-8.00 (m, 1 H).

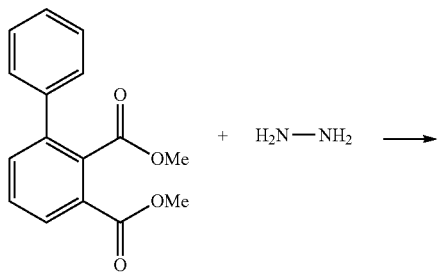

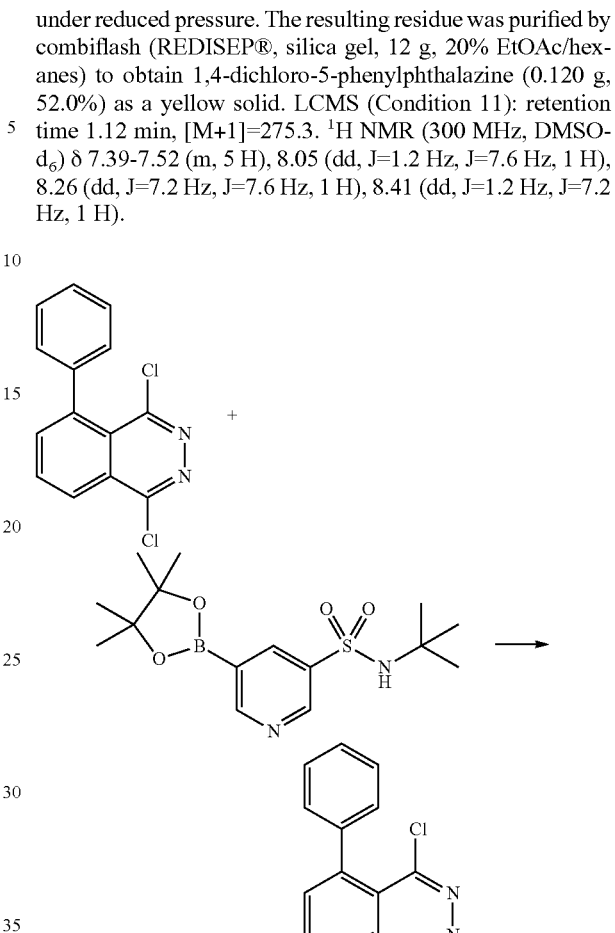

under reduced pressure. The resulting residue was purified by combiflash (REDISEP®, silica gel, 12 g, 20% EtOAc/hexanes) to obtain 1,4-dichloro-5-phenylphthalazine (0.120 g, 52.0%) as a yellow solid. LCMS (Condition 11): retention time 1.12 min, [M+1]=275.3. $^1$H NMR (300 MHz, DMSO-$d_6$) δ 7.39-7.52 (m, 5 H), 8.05 (dd, J=1.2 Hz, J=7.6 Hz, 1 H), 8.26 (dd, J=7.2 Hz, J=7.6 Hz, 1 H), 8.41 (dd, J=1.2 Hz, J=7.2 Hz, 1 H).

A solution of dimethyl [1,1'-biphenyl]-2,3-dicarboxylate (0.600 g, 2.22 mmol) in hydrazine hydrate (5.00 mL, 159 mmol) was heated in a sealed tube at 100° C. for 16 h. The reaction mixture was acidified to pH~3 with 1.5N HCl. The resulting precipitate was filtered, washed with water (3×50 mL) and hexanes (2×50 mL). The precipitate was dried under vacuum to yield 5-phenylphthalazine-1,4-diol (0.450 g, 85.0%) as an off-white solid. LCMS (Condition 11): retention time 0.76 min, [M+1]=239.4. $^1$H NMR (400 MHz, DMSO-$d_6$) δ 7.29-7.34 (m, 5 H), 7.60 (d, J=7.6 Hz, 1 H), 7.89 (t, J=7.6 Hz, 1 H), 8.13 (br s, 1 H), 11.40 (br s, 2 H).

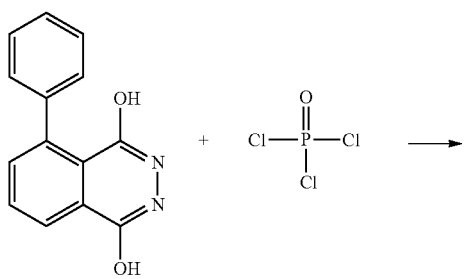

A solution of 5-phenylphthalazine-1,4-diol (0.200 g, 0.839 mmol) in POCl$_3$ (2.00 mL, 21.5 mmol) was added N,N-dimethylbenzenamine (0.106 mL, 0.839 mmol) and the contents were heated in a sealed tube at 100° C. for 16 h. The reaction mixture was allowed to cool to room temperature and concentrated under reduced pressure. The residue was dissolved in DCM (50 mL) and washed with ice cold solution of saturated NaHCO$_3$ (2×5 mL). The combined organic extracts were dried over anhydrous Na$_2$SO$_4$, filtered and concentrated To a solution of 1,4-dichloro-5-phenylphthalazine (0.400 g, 1.45 mmol) and N-(tert-butyl)-5-(4,4,5,5-tetramethyl-1,3,2-dioxaborolan-2-yl)pyridine-3-sulfonamide (0.742 g, 2.18 mmol) (Johnson et al., WO 2011/28741) in 1,4-dioxane (15 mL) and water (3 mL) was added K$_3$PO$_4$ (0.617 g, 2.91 mmol) and the contents purged with nitrogen for 10 min. Tricyclohexylphosphine (10.2 mg, 0.0360 mmol) was added followed by Pd$_2$(dba)$_3$ (0.0130 g, 0.0150 mmol) and heated at 95° C. for 12 h. The reaction mixture was allowed to cool to ambient temperature. The reaction mixture was diluted with HCOONH$_4$ buffer (pH~5) solution and extracted with EtOAc (3×75 mL). The combined organic extracts were dried over anhydrous Na$_2$SO$_4$, filtered and concentrated under reduced pressure. The resulting residue was purified by combiflash (REDISEP®, silica gel, 12 g, 30% EtOAc/hexanes) to obtain N-(tert-butyl)-5-(4-chloro-5-phenylphthalazin-1-yl)pyridine-3-sulfonamide (0.500 g, 76.0%) as a pale yellow solid. LCMS (Condition 11): retention time 1.04 min, [M+1]=453.2. $^1$H NMR (400 MHz, DMSO-$d_6$) δ 1.20 (s, 9 H), 7.43-

7.46 (m, 2 H), 7.50-7.54 (m, 3 H), 7.98 (s, 1 H), 7.99 (dd, J=1.2 Hz, J=8.0 Hz, 1H), 8.03 (dd, J=1.2 Hz, J=7.2 Hz, 1 H), 8.15 (dd, J=7.2 Hz, J=8.0 Hz, 1 H), 8.58 (t, J=2.0 Hz, 1 H), 9.17 (d, J=2.0 Hz, 1 H), 9.23 (d, J=2.0 Hz, 1 H).

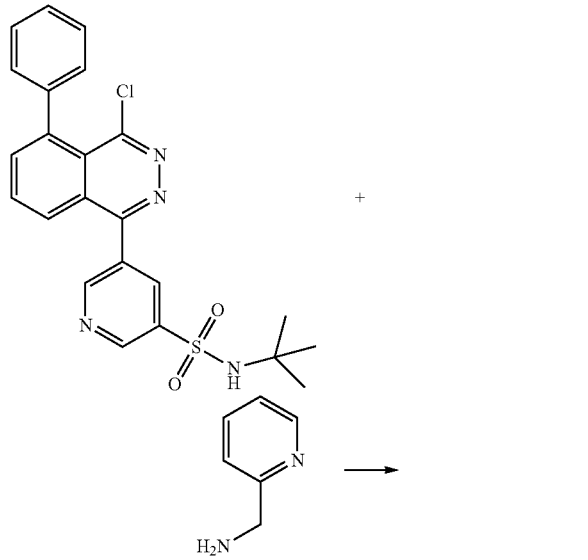

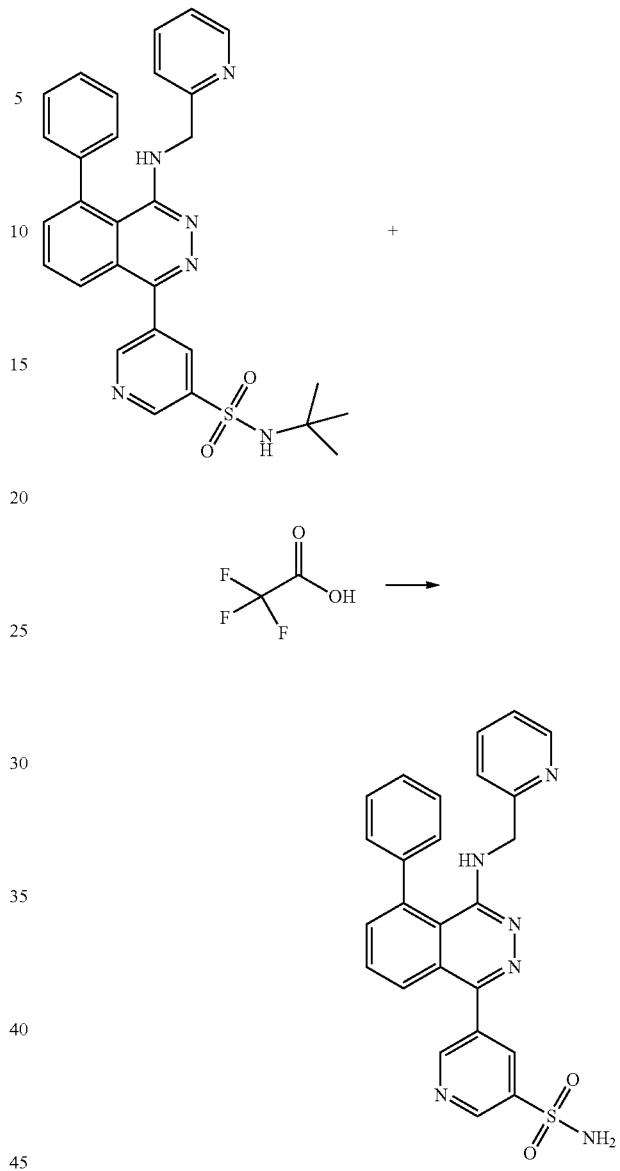

To a solution of N-(tert-butyl)-5-(4-chloro-5-phenylphthalazin-1-yl)pyridine-3-sulfonamide (0.400 g, 0.883 mmol) in toluene (5 mL) was added pyridin-2-ylmethanamine (0.0950 g, 0.883 mmol) and the contents were heated at 100° C. for 12 h. The volatile components were removed under reduced pressure and the resulting residue was purified by preparative HPLC (Condition 16 as described in general methods) to yield N-(tert-butyl)-5-(5-phenyl-4-((pyridin-2-ylmethyl)amino)phthalazin-1-yl)pyridine-3-sulfonamide (35.0 mg, 7.55%) as a white solid. LCMS (Condition 4): retention time 2.47 min, [M+1]=525.2. HPLC (Condition 28): retention time=6.97 min, purity 96.32%. $^1$H NMR (400 MHz, CD$_3$OD) δ 1.30 (s, 9 H), 4.68 (s, 2 H), 7.24 (dd, J=4.8 Hz, J=7.2 Hz, 1 H), 7.27 (d, J=7.6 Hz, 1 H), 7.52 (br s, 5 H), 7.72 (dd, J=1.6 Hz, J=7.6 Hz, 1 H), 7.77 (dd, J=1.2 Hz, J=7.2 Hz, 1 H), 7.84 (dd, J=1.2 Hz, J=8.4 Hz, 1 H), 7.91-7.96 (m, 1 H), 8.31 (d, J=4.4 Hz, 1 H), 8.55 (t, J=2.0 Hz, 1 H), 9.07 (d, J=2.0 Hz, 1 H), 9.18 (d, J=2.0 Hz, 1 H).

N-(tert-Butyl)-5-(5-phenyl-4-((pyridin-2-ylmethyl)amino)phthalazin-1-yl)pyridine-3-sulfonamide (0.0300 g, 0.0570 mmol) was dissolved in TFA (5.00 mL, 64.9 mmol) and stirred at room temperature for 12 h. TFA was removed under reduced pressure and reaction mixture was diluted with saturated NaHCO$_3$ (50 mL). The reaction mixture was extracted with EtOAc (3×30 mL). The combined organic extracts were dried over anhydrous Na$_2$SO$_4$, filtered and concentrated under reduced pressure. The resulting residue was purified by preparative HPLC (Condition 16 as described in general methods) to afford 5-(5-phenyl-4-((pyridin-2-ylmethyl)amino)phthalazin-1-yl)pyridine-3-sulfonamide (10.0 mg, 37.3%) as a white solid. LCMS (Condition 4): retention time 2.25 min, [M+1]=469.2. HPLC (Condition 28): retention time=5.73 min, purity 99.07%. $^1$H NMR (400 MHz, CD$_3$OD) δ 4.68 (s, 2 H), 7.24 (dd, J=4.8 Hz, J=7.6 Hz, 1 H), 7.27 (d, J=7.6 Hz, 1 H), 7.52 (br s, 5 H), 7.71-7.77 (m, 2 H), 7.88 (dd, J=1.6 Hz, J=8.4 Hz, 1 H), 7.95 (dd, J=7.2 Hz, J=8.4 Hz, 1 H), 8.30-8.31 (m, 1 H), 8.57 (dd, J=2.0 Hz, J=2.4 Hz, 1 H), 9.07 (d, J=2.0 Hz, 1 H), 9.21 (d, J=2.4 Hz, 1 H).

Example 2

N-(5-(4-(Benzylamino)-5-phenylphthalazin-1-yl)pyridin-3-yl)acetamide

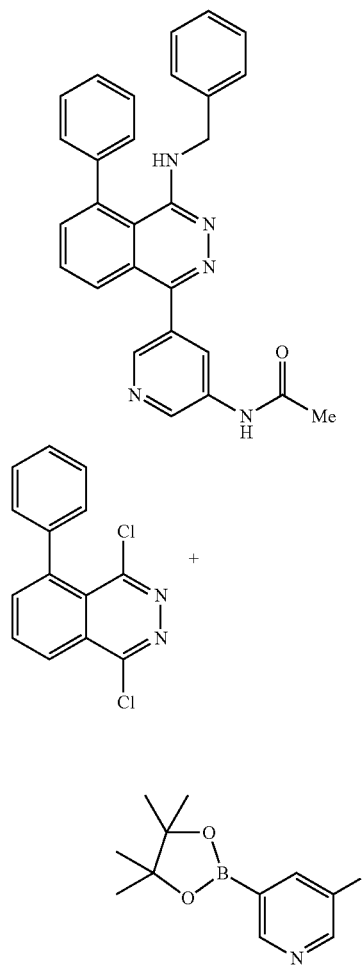

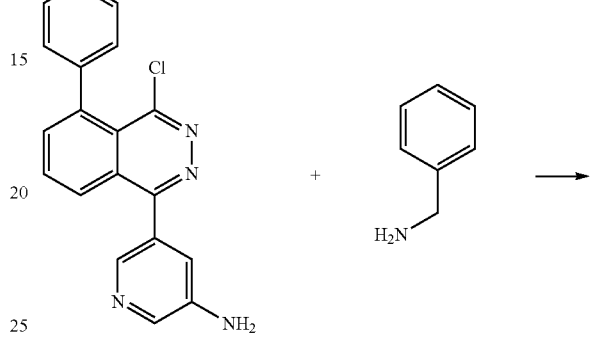

5-(4-Chloro-5-phenylphthalazin-1-yl)pyridin-3-amine (0.800 g, 66.1% yield) was prepared from 1,4-dichloro-5-phenylphthalazine (1.00 g, 3.63 mmol), 5-(4,4,5,5-tetramethyl-1,3,2-dioxaborolan-2-yl)pyridin-3-amine (0.960 g, 4.36 mmol, commercial), $K_3PO_4$ (0.772 g, 3.63 mmol), $Pd_2(dba)_3$ (0.0330 g, 0.0360 mmol) and tricyclohexylphosphine (0.0200 g, 0.0730 mmol) by the methods described for the preparation of N-(tert-butyl)-5-(4-chloro-5-phenylphthalazin-1-yl)pyridine-3-sulfonamide in Example 1. The crude residue was taken to the next step without further purification. LCMS (Condition 11): retention time 0.86 min, [M+1]=333.1.

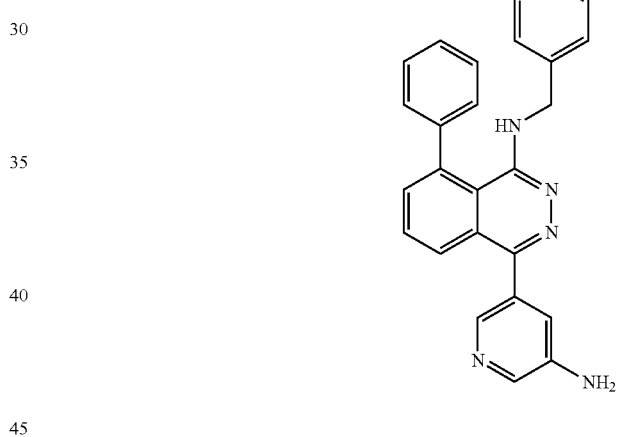

4-(5-Aminopyridin-3-yl)-N-benzyl-8-phenylphthalazin-1-amine (0.300 g, 30.9% yield, white solid) was prepared from 5-(4-chloro-5-phenylphthalazin-1-yl)pyridin-3-amine (0.800 g, 2.40 mmol) and benzylamine (10.0 mL, 92.0 mmol) by the methods described for the preparation of N-(tert-butyl)-5-(5-phenyl-4-((pyridin-2-ylmethyl)amino)phthalazin-1-yl)pyridine-3-sulfonamide in Example 1. The residue was purified by combiflash (REDISEP®, silica gel, 12 g, 8% MeOH/CHCl$_3$). The resulting residue was further purified by preparative HPLC (Condition 21 as described in general methods). LCMS (Condition 5): retention time 2.03 min, [M+1]=404.6. HPLC (Condition 28): retention time=5.47 min, purity 97.63%. $^1$H NMR (400 MHz, DMSO-d$_6$) δ 4.49 (d, J=5.2 Hz, 2 H), 4.99 (t, J=5.2 Hz, 1 H), 5.52 (s, 2 H), 7.01-7.03 (m, 2 H), 7.15-7.28 (m, 4 H), 7.43-7.50 (m, 5 H), 7.66 (dd, J=2.0 Hz, J=6.4 Hz, 1 H), 7.85-7.90 (m, 2 H), 7.94 (d, J=2.0 Hz, 1 H), 8.09 (d, J=2.0 Hz, 1 H).

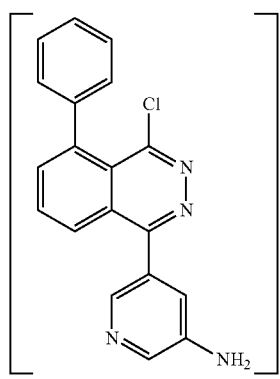

Example 3

N-(5-(4-(Benzylamino)-5-phenylphthalazin-1-yl)pyridin-3-yl)methanesulfonamide

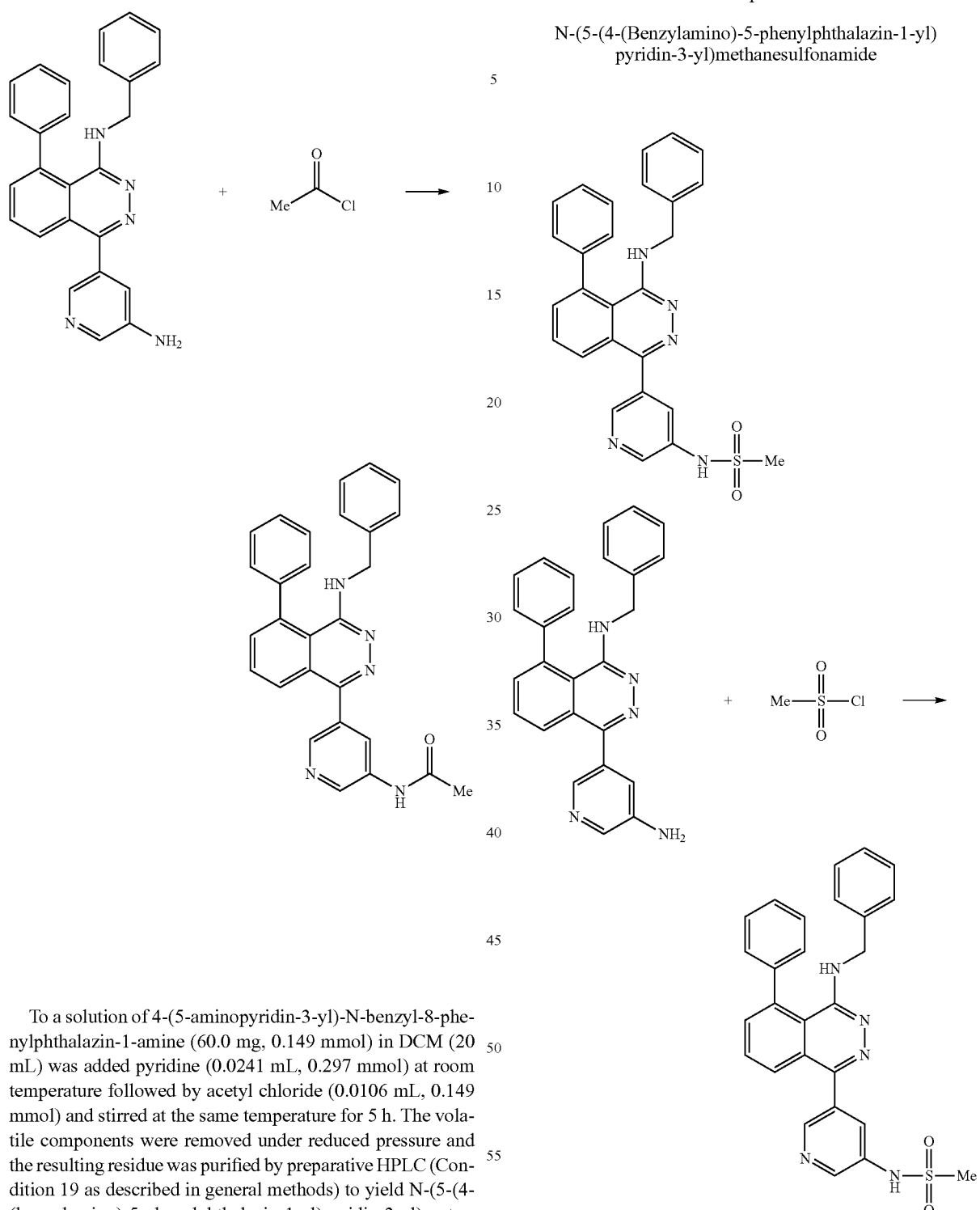

To a solution of 4-(5-aminopyridin-3-yl)-N-benzyl-8-phenylphthalazin-1-amine (60.0 mg, 0.149 mmol) in DCM (20 mL) was added pyridine (0.0241 mL, 0.297 mmol) at room temperature followed by acetyl chloride (0.0106 mL, 0.149 mmol) and stirred at the same temperature for 5 h. The volatile components were removed under reduced pressure and the resulting residue was purified by preparative HPLC (Condition 19 as described in general methods) to yield N-(5-(4-(benzylamino)-5-phenylphthalazin-1-yl)pyridin-3-yl)acetamide (45.0 mg, 67.9%) as a white solid. LCMS (Condition 4): retention time 2.44 min, [M+1]=446.2. HPLC (Condition 28): retention time=6.44 min, purity 97.94%. $^1$H NMR (400 MHz, DMSO-d$_6$) δ 2.13 (s, 3 H), 4.51 (d, J=4.8 Hz, 2 H), 5.06 (dd, J=4.8 Hz, J=5.2 Hz, 1 H), 7.02-7.04 (m, 2 H), 7.23-7.29 (m, 3 H), 7.42-7.52 (m, 5 H), 7.68 (dd, J=1.6 Hz, J=7.2 Hz, 1 H), 7.85-7.93 (m, 2 H), 8.36 (dd, J=2.0 Hz, J=2.4 Hz, 1 H), 8.52 (d, J=2.0 Hz, 1 H), 8.84 (d, J=2.0 Hz, 1 H), 10.37 (s, 1 H).

To a solution of 4-(5-aminopyridin-3-yl)-N-benzyl-8-phenylphthalazin-1-amine (60.0 mg, 0.149 mmol) in DCM (20 mL) was added pyridine (0.0241 mL, 0.297 mmol) at room temperature followed by methanesulfonyl chloride (0.0120 mL, 0.149 mmol) and the reaction mixture stirred for 5 h. The volatile components were removed under reduced pressure and the resulting residue was purified by preparative HPLC (Condition 22 as described in general methods) to obtain N-(5-(4-(benzylamino)-5-phenylphthalazin-1-yl)pyridin-3-yl)methanesulfonamide (50.0 mg, 69.8%) as a white solid. LCMS (Condition 4): retention time 2.45 min, [M+1]=482.2. HPLC (Condition 28): retention time=6.83 min, purity 97.53%. $^1$H NMR (400 MHz, DMSO-$d_6$) δ 2.97 (s, 3 H), 4.51 (d, J=4.8 Hz, 2 H), 5.06 (t, J=4.8 Hz, 1 H), 7.02-7.03 (m, 2 H), 7.22-7.28 (m, 3 H), 7.43-7.52 (m, 5 H), 7.68 (dd, J=2.4 Hz, J=5.6 Hz, 1 H), 7.72 (br s, 1 H), 7.87-7.90 (m, 2 H), 8.35 (br s, 1 H), 8.40 (d, J=1.6 Hz, 1 H), 10.25 (br s, 1 H).

Example 4

Isopropyl 5-(4-(benzylamino)-5-phenylphthalazin-1-yl)pyridin-3-yl)carbamate

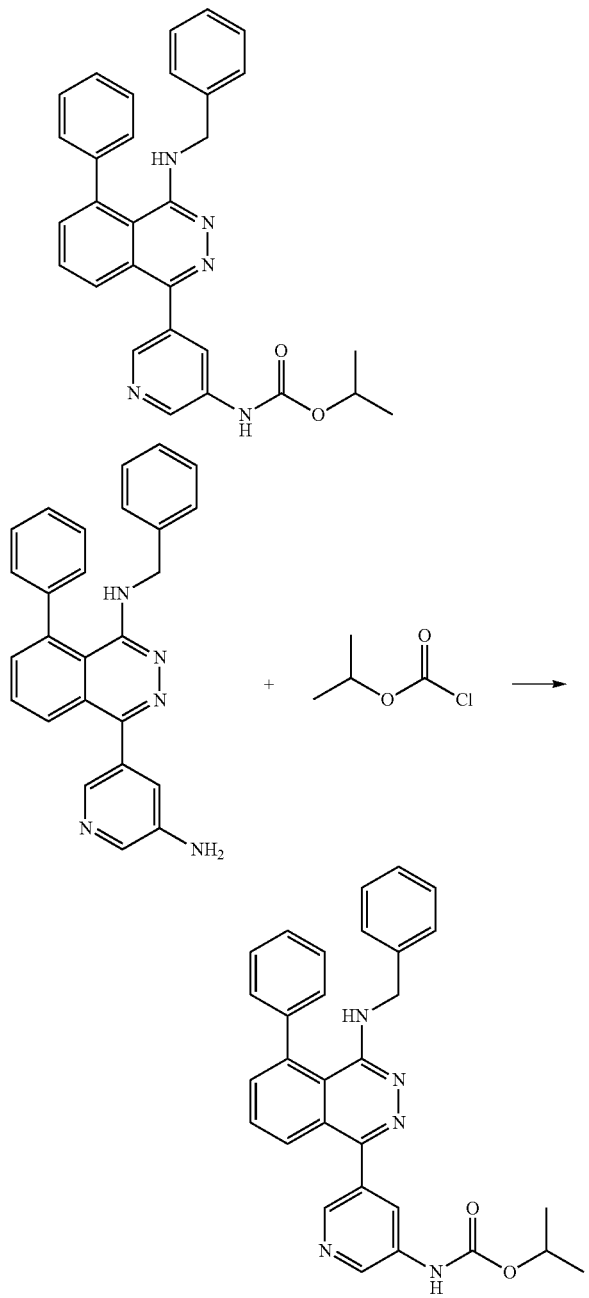

To a solution of 4-(5-aminopyridin-3-yl)-N-benzyl-8-phenylphthalazin-1-amine (60.0 mg, 0.149 mmol) in DCM (20 mL) was added pyridine (0.241 mL, 0.297 mmol) at room temperature followed by isopropyl carbonochloridate (18.2 mg, 0.149 mmol) and the reaction mixture stirred for 5 h. The volatile components were removed under reduced pressure and the resulting residue was purified by preparative HPLC (Condition 23 as described in general methods) to afford isopropyl (5-(4-(benzylamino)-5-phenylphthalazin-1-yl)pyridin-3-yl)carbamate (50.0 mg, 68.7%) as a white solid. LCMS (Condition 4): retention time 2.60 min, [M+1]=490.2. HPLC (Condition 28): retention time=7.65 min, purity 99.27%. $^1$H NMR (400 MHz, DMSO-$d_6$) δ 1.29 (d, J=6.4 Hz, 6 H), 4.51 (d, J=4.8 Hz, 2 H), 4.93 (sept, J=6.4 Hz, 1 H), 5.06 (dd, J=4.8 Hz, J=5.2 Hz, 1 H), 7.01-7.03 (m, 2 H), 7.21-7.28 (m, 3 H), 7.42-7.52 (m, 5 H), 7.69 (dd, J=1.2 Hz, J=6.8 Hz, 1 H), 7.85-7.93 (m, 2 H), 8.16 (br s, 1 H), 8.47 (d, J=1.6 Hz, 1 H), 8.80 (d, J=2.4 Hz, 1 H), 10.00 (s, 1 H).

Example 5

5-(5-Phenyl-4-(pyridin-2-ylmethylamino)phthalazin-1-yl)nicotinamide

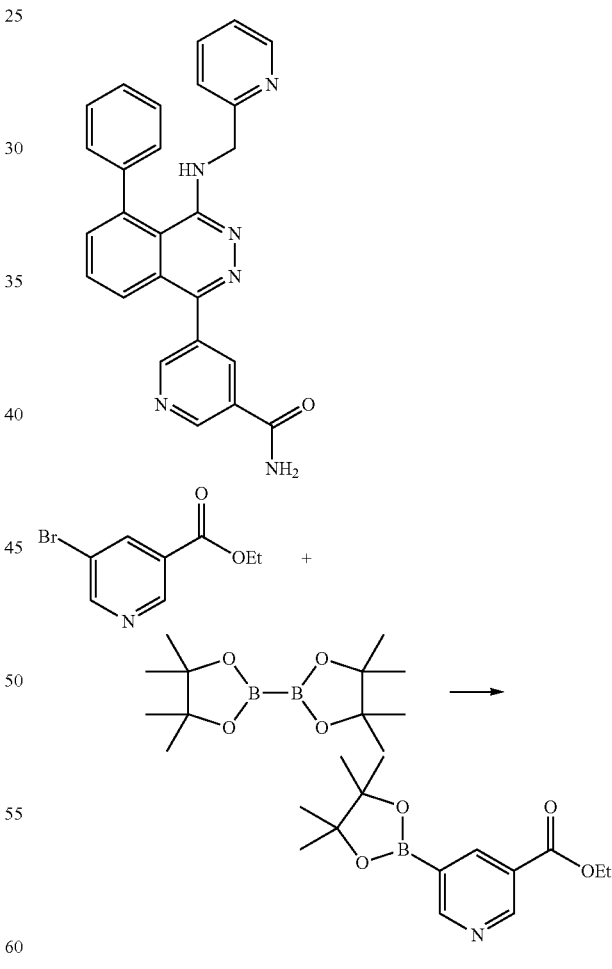

To a solution of 4,4,5,5-tetramethyl-2-(4,4,5,5-tetramethyl (1,3,2-dioxaborolan-2-yl))-1,3,2-dioxaborolane (1.54 g, 6.09 mmol) and tricyclohexylphosphonium tetrafluoroborate (0.112 g, 0.304) in 1,4-dioxane (20 mL) at ambient temperature was added KOAc (1.71 g, 17.4 mmol) and the reaction mixture was purged with nitrogen gas for 10 min. The reaction mixture was heated to 80° C. Pd$_2$(dba)$_3$ (0.199 g, 0.217 mmol) was added to the reaction mixture and the resulting reaction mixture purged with nitrogen for 10 min at 80° C. The reaction mixture was heated to 90° C. and a solution of ethyl 5-bromonicotinate (1.00 g, 4.35 mmol) in 1,4-dioxane (5 mL) was added. The resulting mixture was stirred at 100° C. for 16 h. The reaction mixture was allowed to cool to ambient temperature, filtered through CELITE® and the filtrate was concentrated under reduced pressure to obtain ethyl 5-(4,4,5,5-tetramethyl-1,3,2-dioxaborolan-2-yl)nicotinate (1.50 g). The residue was taken to the next step without further purification. LCMS (Condition 11): retention time 0.52 min, [M+1]=196.1. $^1$H NMR (400 MHz, DMSO-d$_6$) δ 1.16 (s, 12 H), 1.35 (t, J=7.2 Hz, 3 H), 4.36 (q, J=7.2 Hz, 2 H), 8.43 (dd, J=1.6 Hz, J=2.0 Hz, 1 H), 8.95 (d, J=1.6 Hz, 1 H), 9.16 (br s, 1 H).

The combined organic extracts were dried over anhydrous Na$_2$SO$_4$, filtered and concentrated under reduced pressure. The residue was triturated with EtOAc to afford ethyl 5-(4-hydroxy-5-phenylphthalazin-1-yl)nicotinate (3.50 g, 44.1%) as an off-white solid which is 85% pure by LC-MS. LCMS (Condition 1): retention time 2.52 min, [M+1]=372.0. $^1$H NMR (400 MHz, DMSO-d$_6$) δ 1.37 (t, J=7.2 Hz, 3 H), 4.41 (q, J=7.2 Hz, 2 H), 7.33-7.42 (m, 5 H), 7.62-7.65 (m, 2 H), 7.92 (dd, J=7.6 Hz, J=8.0 Hz, 1 H), 8.49 (t, J=2.0 Hz, 1 H), 9.07 (d, J=2.0 Hz, 1 H), 9.25 (d, J=2.0 Hz, 1 H), 12.74 (br s, 1 H).

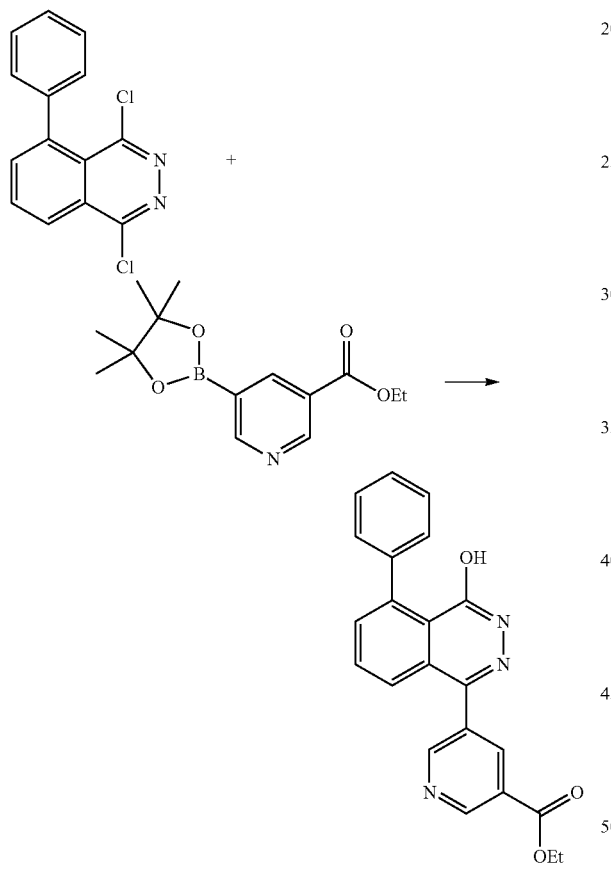

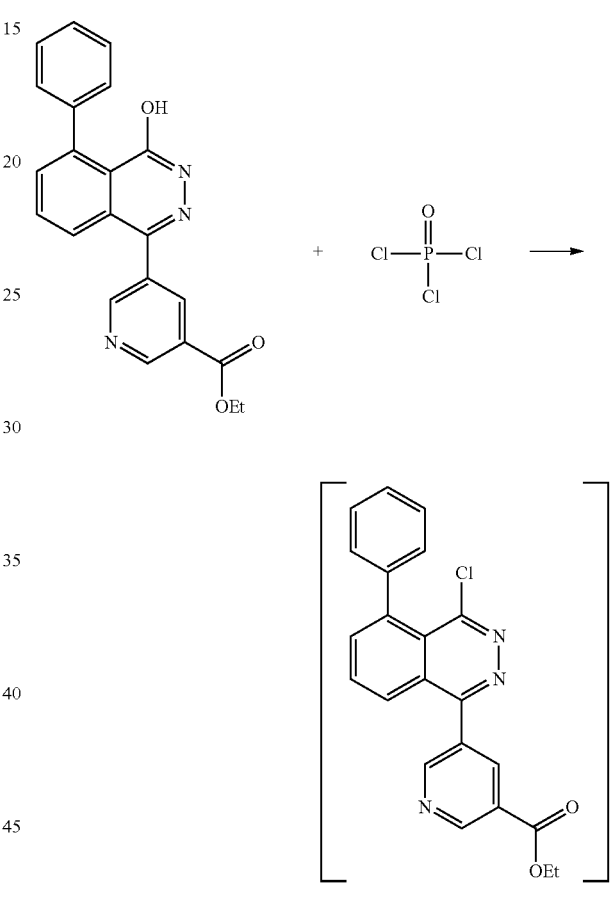

To a solution of 1,4-dichloro-5-phenylphthalazine (5.00 g, 18.2 mmol) in 1,4-dioxane (50 mL) and water (9 mL) was added ethyl 5-(4,4,5,5-tetramethyl-1,3,2-dioxaborolan-2-yl) nicotinate (5.32 g, 27.3 mmol), and K$_3$PO$_4$ (7.72 g, 36.3 mmol). The contents were purged with nitrogen for 10 min. Tricyclohexylphosphonium tetrafluoroborate (0.402 g, 1.09 mmol) was added followed by Pd$_2$(dba)$_3$ (0.416 g, 0.454 mmol) and the reaction mixture was heated at 95° C. for 12 h. The reaction mixture was allowed to cool to ambient temperature and diluted with HCOONH$_4$ buffer (pH~5) solution. The reaction mixture was extracted with EtOAc (3×75 mL).

To a solution of ethyl 5-(4-hydroxy-5-phenylphthalazin-1-yl)nicotinate (3.50 g, 9.42 mmol) in toluene (35 mL) was added POCl$_3$ (26.4 mL, 283 mmol) followed by N,N-dimethylbenzenamine (1.5 mL, 9.42 mmol). The resulting mixture was heated in a sealed tube at 100° C. for 12 h. The reaction mixture was allowed to cool to room temperature and concentrated under reduced pressure. The residue was dissolved in EtOAc (200 mL) and washed with saturated NaHCO$_3$ (2×50 mL) solution. The combined organic extracts were dried over anhydrous Na$_2$SO$_4$, filtered and concentrated under reduced pressure to yield ethyl 5-(4-chloro-5-phenylphthalazin-1-yl)nicotinate (3.50 g) as a yellow solid with LC-MS purity of 47% which was taken for the next step without further purification. LCMS (Condition 12): retention time 0.97 min, [M+1]=390.0.

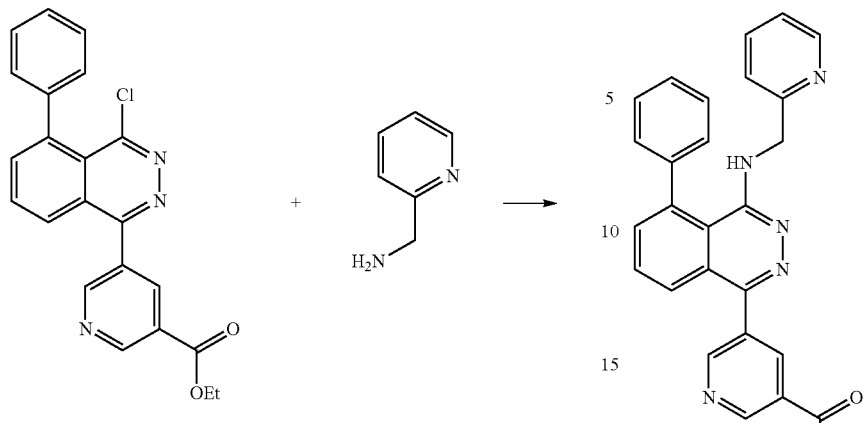

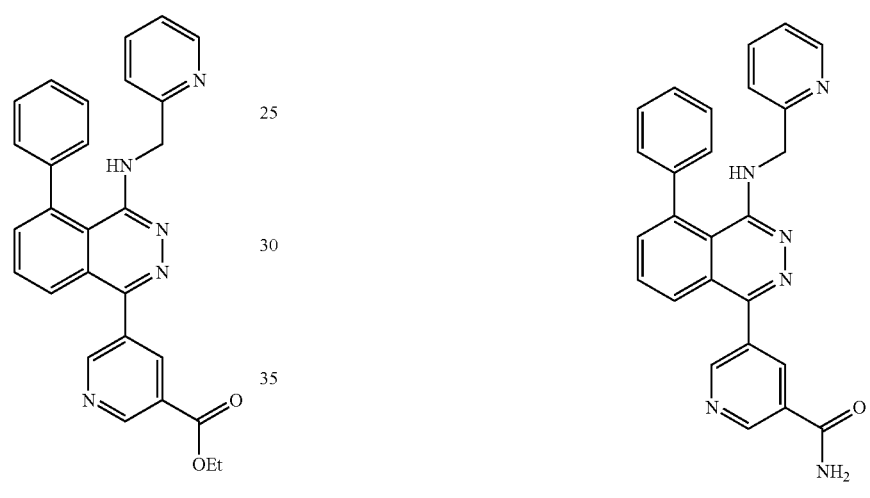

Ethyl 5-(5-phenyl-4-((pyridin-2-ylmethyl)amino)phthalazin-1-yl)nicotinate (3.10 g, 88.0%, brown solid) was prepared from 5-(4-chloro-5-phenylphthalazin-1-yl)nicotinate (3.00 g, 7.70 mmol) and 2-(aminomethyl)pyridine (10.0 mL, 97.0 mmol) by the methods described for the preparation of N-(tert-butyl)-5-(5-phenyl-4-((pyridin-2-ylmethyl)amino)phthalazin-1-yl)pyridine-3-sulfonamide in Example 1. The residue was purified by preparative HPLC (Condition 15 as described in general methods). LCMS (Condition 2): retention time 1.90 min, [M+1]=462.2. HPLC (Condition 25): retention time=7.06 min, purity 96.07%. $^1$H NMR (400 MHz, DMSO-$d_6$) δ 1.38 (t, J=7.2 Hz, 3 H), 4.42 (q, J=7.2 Hz, 2 H), 4.67 (d, J=4.4 Hz, 2 H), 6.35 (dd, J=4.0 Hz, J=4.4 Hz, 1 H), 7.21-7.25 (m, 1 H), 7.28 (d, J=8.0 Hz, 1 H), 7.50-7.61 (m, 5 H), 7.69-7.73 (m, 2 H), 7.84 (dd, J=1.6 Hz, J=8.4 Hz, 1 H), 7.93 (dd, J=7.2 Hz, J=8.4 Hz, 1 H), 8.23 (dt, J=0.8 Hz, J=4.8 Hz, 1 H), 8.53 (t, J=2.0 Hz, 1 H), 9.11 (d, J=2.0 Hz, 1 H), 9.24 (d, J=2.0 Hz, 1 H).

A solution of ethyl 5-(5-phenyl-4-((pyridin-2-ylmethyl)amino)phthalazin-1-yl)nicotinate (230 mg, 0.288 mmol) in MeOH (5 mL) was purged with ammonia gas for 5 minutes at −10° C. The reaction mixture was heated in a sealed tube at 70° C. for 12 h. The volatile components were removed under reduced pressure and the resulting residue was purified by HPLC (Condition 20 as described in general methods) to afford 5-(5-phenyl-4-((pyridin-2-ylmethyl)amino)phthalazin-1-yl)nicotinamide (50.0 mg, 39.8%) as a yellow solid. LCMS (Condition 2): retention time 1.90 min, [M+1]= 433.0. HPLC (Condition 25): retention time=5.20 min, purity 98.63%. $^1$H NMR (400 MHz, DMSO-$d_6$) δ 4.66 (d, J=4.0 Hz, 2 H), 6.32 (dd, J=4.0 Hz, J=4.4 Hz, 1 H), 7.22-7.24 (m, 1 H), 7.28 (d, J=7.6 Hz, 1 H), 7.51-7.60 (m, 5 H), 7.68-7.73 (m, 3 H), 7.84 (dd, J=1.2 Hz, J=8.4 Hz, 1 H), 7.93 (dd, J=7.2 Hz, J=8.4 Hz, 1 H), 8.22-8.24 (m, 1 H), 8.28 (br s, 1 H), 8.51 (t, J=2.0 Hz, 1 H), 8.99 (d, J=2.0 Hz, 1H), 9.18 (d, J=2.0 Hz, 1 H).

Example 6

N-(2,3-Dihydroxypropyl)-5-(5-phenyl-4-(pyridin-2-ylmethylamino)phthalazin-1-yl)nicotinamide

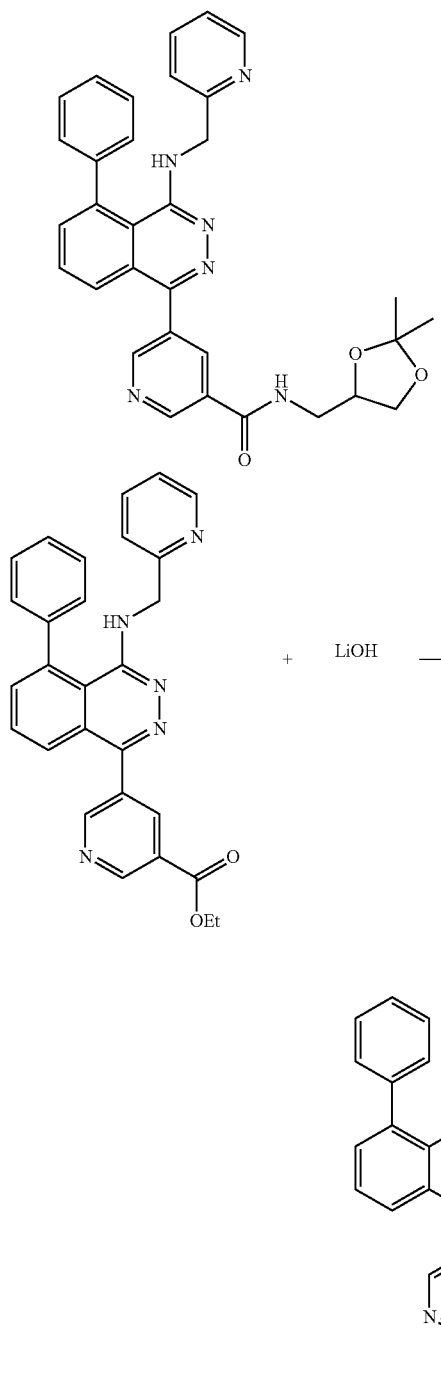

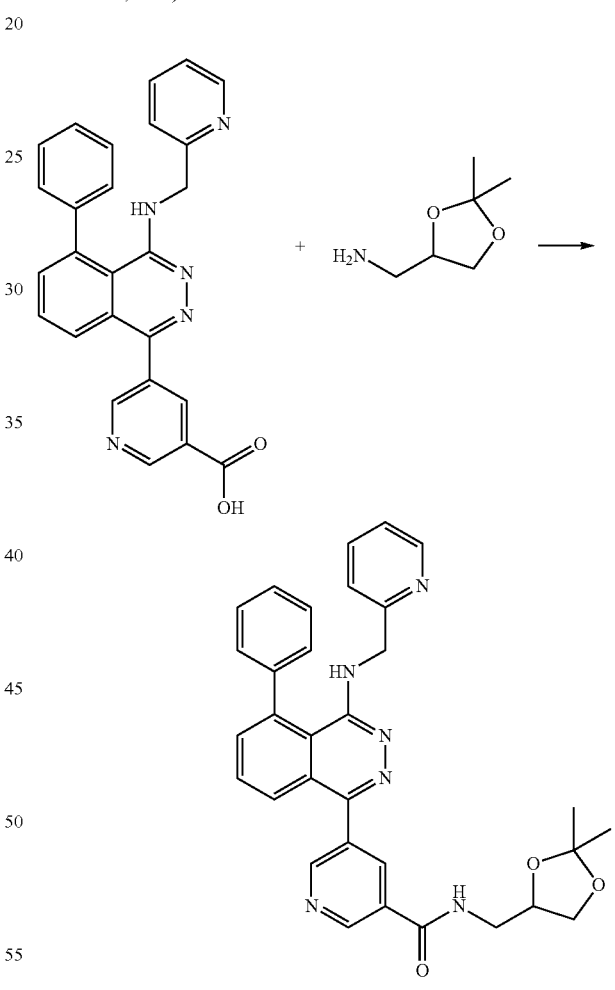

To a solution of ethyl 5-(5-phenyl-4-((pyridin-2-ylmethyl)amino)phthalazin-1-yl)nicotinate (0.120 g, 0.260 mmol) in EtOH (6 mL) and THF (6 mL) was added LiOH (0.0620 g, 2.60 mmol) in water (3 mL) at room temperature. The reaction mixture was stirred at the same temperature for 16 h. Then the reaction mixture was concentrated under reduced pressure and the resulting residue was diluted with water (5 mL). The reaction mixture was extracted with EtOAc and the aqueous layer was separated. The aqueous layer was acidified to pH 5 with citric acid and extracted with EtOAc. The organic extract was dried over anhydrous $Na_2SO_4$, filtered and concentrated under reduced pressure. The resulting residue was purified by HPLC (Condition 13 as described in general methods) to afford 5-(5-phenyl-4-((pyridin-2-ylmethyl)amino)phthalazin-1-yl)nicotinic acid (0.0150 g, 13.3%). LCMS (Condition 2): retention time 1.54 min, [M-1]=432.0. HPLC (Condition 25): retention time=5.86 min, purity 95.51%. $^1$H NMR (400 MHz, DMSO-$d_6$) δ 4.66 (d, J=4.4 Hz, 2 H), 6.25 (dd, J=4.0 Hz, J=4.4 Hz, 1 H), 7.20-7.24 (m, 1 H), 7.28 (d, J=7.6 Hz, 1 H), 7.52-7.59 (m, 5 H), 7.68-7.73 (m, 2 H), 7.82 (dd, J=1.2 Hz, J=8.4 Hz, 1 H), 7.91 (dd, J=7.2 Hz, J=8.4 Hz, 1 H), 8.22-8.25 (m, 1 H), 8.35 (dd, J=1.6 Hz, J=2.0 Hz, 1 H), 8.74 (d, J=2.0 Hz, 1 H), 9.09 (d, J=1.6 Hz, 1 H).

To a solution of 5-(5-phenyl-4-((pyridin-2-ylmethyl)amino)phthalazin-1-yl)nicotinic acid (0.200 g, 0.461 mmol) in DMF (5 mL) was added HATU (0.526 g, 1.38 mmol) at ambient temperature. DMAP (0.169 g, 1.38 mmol) was added followed by (2,2-dimethyl-1,3-dioxolan-4-yl)methanamine (0.0610 g, 0.461 mmol, commercial) and the contents were stirred at ambient temperature for 16 h. The reaction mixture was concentrated under reduced pressure and the residue was diluted with water. The reaction mixture was extracted with EtOAc. The organic layer was dried over anhydrous Na$_2$SO$_4$, filtered and concentrated under reduced pressure. The resulting residue was purified by combiflash (REDISEP®, silica gel, 12 g, 50% EtOAc/hexanes) to obtain N-((2,2-dimethyl-1,3-dioxolan-4-yl)methyl)-5-(5-phenyl-4-((pyridin-2-ylmethyl)amino) phthalazin-1-yl)nicotinamide (0.0300 g, 11.9%) as an off-white solid. LCMS (Condition 7): retention time 1.76 min, [M+1]=547.2. HPLC (Condition 24): retention time 7.68 min, Purity 96.10%. $^1$H NMR (400 MHz, DMSO-d$_6$) δ 1.27 (s, 3H), 1.36 (s, 3 H), 3.31-3.51 (m, 2 H), 3.74 (dd, J=5.6 Hz, J=8.4 Hz, 1 H), 4.03 (dd, J=6.0 Hz, J=8.4 Hz, 1 H), 4.26 (m, 1 H), 4.66 (d, J=4.0 Hz, 2 H), 6.33 (dd, J=4.0 Hz, J=4.4 Hz, 1 H), 7.22 (dd, J=5.2 Hz, J=6.4 Hz, 1 H), 7.29 (d, J=6.8 Hz, 1 H), 7.50-7.59 (m, 5 H), 7.69-7.73 (m, 2 H), 7.84 (dd, J=1.6 Hz, J=8.0 Hz, 1 H), 7.93 (dd, J=7.2 Hz, J=8.0 Hz, 1 H), 8.23 (d, J=4.8 Hz, 1 H), 8.51 (t, J=2.0 Hz, 1 H), 8.94 (dd, J=5.6 Hz, J=6.0 Hz, 1 H), 9.0 (d, J=2.0 Hz, 1H), 9.16 (d, J=2.0 Hz, 1 H).

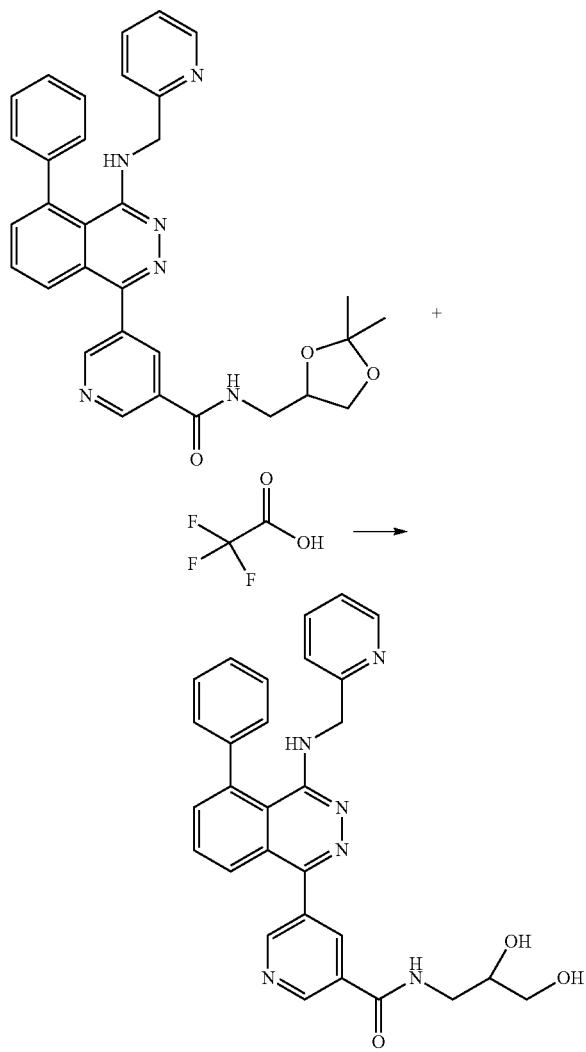

To N-((2,2-dimethyl-1,3-dioxolan-4-yl)methyl)-5-(5-phenyl-4-((pyridin-2ylmethyl)amino)phthalazin-1-yl)nicotinamide (0.0200 g, 0.0370 mmol) was added TFA (0.00282 mL, 0.0370 mmol) at room temperature and was heated at 50° C. for 4 h. TFA was removed under reduced pressure and reaction mixture was diluted with saturated NaHCO$_3$ (50 mL). The reaction mixture was extracted with EtOAc (3×30 mL). The combined organic extracts were dried over anhydrous Na$_2$SO$_4$, filtered and concentrated under reduced pressure. The resulting residue was purified by preparative HPLC (Condition 14 as described in general methods) to afford N-(2,3-dihydroxypropyl)-5-(5-phenyl-4-((pyridin-2-ylmethyl)amino)phthalazin-1-yl)nicotinamide (0.0120 g, 65%). LCMS (Condition 7): retention time 1.59 min, [M+1]=507.2. HPLC (Condition 25): retention time 5.23 min, Purity 97.90%. $^1$H NMR (400 MHz, DMSO-d$_6$) δ 3.21-3.49 (m, 4 H), 3.63-3.72 (m, 1 H), 4.55-4.60 (m, 1 H), 4.66 (d, J=4.0 Hz, 2 H), 4.84 (br s, 1 H), 6.32 (dd, J=4.0 Hz, J=4.4 Hz, 1 H), 7.22 (dd, J=4.8 Hz, J=6.8 Hz, 1 H), 7.28 (d, J=8.0 Hz, 1 H), 7.50-7.58 (m, 5 H), 7.68-7.73 (m, 2 H), 7.80 (dd, J=1.6 Hz, J=8.4 Hz, 1 H), 7.93 (dd, J=7.2 Hz, J=8.4 Hz, 1 H), 8.23 (d, J=4.8 Hz, 1 H), 8.51 (t, J=2.0 Hz, 1 H), 8.75 (t, J=5.6 Hz, 1 H), 8.98 (d, J=2.0 Hz, 1 H), 9.16 (d, J=2.0 Hz, 1 H).

Example 7

1-(5-(5-Phenyl-4-(pyridin-2-ylmethylamino)phthalazin-1-yl)pyridin-3-yl)ethane-1,2-diol

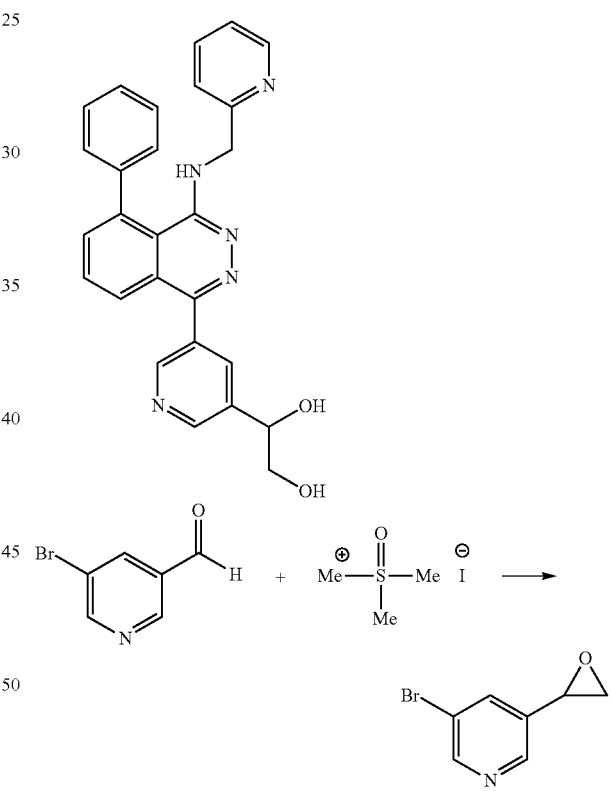

To a solution of trimethylsulfoxonium iodide (7.10 g, 32.3 mmol) in DMSO (25 mL) was added NaH (95%, 0.774 g, 32.3 mmol) portionwise at ambient temperature followed by dropwise addition of 5-bromonicotinaldehyde (3.00 g, 16.1 mmol) in DMSO (15 mL) over 15 min. The reaction mixture was quenched by the addition of ice cold water (200 mL) and the resulting mixture extracted with EtOAc (2×150 mL). The combined organic extracts were dried over anhydrous Na$_2$SO$_4$, filtered and concentrated under reduced pressure. The resulting residue was purified by combiflash (REDISEP®, silica gel, 40 g, 25% EtOAc/hexanes) to obtain 3-bromo-5-(oxiran-2-yl)pyridine (1.00 g, 31.0%) as a pale yellow liquid. LCMS (Condition 8): retention time 1.83 min, [M+2]=202.2. ¹H NMR (400 MHz, CDCl₃) δ 2.79 (dd, J=2.4 Hz, J=5.2 Hz, 1 H), 3.20 (dd, J=4.0 Hz, J=5.2 Hz, 1 H), 3.87 (dd, J=2.4 Hz, J=4.0 Hz, 1 H), 7.69 (dd, J=1.6 Hz, J=2.0 Hz, 1 H), 8.50 (d, J=1.6 Hz, 1 H), 8.62 (d, J=2.0 Hz, 1 H).

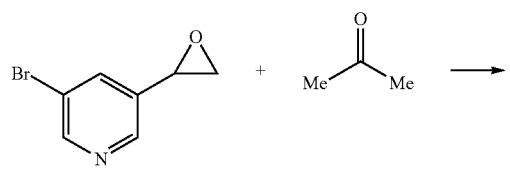

To a solution of 3-bromo-5-(oxiran-2-yl)pyridine (1.00 g, 5.00 mmol) in acetone (25 mL) was added BF₃.OEt₂ (0.950 mL, 7.50 mmol) dropwise at ambient temperature and the reaction mixture was stirred for 14 h. The reaction mixture was diluted with water (15 mL) and extracted with EtOAc (2×50 mL). The combined organic extracts were dried over anhydrous Na₂SO₄, filtered and evaporated under reduced pressure. The resulting residue was purified by combiflash (REDISEP®, silica gel, 40 g, 25% EtOAc/hexanes) to obtain 3-bromo-5-(2,2-dimethyl-1,3-dioxolan-4-yl)pyridine (0.700 g, 54.2%) as a pale yellow liquid. LCMS (Condition 8): retention time 2.17 min, [M+2]=260.0. ¹H NMR (400 MHz, CDCl₃) δ 1.48 (s, 3 H), 1.55 (s, 3 H), 3.72 (dd, J=7.6 Hz, J=8.4 Hz, 1 H), 4.36 (dd, J=6.4 Hz, J=8.4 Hz, 1 H), 5.08 (dd, J=6.4 Hz, J=7.6 Hz, 1 H), 7.85-7.86 (m, 1 H), 8.49 (d, J=1.6 Hz, 1 H), 8.62 (d, J=2.0 Hz, 1 H).

A solution of 3-bromo-5-(2,2-dimethyl-1,3-dioxolan-4-yl)pyridine (100 mg, 0.387 mmol), bis(pinacolato)diboron (148 mg, 0.581 mmol) and KOAc (114 mg, 1.16 mmol) in 1,4-dioxane (10 mL) was purged with nitrogen for 30 min. Then Pd(dppf)Cl₂—CH₂Cl₂ (32.0 mg, 0.0390 mmol) was added and the reaction mixture was heated in a sealed tube at 100° C. for 14 h. The reaction mixture was allowed to cool to ambient temperature and filtered through CELITE®. The filtrate was concentrated under reduced pressure to yield 3-(2,2-dimethyl-1,3-dioxolan-4-yl)-5-(4,4,5,5-tetramethyl-1,3,2-dioxaborolan-2-yl)pyridine (90.0 mg, 76.0%) as a viscous oil which was used in the next step without further purification. LCMS (Condition 11): retention time 0.95 min, [M+1]=306.1.

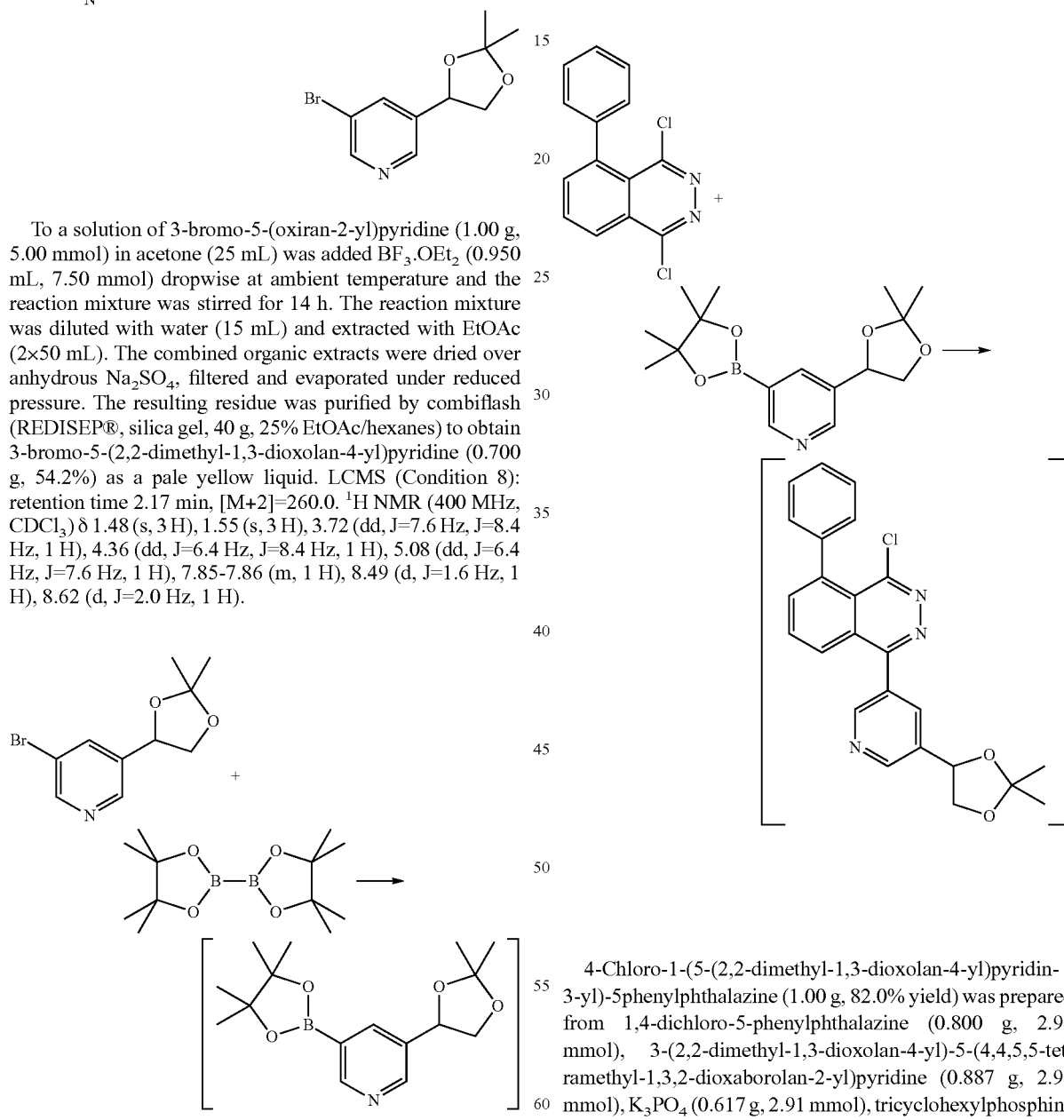

4-Chloro-1-(5-(2,2-dimethyl-1,3-dioxolan-4-yl)pyridin-3-yl)-5phenylphthalazine (1.00 g, 82.0% yield) was prepared from 1,4-dichloro-5-phenylphthalazine (0.800 g, 2.91 mmol), 3-(2,2-dimethyl-1,3-dioxolan-4-yl)-5-(4,4,5,5-tetramethyl-1,3,2-dioxaborolan-2-yl)pyridine (0.887 g, 2.91 mmol), K₃PO₄ (0.617 g, 2.91 mmol), tricyclohexylphosphine (0.0160 g, 0.0580 mmol) and Pd₂(dba)₃ (0.0270 g, 0.0290 mmol) by the methods described for N-(tert-butyl)-5-(4-chloro-5-phenylphthalazin-1-yl)pyridine-3-sulfonamide in Example 1. The crude product was taken to next step without purification. LCMS (Condition 11): retention time 1.05 min, [M+1]=418.1.

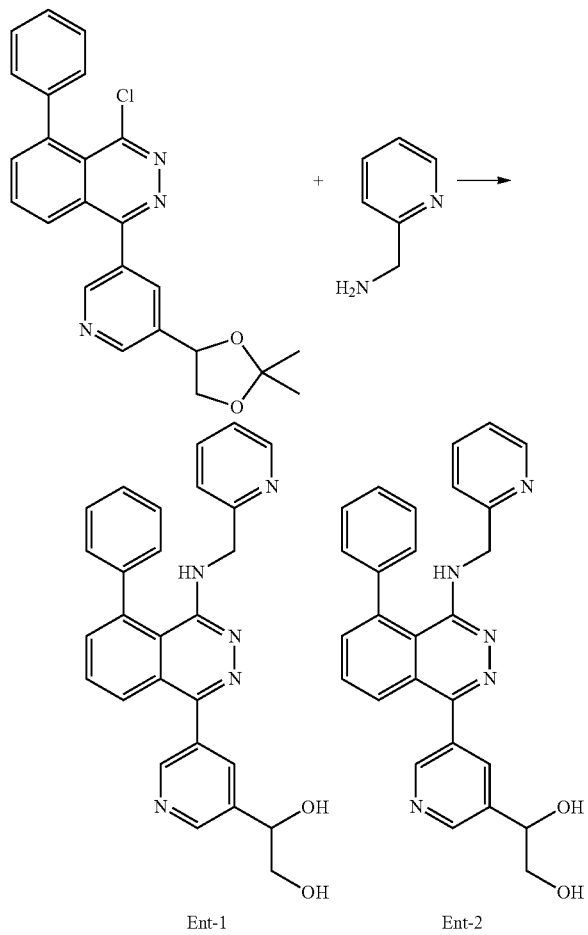

To a solution of 4-chloro-1-(5-(2,2-dimethyl-1,3-dioxolan-4-yl)pyridin-3-yl)-5-phenylphthalazine (1.00 g, 2.39 mmol) in toluene (5 mL) was added pyridin-2-ylmethanamine (5.00 mL, 48.5 mmol) the contents were heated at 100° C. for 12 h. The reaction mixture was diluted with DCM (200 mL) and washed with 1.5N HCl (2 ×20 mL). The organic extract was dried over anhydrous $Na_2SO_4$, filtered and concentrated under reduced pressure. The resulting crude was purified by preparative HPLC (Condition 18 as described in general methods) to obtain 1-(5-(5-phenyl-4-((pyridin-2-ylmethyl)amino)phthalazin-1-yl)pyridin-3-yl)ethane-1,2-diol (55.0 mg, 5.11%) as a white solid. The racemic product (50 mg) was resolved into individual enantiomers by chiral SFC (Condition 29 as described in general methods).

Ent-1:
1-(5-(5-Phenyl-4-((pyridin-2-ylmethyl)amino)phthalazin-1-yl)pyridin-3-yl)ethane-1,2-diol (18.0 mg). Chiral HPLC (Condition 29): retention time 7.38 min, Purity 100%. LCMS (Condition 4): retention time 2.15 min, [M+1]=450.2.

Ent-2:
1-(5-(5-Phenyl-4-((pyridin-2-ylmethyl)amino)phthalazin-1-yl)pyridin-3-yl)ethane-1,2-diol (15.0 mg). Chiral HPLC (Condition 29): retention time 8.83 min, Purity 98.16%. LCMS (Condition 2): retention time 1.65 min, [M+1]=450.2.

$^1$H NMR (400 MHz, DMSO-$d_6$) δ 3.53-3.66 (m, 2 H), 4.65 (d, J=4.4 Hz, 2 H), 4.68-4.75 (m, 1 H), 4.87 (dd, J=5.6 Hz, J=6.0 Hz, 1 H), 5.54 (d, J=4.4 Hz, 1 H), 6.26 (t, J=4.4 Hz, 1 H), 7.18-7.24 (m, 1 H), 7.27 (d, J=8.0 Hz, 1 H), 7.51-7.58 (m, 5 H), 7.68-7.73 (m, 2 H), 7.84-7.93 (m, 2 H), 8.01 (t, J=2.0 Hz, 1 H), 8.23 (dd, J=3.2 Hz, J=4.4 Hz, 1 H), 8.69 (d, J=2.0 Hz, 1 H), 8.73 (d, J=2.0 Hz, 1 H).

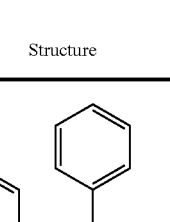

| Ex. No. | Structure | Name | $^1$H NMR | LC/MS Rt (min) Method M + H |
|---|---|---|---|---|
| 8 | 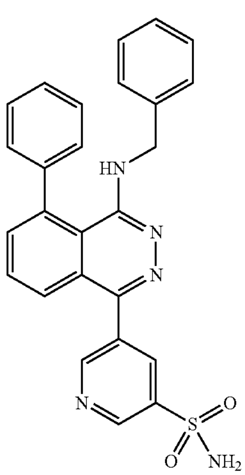 [SMILES: NS(=O)(=O)c1cncc(-c2nnc(NCc3ccccc3)c3c(-c4ccccc4)cccc23)c1] | 5-(4-(Benzylamino)-5-phenylphthalazin-1-yl)pyridine-3-sulfonamide | $^1$H NMR (400 MHz, DMSO-$d_6$) δ 4.53 (d, J = 4.8 Hz, 2 H), 5.15 (t, J = 4.8 Hz, 1 H), 7.02-7.05 (m, 2 H), 7.23-7.29 (m, 3 H), 7.45-7.52 (m, 5 H), 7.72-7.74 (m, 3 H), 7.86 (dd, J = 1.2 Hz, J = 8.4 Hz, 1 H), 7.95 (dd, J = 7.2 Hz, J = 8.4 Hz, 1 H), 8.47 (t, J = 2.0 Hz, 1 H), 9.09 (d, J = 2.0 Hz, 1 H), 9.12 (d, J = 2.0 Hz, 1 H). | 2.27 Condition 466.0 (M − H) |

| Ex. No. | Structure | Name | ¹H NMR | LC/MS Rt (min) Method M + H |
|---|---|---|---|---|
| 9 | 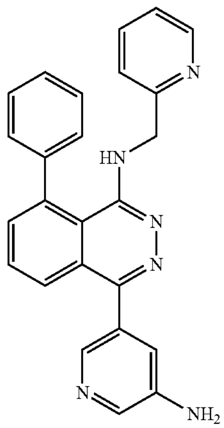 [SMILES: Nc1cncc(-c2nnc(NCc3ccccn3)c3c(-c4ccccc4)cccc23)c1] | 4-(5-Aminopyridin-3-yl)-8-phenyl-N-(pyridin-2-ylmethyl)phthalazin-1-amine | ¹H NMR (400 MHz, DMSO-$d_6$) δ 4.63 (d, J = 4.4 Hz, 2 H), 5.52 (s, 2 H), 6.20 (dd, J = 4.0 Hz, J = 4.4 Hz, 1 H), 7.16 (dd, J = 2.0 Hz, J = 2.4 Hz, 1 H), 7.20-7.23 (m, 1 H), 7.26 (d, J = 7.6 Hz, 1 H), 7.49-7.57 (m, 5 H), 7.65-7.72 (m, 2 H), 7.85-7.92 (m, 2 H), 7.96 (d, J = 2.0 Hz, 1 H), 8.08 (d, J = 2.8 Hz, 1 H), 8.23 (dt, J = 0.8 Hz, J = 4.0 Hz, 1 H). | 2.26 Condition 4 405.2 |

Example 10

1-(5-(4-(Benzylamino)-5-phenylphthalazin-1-yl)pyridin-3-yl)urea

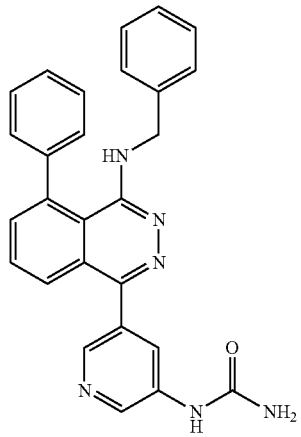

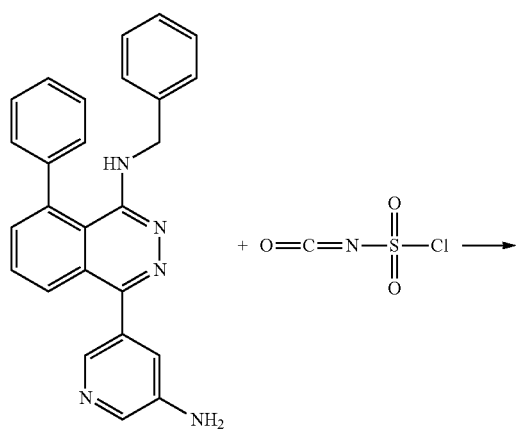

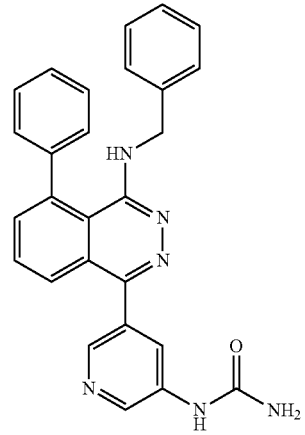

To a solution of 4-(5-aminopyridin-3-yl)-N-benzyl-8-phenylphthalazin-1-amine (60.0 mg, 0.149 mmol) in dichloromethane (10 mL) was added chlorosulfonyl isocyanate (0.0191 mL, 0.223 mmol) dropwise at 0° C. and the reaction mixture allowed to stir for 2 h while warming to ambient temperature. The volatile components were evaporated under reduced pressure and the resulting residue was cooled to 0° C. 1.5N HCl was added and the reaction mixture stirred for an additional 2 h. The reaction mixture was adjusted to pH~8 by the addition of aqueous sodium bicarbonate. The resulting solution was extracted with ethyl acetate (3×5 mL). The combined organic layers were dried over $Na_2SO_4$, filtered and concentrated under reduced pressure. The resulting residue was purified by preparative HPLC (Condition 30 as described in general methods) to afford 1-(5-(4-(benzylamino)-5-phenylphthalazin-1-yl)pyridin-3-yl)urea (2.00 mg, 3.01%) as a white solid. LCMS (Condition 4): retention time 2.32 min, [M+1]=447.2. HPLC (Condition 28): retention time=6.13 min, purity 98.80%. ¹H NMR (400 MHz, DMSO-$d_6$) δ 4.51 (d, J=4.8 Hz, 2 H), 5.04 (t, J=4.8 Hz, 1 H), 6.10 (s, 2 H), 7.02 (dd, J=1.2 Hz, J=6.8 Hz, 2 H), 7.22-7.28 (m, 3 H), 7.43-7.51 (m, 5 H), 7.68 (dd, J=1.2 Hz, J=7.6 Hz, 1 H), 7.85-7.92 (m, 2 H), 8.24 (dd, J=2.0 Hz, J=2.4 Hz, 1 H), 8.37 (d, J=2.0 Hz, 1 H), 8.64 (d, J=2.4 Hz, 1 H), 8.94 (s, 1 H).

Example 11

N-(5-(5-Phenyl-4-(pyridin-2-ylmethylamino)phthalazin-1-yl)pyridin-3-yl)acetamide

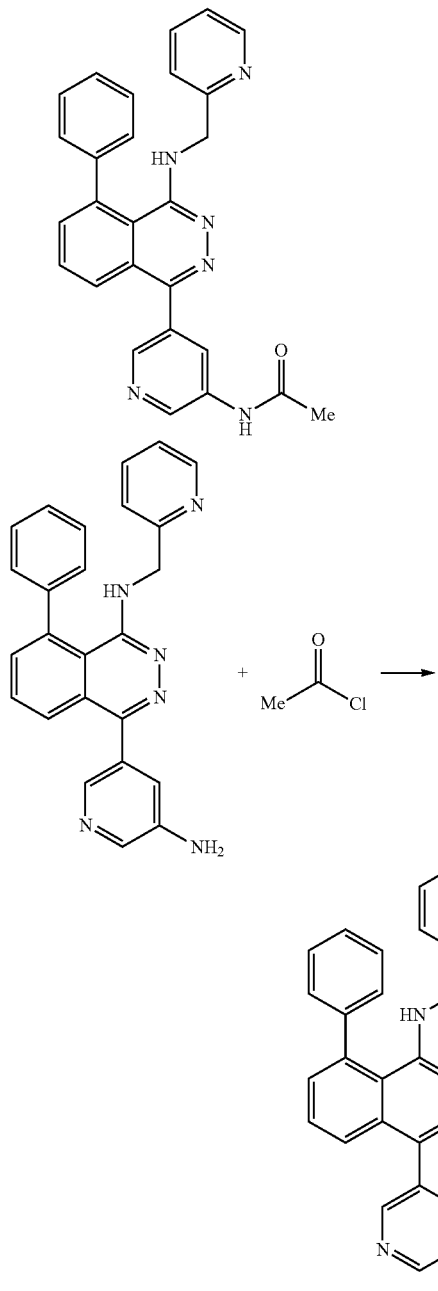

To a solution of 4-(5-aminopyridin-3-yl)-8-phenyl-N-(pyridin-2-ylmethyl)phthalazin-1-amine (50.0 mg, 0.124 mmol) in dichloromethane (5 mL) at ambient temperature was added pyridine (0.0200 mL, 0.247 mmol) followed by acetyl chloride (0.0132 mL, 0.185 mmol). After stirring for 5 h at room temperature, the reaction mixture was diluted with dichloromethane (50 mL) and the organic portion washed with water (10 mL) followed by brine (10 mL). The organic layer was dried over $Na_2SO_4$, filtered and concentrated under reduced pressure. The resulting residue was purified by preparative HPLC (Condition 31 as described in general methods) to obtain N-(5-(5-phenyl-4-((pyridin-2-ylmethyl)amino)phthalazin-1-yl)pyridin-3-yl)acetamide (25.0 mg, 45.3%) as a white solid. LCMS (Condition 4): retention time 2.08 min, [M+1]=447.2. HPLC (Condition 28): retention time=5.63 min, purity 94.65%. $^1$H NMR (400 MHz, $CD_3OD$) δ 2.21 (s, 3 H), 4.65 (s, 2 H), 7.21-7.26 (m, 2 H), 7.49 (br s, 5 H), 7.69-7.73 (m, 2 H), 7.88-7.94 (m, 2 H), 8.28-8.30 (m, 1 H), 8.42 (dd, J=2.0 Hz, J=2.4 Hz, 1 H), 8.55 (d, J=2.0 Hz, 1 H), 8.90 (d, J=2.4 Hz, 1 H).

Example 12

Isopropyl 5-(5-phenyl-4-(pyridin-2-ylmethylamino)phthalazin-1-yl)pyridin-3-ylcarbamate

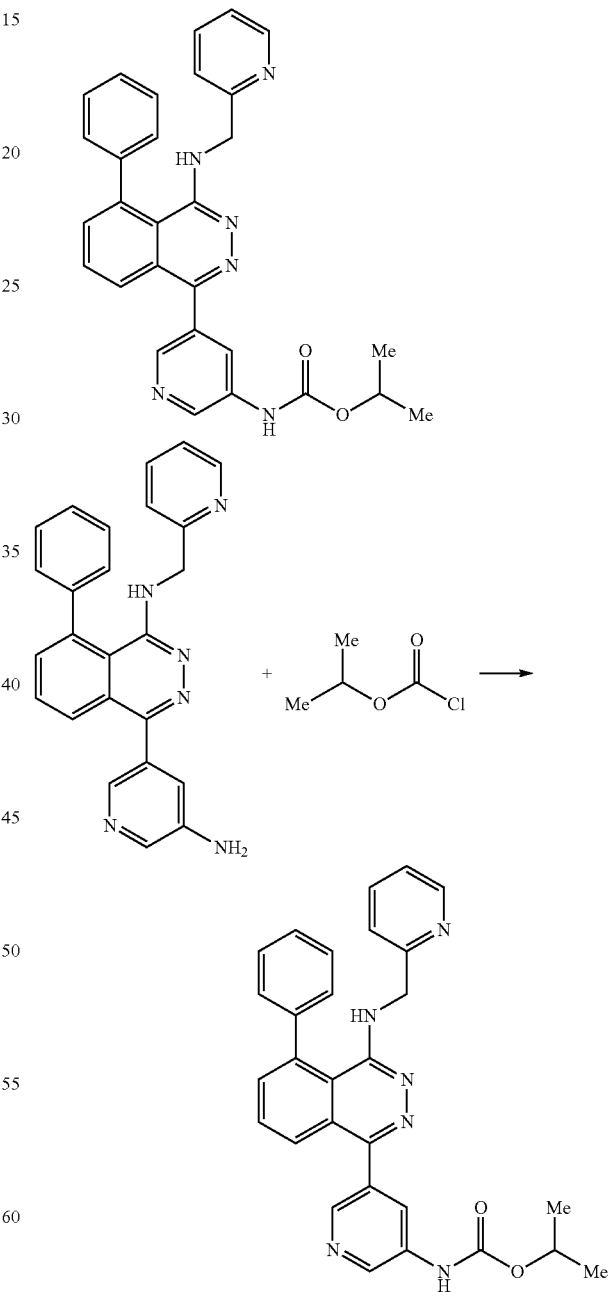

To a solution of 4-(5-aminopyridin-3-yl)-8-phenyl-N-(pyridin-2-ylmethyl)phthalazin-1-amine (50.0 mg, 0.124 mmol) in dichloromethane (5 mL) at room temperature was added pyridine (0.0200 mL, 0.247 mmol) followed by isopropyl carbonochloridate (18.2 mg, 0.148 mmol). The reaction mixture was stirred at ambient temperature for 12 h then diluted with dichloromethane (50 mL) and the organic portion washed with water (10 mL) followed by brine (10 mL). The organic layer was dried over $Na_2SO_4$, filtered and concentrated under reduced pressure. The resulting residue was purified by preparative HPLC (Condition 32 as described in general methods) to afford isopropyl (5-(5-phenyl-4-((pyridin-2-ylmethyl)amino)phthalazin-1-yl)pyridin-3-yl)carbamate (35.0 mg, 57.7%). LCMS (Condition 4): retention time 2.16 min, [M+1]=491.0. HPLC (Condition 28): retention time=6.66 min, purity 95.13%. $^1$H NMR (400 MHz, DMSO-$d_6$) δ 1.29 (d, J=6.0 Hz, 6 H), 4.65 (d, J=4.0 Hz, 2 H), 4.93 (sept, J=6.0 Hz, 1 H), 6.28 (t, J=4.0 Hz, 1 H), 7.22 (dd, J=6.0 Hz, J=7.6 Hz, 1 H), 7.28 (d, J=8.0 Hz, 1 H), 7.45-7.60 (m, 5 H), 7.68-7.73 (m, 2 H), 7.84-7.93 (m, 2 H), 8.17 (t, J=2.0 Hz, 1 H), 8.22-8.24 (m, 1 H), 8.48 (d, J=2.0 Hz, 1 H), 8.81 (d, J=2.0 Hz, 1 H), 10.00 (s, 1 H).

Example 13

N-Benzyl-4-(2-tert-butoxypyridin-4-yl)-8-phenylphthalazin-1-amine

To a solution of 1,4-dichloro-5-phenylphthalazine (0.400 g, 1.45 mmol), 2-(tert-butoxy)-4-(4,4,5,5-tetramethyl-1,3,2-dioxaborolan-2-yl)pyridine (0.484 g, 1.75 mmol) in dioxane (20 mL) and water (2 mL) was added phosphoric acid, potassium salt (0.617 g, 2.91 mmol). The reaction mixture was purged with nitrogen gas for 30 min and then $Pd_2(dba)_3$ (0.013 g, 0.015 mmol) was added followed by tricyclohexylphosphonium tetrafluoroborate (11 mg, 0.029 mmol). The purging was continued for a further 15 min and the reaction mixture heated to 95° C. for 12 h. The reaction mixture was diluted with water (50 mL) and extracted with ethyl acetate (3×50 mL). The combined organic layers were washed with brine, dried over $Na_2SO_4$, filtered and concentrated under reduced pressure. The resulting residue was purified by flash chromatography using Combiflash Isco (REDISEP®, $SiO_2$, 12 g, 0-30% ethyl acetate/petroleum ether) to get 1-(2-(tert-butoxy)pyridin-4-yl)-4-chloro-5-phenylphthalazine (0.400 g, 33.2%) as a brown solid. LCMS (Condition 11): retention time 1.22 min, [M+1]=390.2. $^1$H NMR (400 MHz, DMSO-$d_6$) δ 1.70 (s, 9 H), 6.84 (br s, 1 H), 7.05 (dd, J=1.2 Hz, J=5.2 Hz, 1 H), 7.36-7.44 (m, 2 H), 7.47-7.51 (m, 3 H), 8.06 (dd, J=1.2 Hz, J=7.6 Hz, 1 H), 8.15 (dd, J=0.8 Hz, J=4.8 Hz, 1 H), 8.26 (dd, J=7.2 Hz, J=8.0 Hz, 1 H), 8.47 (d, J=1.2 Hz, J=8.4 Hz, 1 H).

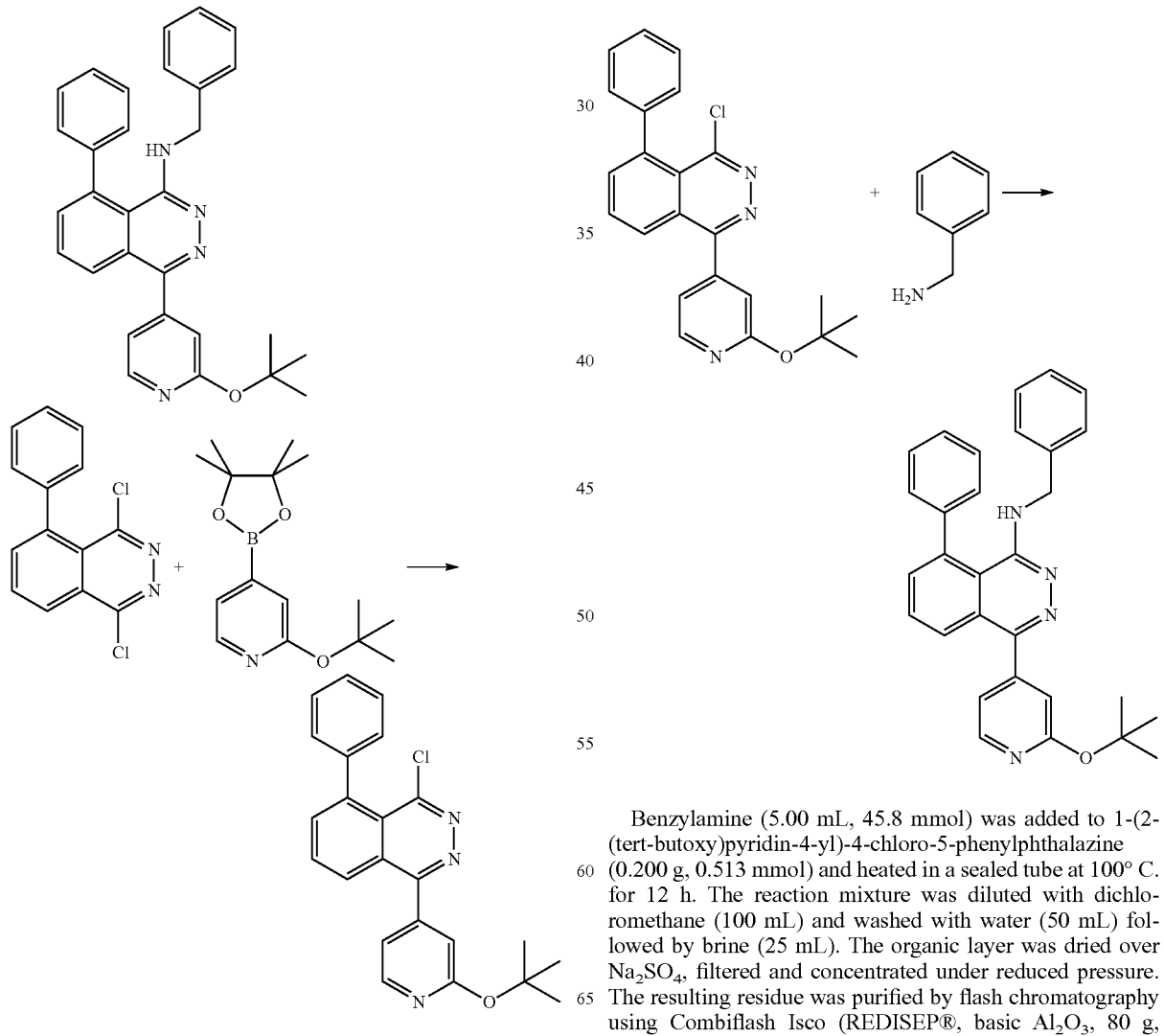

Benzylamine (5.00 mL, 45.8 mmol) was added to 1-(2-(tert-butoxy)pyridin-4-yl)-4-chloro-5-phenylphthalazine (0.200 g, 0.513 mmol) and heated in a sealed tube at 100° C. for 12 h. The reaction mixture was diluted with dichloromethane (100 mL) and washed with water (50 mL) followed by brine (25 mL). The organic layer was dried over $Na_2SO_4$, filtered and concentrated under reduced pressure. The resulting residue was purified by flash chromatography using Combiflash Isco (REDISEP®, basic $Al_2O_3$, 80 g, 0-70% ethyl acetate/petroleum ether) to remove excess benzyl amine. The resulting residue was then purified by preparative HPLC (Condition 33 as described in general methods) to afford N-benzyl-4-(2-(tert-butoxy)pyridin-4-yl)-8-phenylphthalazin-1-amine (0.120 g, 50.8%) as a white solid. LCMS (Condition 34): retention time 2.67 min, [M+1]=461.2. HPLC (Condition 35): retention time=21.80 min, purity 99.30%. $^1$H NMR (400 MHz, DMSO-$d_6$) δ 1.63 (s, 9 H), 4.50 (d, J=5.2 Hz, 2 H), 5.07 (t, J=5.2 Hz, 1 H), 6.90 (dd, J=0.4 Hz, J=0.8 Hz, 1 H), 7.00-7.03 (m, 2 H), 7.17 (dd, J=1.6 Hz, J=5.2 Hz, 1 H), 7.22-7.28 (m, 3 H), 7.42-7.50 (m, 5 H), 7.67 (dd, J=1.2 Hz, J=6.8 Hz, 1 H), 7.85-7.93 (m, 2 H), 8.31 (dd, J=0.4 Hz, J=5.2 Hz, 1 H).

Example 14

N-(3-(Methylsulfonamido)phenyl)-5-(5-phenyl-4-(pyridin-2-ylmethylamino)phthalazin-1-yl)nicotinamide

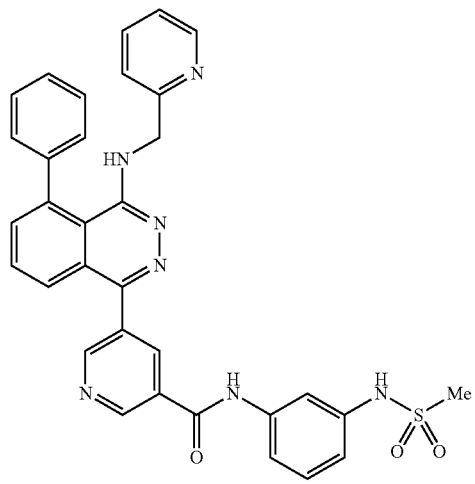

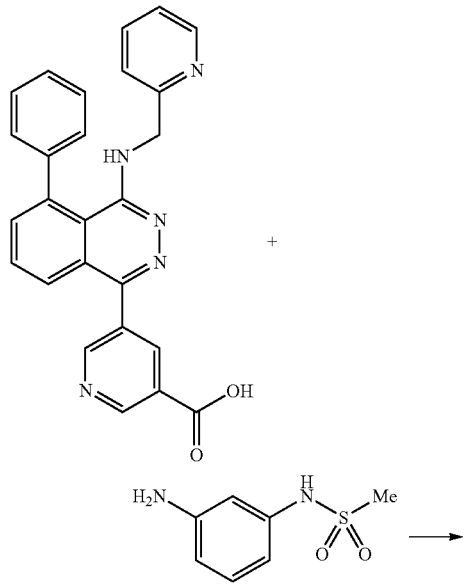

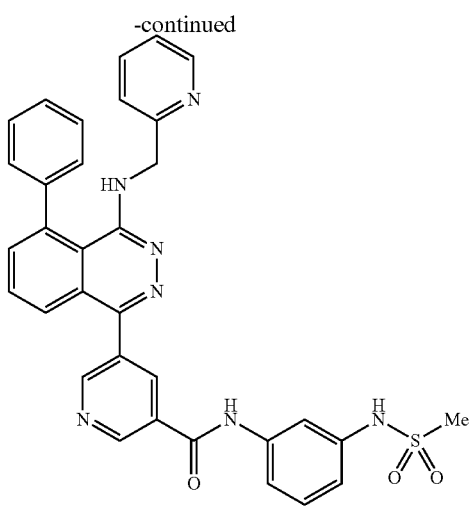

5-(5-Phenyl-4-((pyridin-2-ylmethyl)amino)phthalazin-1-yl)nicotinic acid (15.0 mg, 0.0350 mmol) was added to N-(3-aminophenyl)methanesulfonamide (7.73 mg, 0.0420 mmol) and a solution of HATU (19.7 mg, 0.0520 mmol) and DIPEA (0.0180 mL, 0.104 mmol) in DMF (0.5 mL) was added. The reaction mixture was stirred for 5 hours at room temperature. The volatile components were removed under high vacuum and the residue was purified by reverse phase preparative HPLC (Condition 36 as described in general methods) to afford N-(3-(methylsulfonamido)phenyl)-5-(5-phenyl-4-((pyridin-2-ylmethyl)amino)phthalazin-1-yl)nicotinamide (5.79 mg, 26.4%) as a white solid. LCMS (Condition 37): retention time 1.63 min, [M+1]=602.1, purity 95.02%. $^1$H NMR (400 MHz, DMSO-$d_6$) δ 3.01 (s, 3 H), 4.67 (d, J=4.4 Hz, 2 H), 6.34 (t, J=4.4 Hz, 1 H), 6.95-6.99 (m, 1 H), 7.21-7.24 (m, 1 H), 7.28 (d, J=8.0 Hz, 1 H), 7.30 (t, J=8.0 Hz, 1 H), 7.50-7.58 (m, 6 H), 7.68-7.77 (m, 3 H), 7.90-7.94 (m, 2 H), 8.22-8.24 (m, 1 H), 8.61 (t, J=2.0 Hz, 1 H), 9.05 (d, J=2.0 Hz, 1 H), 9.26 (d, J=2.0 Hz, 1 H), 10.60 (s, 1 H).

Example 15

5-(4-(3-Fluorophenylamino)-5-phenylphthalazin-1-yl)pyridine-3-sulfonamide

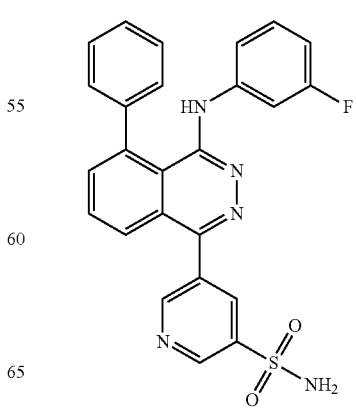

-continued

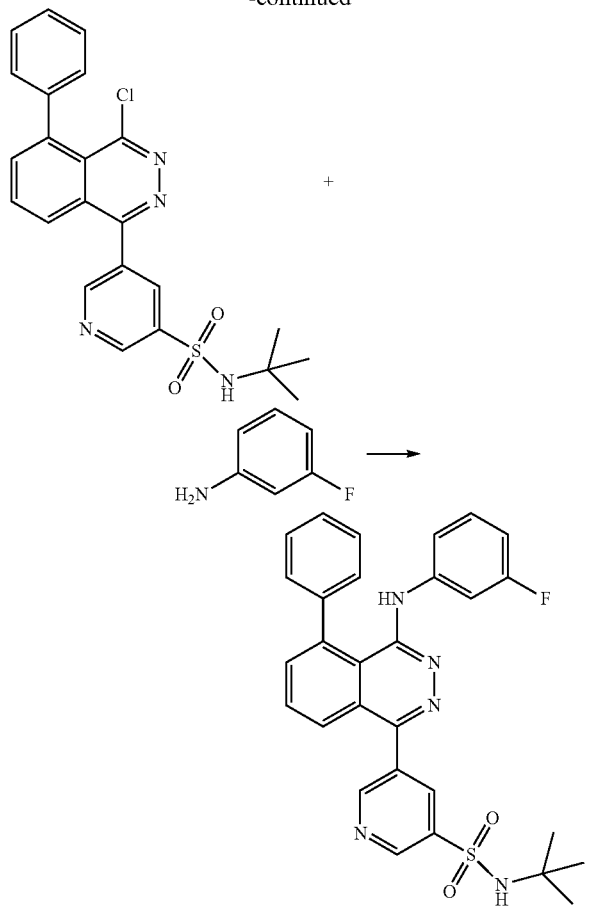

N-(tert-Butyl)-5-(4-chloro-5-phenylphthalazin-1-yl)pyridine-3-sulfonamide (1.00 g, 2.21 mmol) in 3-fluoroaniline (2.94 g, 26.5 mmol) was heated in a sealed tube at 100° C. for 12 h. On cooling, the volatile components were removed under reduced pressure and the resulting residue was purified by combiflash (REDISEP®, silica gel, 24 g, 60% EtOAc/hexanes) to obtain N-(tert-butyl)-5-(4-((3-fluorophenyl)amino)-5-phenylphthalazin-1-yl)pyridine-3-sulfonamide (0.70 g, 60%) as a brown solid. LCMS (Condition 11): retention time 1.20 min, [M+1]=528.4. $^1$H NMR (400 MHz, DMSO-$d_6$) δ 1.94 (s, 9 H), 6.50 (dd, J=1.2 Hz, J=8.4 Hz, 1 H), 6.76 (td, J=2.5 Hz, J=8.4 Hz, 1 H), 7.19-7.25 (m, 2 H), 7.53-7.66 (m, 6 H), 7.88-7.93 (m, 3 H), 8.05 (dd, J=6.8 Hz, J=8.4 Hz, 1 H), 8.54 (t, J=2.0 Hz, 1 H), 9.15 (d, J=2.0 Hz, 1 H), 9.16 (d, J=2.0 Hz, 1 H).

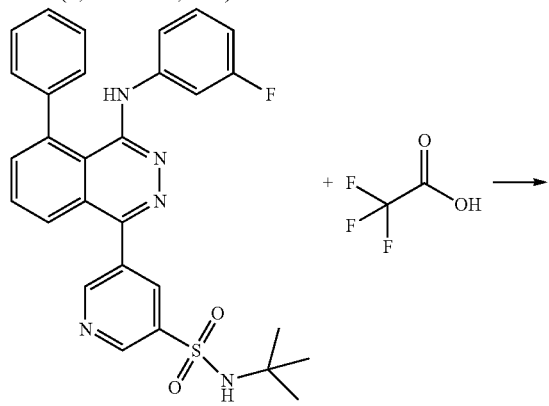

-continued

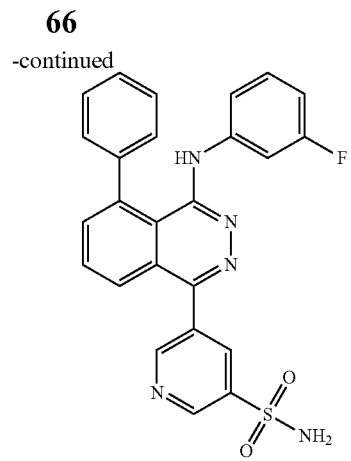

N-(tert-Butyl)-5-(4-((3-fluorophenyl)amino)-5-phenylphthalazin-1-yl)pyridine-3-sulfonamide (0.600 g, 1.14 mmol) was dissolved in TFA (10.0 mL, 130 mmol) and heated to 65° C. for 4 h. TFA was removed under reduced pressure and the resulting residue was diluted with saturated NaHCO$_3$ (100 mL). The reaction mixture was extracted with EtOAc (3×100 mL). The combined organic extracts were dried over anhydrous Na$_2$SO$_4$, filtered and concentrated under reduced pressure. The resulting residue was purified by combiflash (REDISEP®, silica gel, 40 g, 0-6% MeOH/DCM) to afford 5-(4-((3-fluorophenyl)amino)-5-phenylphthalazin-1-yl)pyridine-3-sulfonamide (0.15 g, 27%) as an off-white solid. LCMS (Condition 38): retention time 2.12 min, [M+1]=472.2. HPLC (Condition 25): retention time=9.61 min, purity 99.78%. $^1$H NMR (400 MHz, DMSO-$d_6$) δ 6.50 (dd, J=1.6 Hz, J=8.0 Hz, 1 H), 6.76 (td, J=2.0 Hz, J=8.4 Hz, 1 H), 7.19-7.25 (m, 2 H), 7.53-7.66 (m, 6 H), 7.76 (br s, 2 H), 7.90 (dd, J=1.2 Hz, J=7.2 Hz, 1 H), 7.95 (dd, J=1.2 Hz, J=8.0 Hz, 1 H), 8.05 (dd, J=7.2 Hz, J=8.0 Hz, 1 H), 8.54 (dd, J=2.0 Hz, J=2.4 Hz, 1 H), 9.15 (d, J=2.0 Hz, 1 H), 9.16 (d, J=2.4 Hz, 1 H).

Example 16

5-(5-Phenyl-4-(pyridin-2-ylmethylamino)phthalazin-1-yl)pyridin-3-ylsulfonylphosphoramidic acid

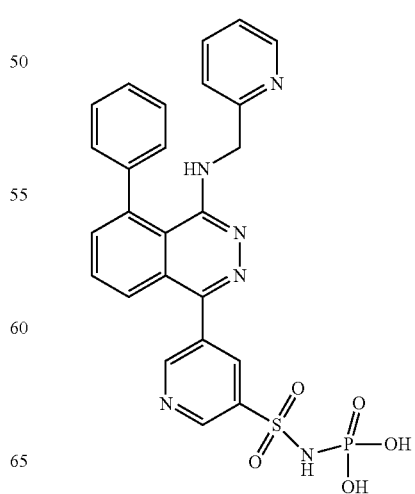

-continued

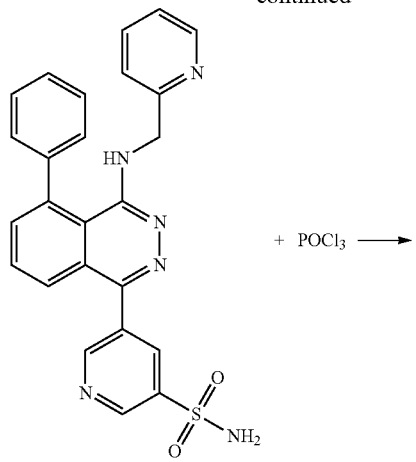

+ POCl₃ ⟶

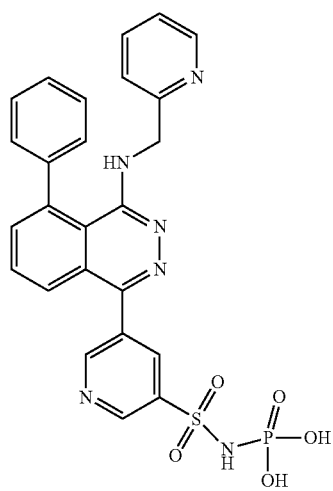

To a solution of 5-(5-phenyl-4-((pyridin-2-ylmethyl)amino)phthalazin-1-yl)pyridine-3-sulfonamide (1.00 g, 2.13 mmol) in dichloromethane (25 mL) was added DIPEA (1.49 mL, 8.54 mmol) at 0° C. and the reaction mixture was stirred for 10 min. POCl₃ (0.597 mL, 6.40 mmol) was added at 0° C. and the reaction mixture was allowed to stir for 3 h while warming to ambient temperature. DCM and excess POCl₃ was evaporated under reduced pressure. To the resulting residue was added ice-cold water (5 mL) and the resulting mixture stirred for 30 minutes at ambient temperature. The resulting precipitate was filtered and the solid washed successively with acetonitrile (10 mL) and acetone (10 mL). The solid was dissolved in 1.5N HCl (10 mL) and allowed to stir at ambient temperature for 3 h and the residue was purified by preparative HPLC (Condition 42 as described in general methods). Fractions containing the product were collected, combined and evaporated under reduced pressure at low temperature (30° C.). The residue was lyophilized with water to obtain 5-(5-phenyl-4-(pyridin-2-ylmethylamino)phthalazin-1-yl)pyridin-3-ylsulfonylphosphoramidic acid (600 mg, 51.3%) as a white solid. LCMS (Condition 2): retention time 1.60 min, [M+1]=549.2. HPLC (Condition 26): retention time=11.16 min, purity 99.05%. ¹H NMR (400 MHz, DMSO-d₆) δ 4.67 (d, J=3.6 Hz, 2 H), 6.48 (br s, 1 H), 7.21-7.25 (m, 1 H), 7.28 (d, J=8.0 Hz, 1 H), 7.51-7.59 (m, 5 H), 7.69-7.74 (m, 2 H), 7.91-7.94 (m, 2 H), 8.21-8.23 (m, 1 H), 8.51 (t, J=2.0 Hz, 1 H), 9.10 (t, J=2.0 Hz, 1 H), 9.13 (t, J=2.0 Hz, 1 H).

| Ex. No. | Structure | Name | ¹H NMR | LC/MS Rt (min) Method M + H |
|---|---|---|---|---|
| 17 | 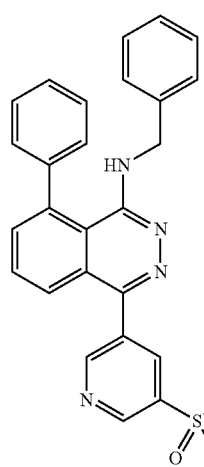 | 5-(4-(Benzylamino)-5-phenylphthalazin-1-yl)pyridine-3-sulfonamide | ¹H NMR (400 MHz, DMSO-d₆) δ 4.53 (d, J = 4.8 Hz, 2 H), 5.15 (t, J = 4.8 Hz, 1 H), 7.02-7.05 (m, 2 H), 7.23-7.29 (m, 3 H), 7.45-7.52 (m, 5 H), 7.72-7.74 (m, 3 H), 7.86 (dd, J = 1.2 Hz, J = 8.4 Hz, 1 H), 7.95 (dd, J = 7.2 Hz, J = 8.4 Hz, 1 H), 8.47 (t, J = 2.0 Hz, 1 H), 9.09 (d, J = 2.0 Hz, 1 H), 9.12 (d, J = 2.0 Hz, 1 H). | 2.27 Condition 10 466.0 (M-H) |

| Ex. No. | Structure | Name | ¹H NMR | LC/MS Rt (min) Method M + H |
|---|---|---|---|---|
| 18 | 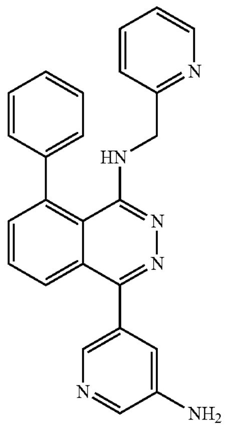 [SMILES: Nc1cncc(-c2nnc(NCc3ccccn3)c3c(-c4ccccc4)cccc23)c1] | 4-(5-Aminopyridin-3-yl)-8-phenyl-N-(pyridin-2-ylmethyl)phthalazin-1-amine | ¹H NMR (400 MHz, DMSO-d$_6$) δ 4.63 (d, J = 4.4 Hz, 2 H), 5.52 (s, 2 H), 6.20 (dd, J = 4.0 Hz, J = 4.4 Hz, 1 H), 7.16 (dd, J = 2.0 Hz, J = 2.4 Hz, 1 H), 7.20-7.23 (m, 1 H), 7.26 (d, J = 7.6 Hz, 1 H), 7.49-7.57 (m, 5 H), 7.65-7.72 (m, 2 H), 7.85-7.92 (m, 2 H), 7.96 (d, J = 2.0 Hz, 1 H), 8.08 (d, J = 2.8 Hz, 1 H), 8.23 (dt, J = 0.8 Hz, J = 4.0 Hz, 1 H). | 2.26 Condition 4 405.2 |
| 19 | 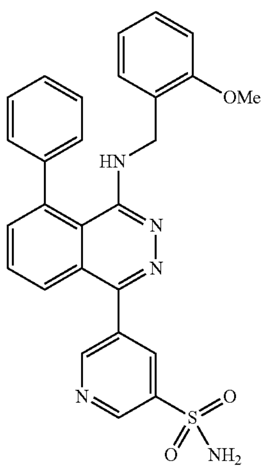 [SMILES: COc1ccccc1CNc1nnc(-c2cncc(S(N)(=O)=O)c2)c2cccc(-c3ccccc3)c12] | 5-(4-((2-Methoxybenzyl)amino)-5-phenylphthalazin-1-yl)pyridine-3-sulfonamide | ¹H NMR (400 MHz, DMSO-d$_6$) δ 3.70 (s, 3 H), 4.48 (d, J = 5.2 Hz, 2H), 5.13 (t, J = 5.2 Hz, 1 H), 6.81 (td, J = 0.8 Hz, J = 7.2 Hz, 1 H), 6.92 (d, J = 8.0 Hz, 1 H), 6.99 (dd, J = 1.6 Hz, J = 7.2 Hz, 1 H), 7.22 (td, J = 1.6 Hz, J = 8.0 Hz, 1 H), 7.45-7.48 (m, 5 H), 7.69 (dd, J = 1.2 Hz, J = 7.2 Hz, 1 H), 7.77 (br s, 2 H), 7.83 (dd, J = 1.2 Hz, J = 8.0 Hz, 1 H), 7.92 (dd, J = 7.2 Hz, J = 7.6 Hz, 1 H), 8.46 (t, J = 2.4 Hz, 1 H), 9.08 (d, J = 2.4 Hz, 1 H), 9.12 (d, J = 2.4 Hz, 1 H). | 2.19 Condition 39 498.0 |
| 20 | 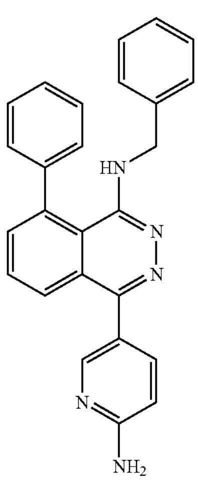 [SMILES: Nc1ccc(-c2nnc(NCc3ccccc3)c3c(-c4ccccc4)cccc23)cn1] | 4-(6-Aminopyridin-3-yl)-N-benzyl-8-phenylphthalazin-1-amine | ¹H NMR (400 MHz, DMSO-d$_6$) δ 4.48 (d, J = 5.2 Hz, 2 H), 4.92 (t, J = 5.2 Hz, 1 H), 6.22 (s, 2 H), 6.62 (d, J = 8.4 Hz, 1 H), 7.01-7.03 (m, 2 H), 7.22-7.28 (m, 3 H), 7.43-7.50 (m, 5 H), 7.64-7.68 (m, 2 H), 7.87-7.95 (m, 2 H), 8.18 (d, J = 2.0 Hz, 1 H). | 2.14 Condition 4 404.0 |

| Ex. No. | Structure | Name | ¹H NMR | LC/MS Rt (min) Method M + H |
|---|---|---|---|---|
| 21 | 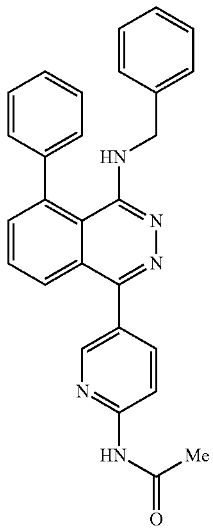 [SMILES: CC(=O)Nc1ccc(-c2nnc(NCc3ccccc3)c3c(-c4ccccc4)cccc23)cn1] | N-(5-(4-(Benzyl-amino)-5-phenylphthalazin-1-yl)pyridin-2-yl)acetamide | ¹H NMR (400 MHz, DMSO-d₆) δ 2.17 (s, 3 H), 4.50 (d, J = 5.2 Hz, 2 H), 5.02 (t, J = 5.2 Hz, 1 H), 7.02 (dd, J = 2.0 Hz, J = 8.0 Hz, 2 H), 7.21-7.29 (m, 3 H), 7.43-7.51 (m, 5 H), 7.68 (dd, J = 2.0 Hz, J = 6.0 Hz, 1 H), 7.88-7.92 (m, 2 H), 8.07 (dd, J = 2.4 Hz, J = 8.8 Hz, 1 H), 8.27 (d, J = 8.4 Hz, 1 H), 8.58 (dd, J = 0.8 Hz, J = 2.4 Hz, 1 H), 10.70 (s, 1 H). | 2.21 Condition 4 446.0 |
| 22 | 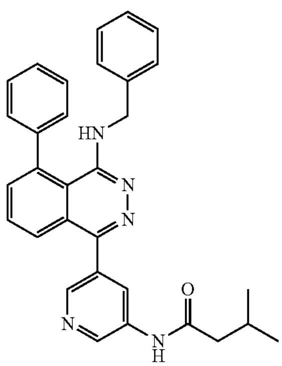 [SMILES: CC(C)CC(=O)Nc1cncc(-c2nnc(NCc3ccccc3)c3c(-c4ccccc4)cccc23)c1] | N-(5-(4-(Benzyl-amino)-5-phenylphthalazin-1-yl)pyridin-3-yl)-3-methylbutanamide | ¹H NMR (400 MHz, DMSO-d₆) δ 0.97 (d, J = 6.4 Hz, 6 H), 2.06-2.17 (m, 1 H), 2.28 (d, J = 7.2 Hz, 2 H), 4.51 (d, J = 5.2 Hz, 2 H), 5.06 (t, J = 5.2 Hz, 1 H), 7.03 (dd, J = 2.0 Hz, J = 8.0 Hz, 2 H), 7.21-7.29 (m, 3 H), 7.42-7.52 (m, 5 H), 7.69 (dd, J = 1.6 Hz, J = 6.8 Hz, 1 H), 7.85-7.95 (m, 2 H), 8.37 (t, J = 2.0 Hz, 1 H), 8.52 (d, J = 2.0 Hz, 1 H), 8.87 (d, J = 2.0 Hz, 1 H), 10.28 (s, 1 H). | 2.32 Condition 4 488.0 |
| 23 | 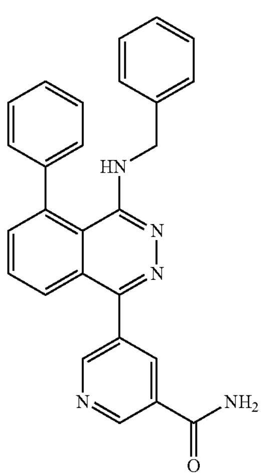 [SMILES: NC(=O)c1cncc(-c2nnc(NCc3ccccc3)c3c(-c4ccccc4)cccc23)c1] | 5-(4-(Benzyl-amino)-5-phenylphthalazin-1-yl)nicotinamide | ¹H NMR (400 MHz, DMSO-d₆) δ 4.51 (d, J = 4.8 Hz, 2 H), 5.09 (t, J = 4.8 Hz, 1 H), 7.02 (dd, J = 2.0 Hz, J = 8.0 Hz, 2 H), 7.22-7.28 (m, 3 H), 7.43-7.51 (m, 5 H), 7.70-7.72 (m, 2 H), 7.85 (dd, J = 1.6 Hz, J = 8.4 Hz, 1 H), 7.92 (dd, J = 7.2 Hz, J = 8.4 Hz, 1 H), 8.29 (br s, 1 H), 8.49 (t, J = 2.0 Hz, 1 H), 8.98 (d, J = 2.0 Hz, 1 H), 9.18 (d, J = 2.0 Hz, 1 H). | 2.05 Condition 34 432.0 |

-continued

| Ex. No. | Structure | Name | ¹H NMR | LC/MS Rt (min) Method M + H |
|---|---|---|---|---|
| 24 | 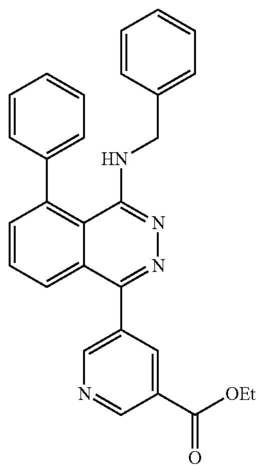 [SMILES: CCOC(=O)c1cncc(-c2nnc(NCc3ccccc3)c3c(-c4ccccc4)cccc23)c1] | Ethyl 5-(4-(benzyl-amino)-5-phenylphthalazin-1-yl) nicotinate | ¹H NMR (400 MHz, DMSO-d$_6$) δ 1.37 (t, J = 7.2 Hz, 3 H), 4.40 (q, J = 7.2 Hz, 2 H), 4.51 (d, J = 5.2 Hz, 2 H), 5.11 (t, J = 5.2 Hz, 1 H), 7.03 (dd, J = 2.0 Hz, J = 8.0 Hz, 2 H), 7.22-7.29 (m, 3 H), 7.43-7.50 (m, 5 H), 7.71 (dd, J = 1.6 Hz, J = 7.2 Hz, 1 H), 7.85 (dd, J = 1.2 Hz, J = 8.4 Hz, 1 H), 7.92 (dd, J = 7.6 Hz, J = 8.0 Hz, 1 H), 8.51 (t, J = 2.0 Hz, 1 H), 9.10 (d, J = 2.0 Hz, 1 H), 9.24 (d, J = 2.0 Hz, 1 H). | 2.36 Condition 34 461.0 |
| 25 | 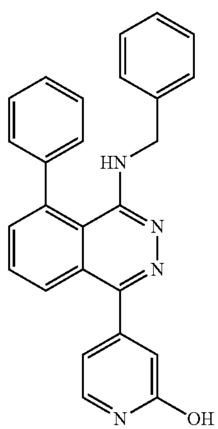 [SMILES: Oc1cc(-c2nnc(NCc3ccccc3)c3c(-c4ccccc4)cccc23)ccn1] | 4-(4-(Benzyl-amino)-5-phenylphthalazin-1-yl)pyridin-2-ol | ¹H NMR (400 MHz, DMSO-d$_6$) δ 4.49 (d, J = 4.8 Hz, 2 H), 5.07 (t, J = 4.8 Hz, 1 H), 6.42 (dd, J = 1.2 Hz, J = 6.4 Hz, 1 H), 6.52 (d, J = 1.2 Hz, 1 H), 6.99-7.09 (m, 2 H), 7.20-7.28 (m, 3 H), 7.40-7.48 (m, 5 H), 7.54 (d, J = 6.8 Hz, 1 H), 7.68 (dd, J = 2.0 Hz, J = 6.8 Hz, 1 H), 7.88-7.97 (m, 2 H), 11.80 (br s, 1 H). | 2.07 Condition 34 405.0 |
| 26 | 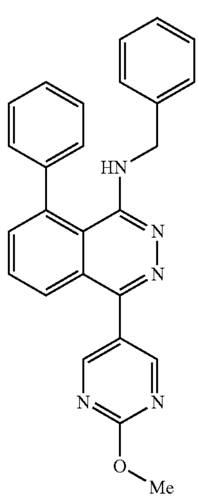 [SMILES: COc1ncc(-c2nnc(NCc3ccccc3)c3c(-c4ccccc4)cccc23)cn1] | N-Benzyl-4-(2-methoxy-pyrimidin-5-yl)-8-phenylphthalazin-1-amine | ¹H NMR (400 MHz, DMSO-d$_6$) δ 4.05 (s, 3 H), 4.51 (d, J = 4.8 Hz, 2 H), 5.07 (t, J = 4.8 Hz, 1 H), 7.03 (dd, J = 2.0 Hz, J = 8.0 Hz, 2 H), 7.21-7.28 (m, 3 H), 7.44-7.51 (m, 5 H), 7.71 (dd, J = 2.8 Hz, J = 6.0 Hz, 1 H), 7.90-7.93 (m, 2 H), 8.92 (s, 2 H). | 2.29 Condition 4 420.0 |

| Ex. No. | Structure | Name | ¹H NMR | LC/MS Rt (min) Method M + H |
|---|---|---|---|---|
| 27 | 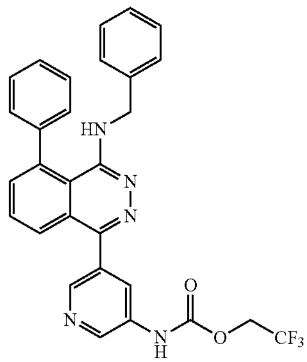 [SMILES: O=C(Nc1cncc(-c2nnc(NCc3ccccc3)c3c(-c4ccccc4)cccc23)c1)OCC(F)(F)F] | 2,2,2-Trifluoroethyl (5-(4-(benzylamino)-5-phenylphthalazin-1-yl)pyridin-3-yl)carbamate | ¹H NMR (400 MHz, DMSO-d$_6$) δ 4.51 (d, J = 4.8 Hz, 2 H), 4.86 (q, J = 9.2 Hz, 2 H), 5.06 (t, J = 4.8 Hz, 1 H), 7.03 (dd, J = 1.6 Hz, J = 7.6 Hz, 2 H), 7.21-7.30 (m, 3 H), 7.43-7.51 (m, 5 H), 7.69 (dd, J = 1.6 Hz, J = 6.8 Hz, 1 H), 7.85-7.93 (m, 2 H), 8.17 (br s, 1 H), 8.54 (d, J = 1.6 Hz, 1 H), 8.82 (d, J = 2.4 Hz, 1 H), 10.59 (br s, 1 H). | 2.06 Condition 37 530.0 |
| 28 | 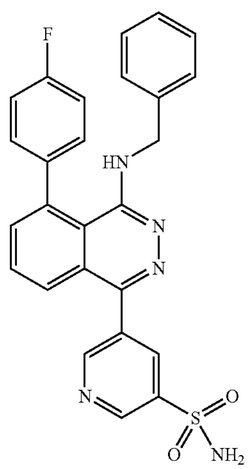 [SMILES: NS(=O)(=O)c1cncc(-c2nnc(NCc3ccccc3)c3c(-c4ccc(F)cc4)cccc23)c1] | 5-(4-(Benzylamino)-5-(4-fluorophenyl)phthalazin-1-yl)pyridine-3-sulfonamide | ¹H NMR (400 MHz, DMSO-d$_6$) δ 4.54 (d, J = 4.8 Hz, 2 H), 5.06 (t, J = 4.8 Hz, 1 H), 7.10 (dd, J = 2.0 Hz, J = 7.6 Hz, 2 H), 7.23-7.33 (m, 5 H), 7.51-7.58 (m, 2 H), 7.71-7.75 (m, 3 H), 7.85 (dd, J = 2.0 Hz, J = 8.4 Hz, 1 H), 7.94 (dd, J = 7.2 Hz, J = 8.0 Hz, 1 H), 8.46 (t, J = 2.0 Hz, 1 H), 9.08 (d, J = 2.0 Hz, 1 H), 9.12 (d, J = 2.0 Hz, 1 H). | 1.71 Condition 37 486.0 |
| 29 | 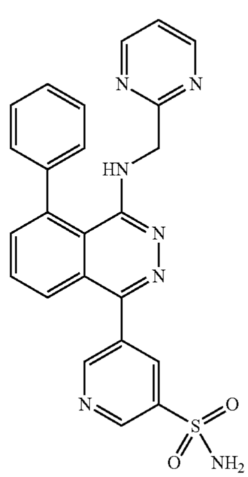 [SMILES: NS(=O)(=O)c1cncc(-c2nnc(NCc3ncccn3)c3c(-c4ccccc4)cccc23)c1] | 5-(5-Phenyl-4-((pyrimidin-2-ylmethyl)amino)phthalazin-1-yl)pyridine-3-sulfonamide | ¹H NMR (400 MHz, DMSO-d$_6$) δ 4.73 (d, J = 4.0 Hz, 2 H), 6.46 (t, J = 4.0 Hz, 1 H), 7.38 (t, J = 4.8 Hz, 1 H), 7.52-7.63 (m, 5 H), 7.72-7.75 (m, 3 H), 7.86 (dd, J = 1.2 Hz, J = 8.0 Hz, 1 H), 7.95 (dd, J = 7.2 Hz, J = 8.4 Hz, 1 H), 8.48 (t, J = 2.0 Hz, 1 H), 8.60 (d, J = 4.8 Hz, 2 H), 9.10 (d, J = 2.0 Hz, 1 H), 9.12 (d, J = 2.0 Hz, 1 H). | 1.85 Condition 38 470.0 |

| Ex. No. | Structure | Name | ¹H NMR | LC/MS Rt (min) Method M + H |
|---|---|---|---|---|
| 30 | 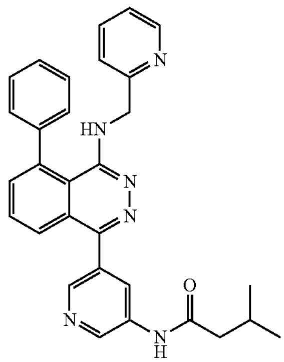 [SMILES: CC(C)CC(=O)Nc1cncc(-c2nnc(NCc3ccccn3)c3c(-c4ccccc4)cccc23)c1] | 3-Methyl-N-(5-(5-phenyl-4-((pyridin-2-ylmethyl)amino) phthalazin-1-yl)pyridin-3-yl)butanamide | ¹H NMR (400 MHz, DMSO-d₆) δ 0.97 (d, J = 6.4 Hz, 6 H), 2.08-2.15 (m, 1 H), 2.28 (d, J = 7.2 Hz, 2 H), 4.65 (d, J = 4.0 Hz, 2 H), 6.27 (t, J = 4.0 Hz, 1 H), 7.22 (dd, J = 5.6 Hz, J = 7.2 Hz, 1 H), 7.27 (d, J = 8.0 Hz, 1 H), 7.51-7.58 (m, 5 H), 7.67-7.72 (m, 2 H), 7.85-7.93 (m, 2 H), 8.23 (d, J = 4.0 Hz, 1 H), 8.37 (dd, J = 2.0 Hz, J = 2.4 Hz, 1 H), 8.52 (d, J = 2.0 Hz, 1 H), 8.87 (d, J = 2.4 Hz, 1 H), 10.27 (s, 1 H). | 1.74 Condition 37 489.2 |
| 31 | 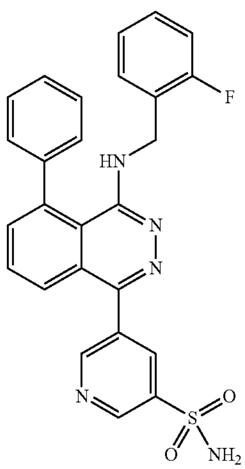 | 5-(4-((2-Fluorobenzyl) amino)-5-phenylphthalazin-1-yl)pyridine-3-sulfonamide | ¹H NMR (400 MHz, DMSO-d₆) δ 4.56 (d, J = 5.2 Hz, 2 H), 5.08 (t, J = 5.2 Hz, 1 H), 7.07-7.16 (m, 3 H), 7.27-7.33 (m, 1 H), 7.42-7.48 (m, 5 H), 7.72-7.74 (m, 3 H), 7.85 (dd, J = 1.6 Hz, J = 8.4 Hz, 1 H), 7.94 (dd, J = 7.2 Hz, J = 8.4 Hz, 1 H), 8.46 (t, J = 2.0 Hz, 1 H), 9.08 (d, J = 2.0 Hz, 1 H), 9.12 (d, J = 2.0 Hz, 1 H). | 1.74 Condition 37 486.0 |
| 32 | 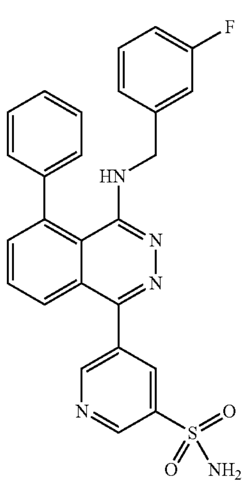 [SMILES: NS(=O)(=O)c1cncc(-c2nnc(NCc3cccc(F)c3)c3c(-c4ccccc4)cccc23)c1] | 5-(4-((3-Fluorobenzyl) amino)-5-phenylphthalazin-1-yl)pyridine-3-sulfonamide | ¹H NMR (400 MHz, DMSO-d₆) δ 4.54 (d, J = 4.8 Hz, 2 H), 5.15 (t, J = 4.8 Hz, 1 H), 6.85-6.88 (m, 1 H), 6.91 (d, J = 7.6 Hz, 1 H), 7.05 (td, J = 2.0 Hz, J = 8.4 Hz, 1 H), 7.30 (td, J = 6.0 Hz, J = 8.0 Hz, 1 H), 7.44-7.53 (m, 5 H), 7.73-7.75 (m, 3 H), 7.85 (dd, J = 1.2 Hz, J = 8.4 Hz, 1 H), 7.95 (dd, J = 7.2 Hz, J = 8.0 Hz, 1 H), 8.46 (t, J = 2.0 Hz, 1 H), 9.08 (d, J = 2.0 Hz, 1 H), 9.12 (d, J = 2.0 Hz, 1 H). | 1.70 Condition 37 486.0 |

| Ex. No. | Structure | Name | ¹H NMR | LC/MS Rt (min) Method M + H |
|---|---|---|---|---|
| 33 | 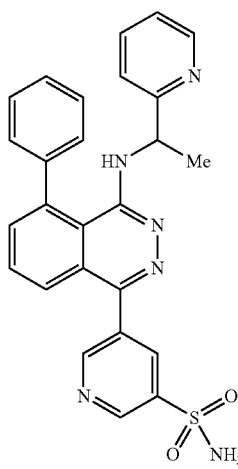 Enantiomer-1 | 5-(5-Phenyl-4-((1-(pyridin-2-yl)ethyl)amino)phthalazin-1-yl)pyridine-3-sulfonamide | ¹H NMR (400 MHz, DMSO-d$_6$) δ 1.20 (d, J = 6.8 Hz, 3 H), 5.29-5.36 (m, 1 H), 6.01 (d, J = 6.8 Hz, 1 H), 7.18-7.21 (m, 1 H), 7.26 (d, J = 8.0 Hz, 1 H), 7.54-7.64 (m, 5 H), 7.65-7.75 (m, 4 H), 7.84 (dd, J = 1.2 Hz, J = 8.4 Hz, 1 H), 7.94 (dd, J = 7.6 Hz, J = 8.4 Hz, 1 H), 8.27-8.29 (m, 1 H), 8.45 (t, J = 2.0 Hz, 1 H), 9.08 (d, J = 2.0 Hz, 1 H), 9.10 (d, J = 2.0 Hz, 1 H). | 2.064 Condition 40 483.2 Chiral HPLC Condition 41: retention time 3.68 min, Purity 100% |
| 34 | 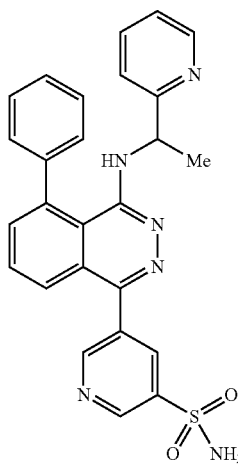 Enantiomer-2 | 5-(5-Phenyl-4-((1-(pyridin-2-yl)ethyl)amino)phthalazin-1-yl)pyridine-3-sulfonamide | ¹H NMR (400 MHz, DMSO-d$_6$) δ 1.20 (d, J = 6.8 Hz, 3 H), 5.29-5.36 (m, 1 H), 6.01 (d, J = 6.8 Hz, 1 H), 7.18-7.21 (m, 1 H), 7.26 (d, J = 8.0 Hz, 1 H), 7.54-7.64 (m, 5 H), 7.65-7.75 (m, 4 H), 7.84 (dd, J = 1.2 Hz, J = 8.4 Hz, 1 H), 7.94 (dd, J = 7.6 Hz, J = 8.4 Hz, 1 H), 8.27-8.29 (m, 1 H), 8.45 (t, J = 2.0 Hz, 1 H), 9.08 (d, J = 2.0 Hz, 1 H), 9.10 (d, J = 2.0 Hz, 1 H). | 2.067 Condition 40 483.2 Chiral HPLC Condition 41: retention time 4.43 min, Purity 99.38% |
| 35 | 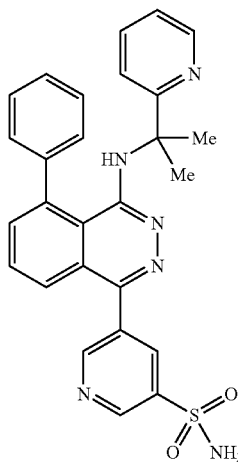 | 5-(5-Phenyl-4-((2-(pyridin-2-yl)propan-2-yl)amino)phthalazin-1-yl)pyridine-3-sulfonamide | ¹H NMR (400 MHz, DMSO-d$_6$) δ 1.45 (s, 6 H), 5.78 (s, 1 H), 7.14 (ddd, J = 0.8 Hz, J = 4.8 Hz, J = 6.0 Hz, 1 H), 7.34 (d, J = 8.0 Hz, 1 H), 7.56-7.65 (m, 8 H), 7.77 (dd, J = 1.2 Hz, J = 7.2 Hz, 1 H), 7.84 (dd, J = 1.2 Hz, J = 8.4 Hz, 1 H), 7.94 (dd, J = 7.2 Hz, J = 8.4 Hz, 1 H), 8.34-8.36 (m, 1 H), 8.41 (t, J = 2.0 Hz, 1 H), 9.04 (d, J = 2.0 Hz, 1 H), 9.07 (d, J = 2.0 Hz, 1 H). | |

| Ex. No. | Structure | Name | ¹H NMR | LC/MS Rt (min) Method M + H |
|---|---|---|---|---|
| 36 | 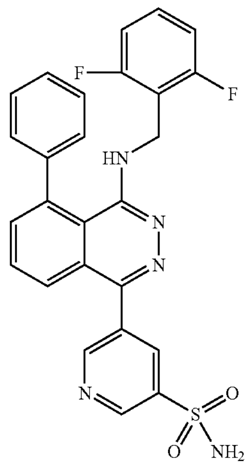 [SMILES: NS(=O)(=O)c1cncc(-c2nnc(NCc3c(F)cccc3F)c3c(-c4ccccc4)cccc23)c1] | 5-(4-((2,6-Difluorobenzyl)amino)-5-phenylphthalazin-1-yl)pyridine-3-sulfonamide | ¹H NMR (400 MHz, DMSO-$d_6$) δ 4.58 (d, J = 4.8 Hz, 2 H), 4.84 (t, J = 4.8 Hz, 1 H), 7.04 (t, J = 8.0 Hz, 2 H), 7.35-7.41 (m, 6 H), 7.70-7.73 (m, 3 H), 7.84 (dd, J = 1.2 Hz, J = 8.4 Hz, 1 H), 7.94 (dd, J = 7.2 Hz, J = 8.4 Hz, 1 H), 8.47 (t, J = 2.0 Hz, 1 H), 9.09 (d, J = 2.0 Hz, 1 H), 9.13 (d, J = 2.0 Hz, 1 H). | 1.68 Condition 37 504.0 |
| 37 | 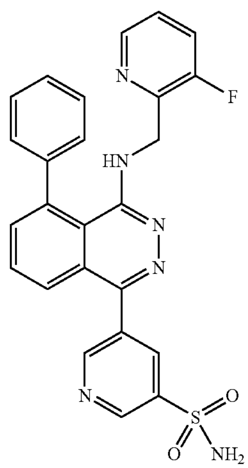 [SMILES: NS(=O)(=O)c1cncc(-c2nnc(NCc3ncccc3F)c3c(-c4ccccc4)cccc23)c1] | 5-(4-((3-Fluoropyridin-2-yl)methylamino)-5-phenylphthalazin-1-yl)pyridine-3-sulfonamide | ¹H NMR (400 MHz, DMSO-$d_6$) δ 4.72 (br d, J = 2.4 Hz, 2 H), 6.49 (t, J = 4.8 Hz, 1 H), 7.36-7.39 (m, 1 H), 7.50-7.74 (m, 9 H), 7.86 (dd, J = 1.2 Hz, J = 8.0 Hz, 1 H), 7.95 (dd, J = 7.2 Hz, J = 8.4 Hz, 1 H), 8.05-8.06 (m, 1 H), 8.48 (t, J = 2.0 Hz, 1 H), 9.10 (d, J = 2.0 Hz, 1 H), 9.13 (d, J = 2.0 Hz, 1 H). | 1.50 Condition 37 487.0 |
| 38 | 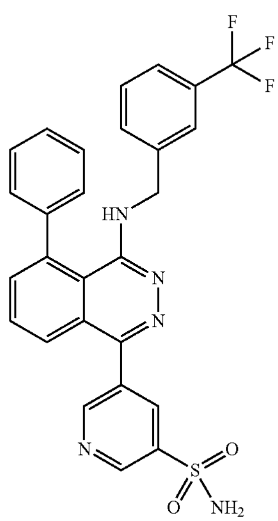 [SMILES: NS(=O)(=O)c1cncc(-c2nnc(NCc3cccc(C(F)(F)F)c3)c3c(-c4ccccc4)cccc23)c1] | 5-(5-Phenyl-4-((3-(trifluoromethyl)benzyl)amino)phthalazin-1-yl)pyridine-3-sulfonamide | ¹H NMR (400 MHz, DMSO-$d_6$) δ 4.62 (d, J = 5.2 Hz, 2 H), 5.20 (t, J = 5.2 Hz, 1 H), 7.40-7.54 (m, 8 H), 7.62 (d, J = 8.0 Hz, 1 H), 7.73-7.76 (m, 3 H), 7.86 (dd, J = 1.2 Hz, J = 8.4 Hz, 1 H), 7.96 (dd, J = 7.2 Hz, J = 8.0 Hz, 1 H), 8.46 (t, J = 2.0 Hz, 1 H), 9.09 (d, J = 2.0 Hz, 1 H), 9.12 (d, J = 2.0 Hz, 1 H). | 1.87 Condition 37 536.0 |

-continued

| Ex. No. | Structure | Name | ¹H NMR | LC/MS Rt (min) Method M + H |
|---|---|---|---|---|
| 39 | 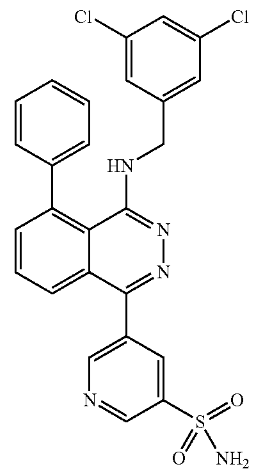 [SMILES: NS(=O)(=O)c1cncc(-c2nnc(NCc3cc(Cl)cc(Cl)c3)c3c(-c4ccccc4)cccc23)c1] | 5-(4-((3,5-Dichlorobenzyl)amino)-5-phenylphthalazin-1-yl)pyridine-3-sulfonamide | ¹H NMR (400 MHz, DMSO-d₆) δ 4.54 (d, J = 5.2 Hz, 2 H), 5.20 (t, J = 5.2 Hz, 1 H), 7.16 (d, J = 2.0 Hz, 2 H), 7.48 (t, J = 2.0 Hz, 1 H), 7.49-7.54 (m, 5 H), 7.73-7.77 (m, 3 H), 7.86 (dd, J = 1.2 Hz, J = 8.0 Hz, 1 H), 7.96 (dd, J = 7.2 Hz, J = 8.0 Hz, 1 H), 8.46 (dd, J = 2.0 Hz, J = 2.4 Hz, 1 H), 9.09 (d, J = 2.0 Hz, 1 H), 9.13 (d, J = 2.4 Hz, 1 H). | 1.99 Condition 37 535.9 |
| 40 | 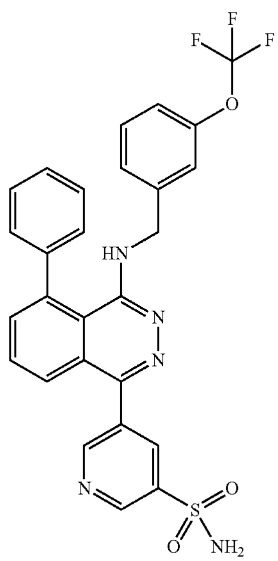 [SMILES: NS(=O)(=O)c1cncc(-c2nnc(NCc3cccc(OC(F)(F)F)c3)c3c(-c4ccccc4)cccc23)c1] | 5-(5-Phenyl-4-((3-(trifluoromethoxy)benzyl)amino)phthalazin-1-yl)pyridine-3-sulfonamide | ¹H NMR (400 MHz, DMSO-d₆) δ 4.58 (d, J = 5.2 Hz, 2 H), 5.19 (t, J = 5.2 Hz, 1 H), 7.06 (br s, 1 H), 7.13 (d, J = 7.6 Hz, 1 H), 7.20-7.25 (m, 1 H), 7.39-7.53 (m, 6 H), 7.73-7.76 (m, 3 H), 7.86 (dd, J = 1.2 Hz, J = 8.4 Hz, 1 H), 7.96 (dd, J = 7.2 Hz, J = 8.4 Hz, 1 H), 8.46 (dd, J = 2.0 Hz, J = 2.4 Hz, 1 H), 9.09 (d, J = 2.0 Hz, 1 H), 9.13 (d, J = 2.4 Hz, 1 H). | 1.92 Condition 37 552.0 |
| 41 | 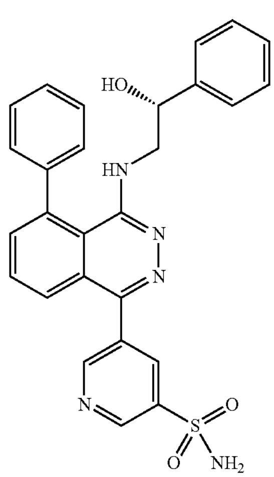 [SMILES: NS(=O)(=O)c1cncc(-c2nnc(NC[C@H](O)c3ccccc3)c3c(-c4ccccc4)cccc23)c1] | (R)-5-(4-((2-Hydroxy-2-phenylethyl)amino)-5-phenylphthalazin-1-yl)pyridine-3-sulfonamide | ¹H NMR (400 MHz, DMSO-d₆) δ 3.30-3.41 (m, 1 H), 3.66-3.71 (m, 1 H), 4.55-4.59 (m, 1 H), 5.26 (t, J = 5.2 Hz, 1 H), 5.32 (d, J = 4.4 Hz, 1 H), 7.17-7.25 (m, 5 H), 7.28-7.55 (m, 5 H), 7.68 (dd, J = 1.2 Hz, J = 1.2 Hz, 1 H), 7.73 (br s, 2 H), 7.83 (dd, J = 1.2 Hz, J = 8.4 Hz, 1 H), 7.92 (dd, J = 7.2 Hz, J = 8.0 Hz, 1 H), 8.46 (t, J = 2.0 Hz, 1 H), 9.08 (d, J = 2.0 Hz, 1 H), 9.12 (d, J = 2.0 Hz, 1 H). | 1.45 Condition 37 498.0 |

| Ex. No. | Structure | Name | ¹H NMR | LC/MS Rt (min) Method M + H |
|---|---|---|---|---|
| 42 | 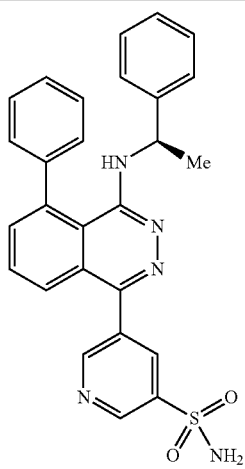 [SMILES: C[C@@H](Nc1nnc(-c2cncc(S(N)(=O)=O)c2)c2cccc(-c3ccccc3)c12)c1ccccc1] | (R)-5-(5-Phenyl-4-((1-phenylethyl)amino)phthalazin-1-yl)pyridine-3-sulfonamide | ¹H NMR (400 MHz, DMSO-$d_6$) δ 1.07 (d, J = 6.8 Hz, 3 H), 5.12 (d, J = 6.4 Hz, 1 H), 5.20 (dq, J = 6.4 Hz, J = 6.8 Hz, 1 H), 7.05 (dd, J = 2.0 Hz, J = 8.4 Hz, 2 H), 7.16-7.27 (m, 3 H), 7.56-7.72 (m, 7 H), 7.76 (dd, J = 1.2 Hz, J = 7.2 Hz, 1 H), 7.84 (dd, J = 1.2 Hz, J = 8.4 Hz, 1 H), 7.95 (dd, J = 7.6 Hz, J = 8.4 Hz, 1 H), 8.43 (t, J = 2.0 Hz, 1 H), 9.05 (d, J = 2.0 Hz, 1 H), 9.10 (d, J = 2.0 Hz, 1 H). | 1.78 Condition 37 482.0 |
| 43 | 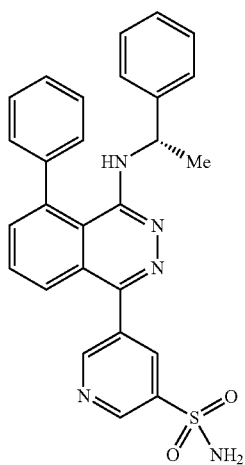 [SMILES: C[C@H](Nc1nnc(-c2cncc(S(N)(=O)=O)c2)c2cccc(-c3ccccc3)c12)c1ccccc1] | (S)-5-(5-Phenyl-4-((1-phenylethyl)amino)phthalazin-1-yl)pyridine-3-sulfonamide | ¹H NMR (400 MHz, DMSO-$d_6$) δ 1.07 (d, J = 6.8 Hz, 3 H), 5.12 (d, J = 6.4 Hz, 1 H), 5.20 (dq, J = 6.4 Hz, J = 6.8 Hz, 1 H), 7.05 (dd, J = 2.0 Hz, J = 8.4 Hz, 2 H), 7.16-7.27 (m, 3 H), 7.56-7.72 (m, 7 H), 7.76 (dd, J = 1.2 Hz, J = 7.2 Hz, 1 H), 7.84 (dd, J = 1.2 Hz, J = 8.4 Hz, 1 H), 7.95 (dd, J = 7.6 Hz, J = 8.4 Hz, 1 H), 8.43 (t, J = 2.0 Hz, 1 H), 9.05 (d, J = 2.0 Hz, 1 H), 9.10 (d, J = 2.0 Hz, 1 H). | 1.78 Condition 37 482.0 |
| 44 | 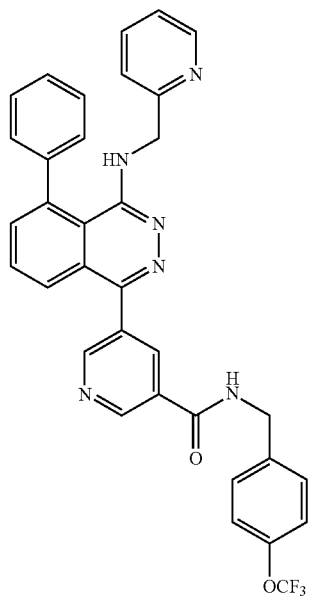 [SMILES: O=C(NCc1ccc(OC(F)(F)F)cc1)c1cncc(-c2nnc(NCc3ccccn3)c3c(-c4ccccc4)cccc23)c1] | 5-(5-Phenyl-4-((pyridin-2-ylmethyl)amino)phthalazin-1-yl)-N-(4-(trifluoromethoxy)benzyl)nicotinamide | ¹H NMR (400 MHz, DMSO-$d_6$) δ 4.57 (d, J = 6.0 Hz, 2 H), 4.66 (d, J = 4.4 Hz, 2 H), 6.32 (t, J = 4.4 Hz, 1 H), 7.22 (dd, J = 5.2 Hz, J = 6.8 Hz, 1 H), 7.27 (d, J = 7.6 Hz, 1 H), 7.34 (d, J = 7.6 Hz, 2 H), 7.48-7.60 (m, 7 H), 7.68-7.73 (m, 2 H), 7.85 (dd, J = 1.6 Hz, J = 8.4 Hz, 1 H), 7.92 (dd, J = 7.2 Hz, J = 8.4 Hz, 1 H), 8.20-8.23 (m, 1 H), 8.54 (t, J = 2.0 Hz, 1 H), 9.01 (d, J = 2.0 Hz, 1 H), 9.21 (d, J = 2.0 Hz, 1 H), 9.41 (t, J = 6.0 Hz, 1 H). | 2.02 Condition 37 607.1 |

| Ex. No. | Structure | Name | ¹H NMR | LC/MS Rt (min) Method M + H |
|---|---|---|---|---|
| 45 | 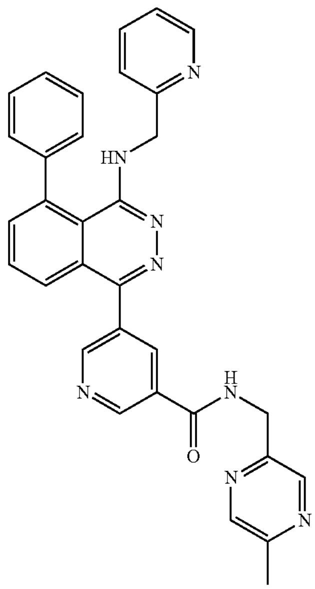 [SMILES: Cc1cnc(CNC(=O)c2cncc(-c3nnc(NCc4ccccn4)c4c(-c5ccccc5)cccc34)c2)cn1] | N-((5-Methylpyrazin-2-yl)methyl)-5-(5-phenyl-4-((pyridin-2-ylmethyl)amino)phthalazin-1-yl)nicotinamide | ¹H NMR (400 MHz, DMSO-d$_6$) δ 2.48 (s, 3 H), 4.63 (d, J = 5.6 Hz, 2 H), 4.66 (d, J = 4.4 Hz, 2 H), 6.32 (t, J = 4.4 Hz, 1 H), 7.22 (dd, J = 5.2 Hz, J = 6.8 Hz, 1 H), 7.27 (d, J = 8.0 Hz, 1 H), 7.50-7.60 (m, 5 H), 7.68-7.73 (m, 2 H), 7.86 (dd, J = 1.2 Hz, J = 8.4 Hz, 1 H), 7.93 (dd, J = 7.2 Hz, J = 8.0 Hz, 1 H), 8.21-8.23 (m, 1 H), 8.49 (d, J = 0.8 Hz, 1 H), 8.54 (t, J = 2.0 Hz, 1 H), 8.56 (d, J = 1.2 Hz, 1 H), 9.01 (d, J = 2.4 Hz, 1 H), 9.20 (d, J = 2.4 Hz, 1 H), 9.47 (t, J = 5.6 Hz, 1 H). | 1.43 Condition 37 539.1 |
| 46 | 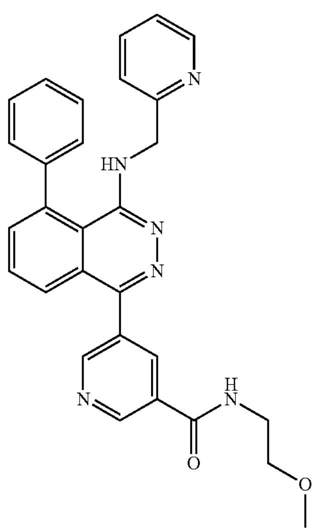 [SMILES: COCCNC(=O)c1cncc(-c2nnc(NCc3ccccn3)c3c(-c4ccccc4)cccc23)c1] | N-(2-Methoxyethyl)-5-(5-phenyl-4-((pyridin-2-ylmethyl)amino)phthalazin-1-yl)nicotinamide | ¹H NMR (400 MHz, DMSO-d$_6$) δ 3.28 (s, 3 H), 3.47-3.50 (m, 4 H), 4.65 (d, J = 4.4 Hz, 2 H), 6.32 (t, J = 4.4 Hz, 1 H), 7.21 (dd, J = 5.2 Hz, J = 6.8 Hz, 1 H), 7.27 (d, J = 7.6 Hz, 1 H), 7.50-7.60 (m, 5 H), 7.68-7.73 (m, 2 H), 7.84 (dd, J = 1.2 Hz, J = 8.4 Hz, 1 H), 7.93 (dd, J = 7.2 Hz, J = 8.0 Hz, 1 H), 8.21-8.23 (m, 1 H), 8.50 (t, J = 2.0 Hz, 1 H), 8.87 (t, J = 4.8 Hz, 1 H), 8.99 (d, J = 2.0 Hz, 1 H), 9.16 (d, J = 2.0 Hz, 1 H). | 1.43 Condition 37 491.0 |
| 47 | 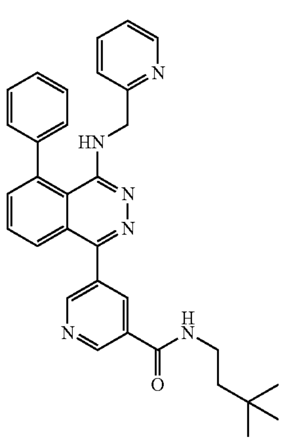 [SMILES: CC(C)(C)CCNC(=O)c1cncc(-c2nnc(NCc3ccccn3)c3c(-c4ccccc4)cccc23)c1] | N-(3,3-Dimethylbutyl)-5-(5-phenyl-4-((pyridin-2-ylmethyl)amino)phthalazin-1-yl)nicotinamide | ¹H NMR (400 MHz, DMSO-d$_6$) δ 0.94 (s, 9 H), 1.47-1.52 (m, 2 H), 3.32-3.35 (m, 2 H), 4.65 (d, J = 4.0 Hz, 2 H), 6.32 (t, J = 4.0 Hz, 1 H), 7.21 (dd, J = 5.2 Hz, J = 6.8 Hz, 1 H), 7.27 (d, J = 8.0 Hz, 1 H), 7.50-7.58 (m, 5 H), 7.68-7.73 (m, 2 H), 7.84 (dd, J = 1.2 Hz, J = 8.0 Hz, 1 H), 7.93 (dd, J = 7.2 Hz, J = 8.0 Hz, 1 H), 8.21-8.24 (m, 1 H), 8.48 (t, J = 2.0 Hz, 1 H), 8.73 (t, J = 5.2 Hz, 1 H), 8.98 (d, J = 2.0 Hz, 1 H), 9.14 (d, J = 2.0 Hz, 1 H). | 1.94 Condition 37 517.2 |

| Ex. No. | Structure | Name | ¹H NMR | LC/MS Rt (min) Method M + H |
|---|---|---|---|---|
| 48 | 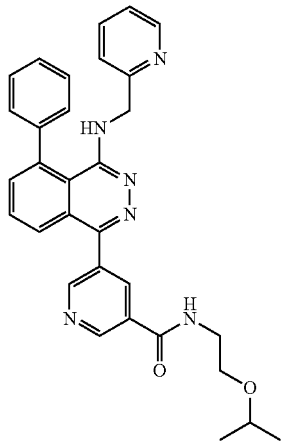 [SMILES: CC(C)OCCNC(=O)c1cncc(-c2nnc(NCc3ccccn3)c3c(-c4ccccc4)cccc23)c1] | N-(2-Isopropoxyethyl)-5-(5-phenyl-4-((pyridin-2-ylmethyl)amino)phthalazin-1-yl)nicotinamide | ¹H NMR (400 MHz, DMSO-$d_6$) δ 1.10 (d, J = 6.0 Hz, 6 H), 3.43-3.46 (m, 2 H), 3.51-3.52 (m, 2 H), 3.57 (sept, J = 6.0 Hz, 1 H), 4.65 (d, J = 4.4 Hz, 2 H), 6.32 (t, J = 4.4 Hz, 1 H), 7.22 (dd, J = 5.2 Hz, J = 6.8 Hz, 1 H), 7.27 (d, J = 8.0 Hz, 1 H), 7.50-7.58 (m, 5 H), 7.68-7.73 (m, 2 H), 7.84 (dd, J = 1.2 Hz, J = 8.0 Hz, 1 H), 7.92 (dd, J = 7.2 Hz, J = 8.0 Hz, 1 H), 8.21-8.24 (m, 1 H), 8.49 (t, J = 2.0 Hz, 1 H), 8.85 (t, J = 5.6 Hz, 1 H), 8.99 (d, J = 2.0 Hz, 1 H), 9.15 (d, J = 2.0 Hz, 1 H). | 1.62 Condition 37 519.2 |
| 49 | 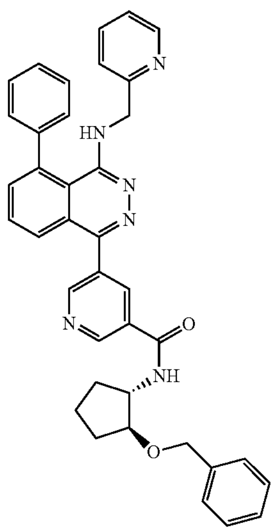 [SMILES: O=C(N[C@H]1CCC[C@@H]1OCc1ccccc1)c1cncc(-c2nnc(NCc3ccccn3)c3c(-c4ccccc4)cccc23)c1] | N-((1S,2S)-2-(Benzyloxy)cyclopentyl)-5-(5-phenyl-4-((pyridin-2-ylmethyl(amino)phthalazin-1-yl)nicotinamide | ¹H NMR (400 MHz, DMSO-$d_6$) δ 1.68-1.76 (m, 4 H), 1.88-1.95 (m, 1 H), 2.05-2.08 (m, 1 H), 3.92-3.96 (m, 1 H), 4.33-4.37 (m, 1 H), 4.55 (d, J = 8.0 Hz, 1 H), 4.60 (d, J = 8.0 Hz, 1 H), 4.66 (d, J = 4.4 Hz, 2 H), 6.32 (t, J = 4.4 Hz, 1 H), 7.20-7.32 (m, 7 H), 7.50-7.59 (m, 5 H), 7.68-7.73 (m, 2 H), 7.83 (dd, J = 1.2 Hz, J = 8.0 Hz, 1 H), 7.92 (dd, J = 7.2 Hz, J = 8.4 Hz, 1 H), 8.21-8.24 (m, 1 H), 8.49 (t, J = 2.0 Hz, 1 H), 8.67 (d, J = 7.6 Hz, 1 H), 8.99 (d, J = 2.0 Hz, 1 H), 9.16 (d, J = 2.0 Hz, 1 H). | 2.02 Condition 37 607.2 |
| 50 | 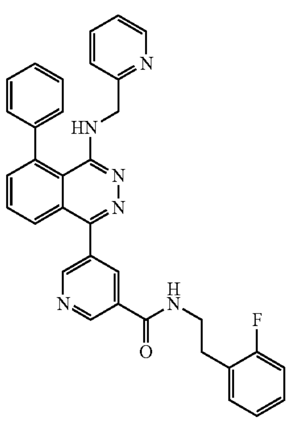 [SMILES: O=C(NCCc1ccccc1F)c1cncc(-c2nnc(NCc3ccccn3)c3c(-c4ccccc4)cccc23)c1] | N-(2-Fluorophenethyl)-5-(5-phenyl-4-((pyridin-2-ylmethyl)amino)phthalazin-1-yl)nicotinamide | ¹H NMR (400 MHz, DMSO-$d_6$) δ 2.93 (d, J = 6.8 Hz, 2 H), 3.55 (dd, J = 6.4 Hz, J = 6.8 Hz, 2 H), 4.66 (d, J = 4.0 Hz, 2 H), 6.32 (t, J = 4.0 Hz, 1 H), 7.14-7.34 (m, 6 H), 7.50-7.59 (m, 5 H), 7.68-7.73 (m, 2 H), 7.83 (dd, J = 1.6 Hz, J = 8.0 Hz, 1 H), 7.93 (dd, J = 7.2 Hz, J = 8.0 Hz, 1 H), 8.21-8.24 (m, 1 H), 8.45 (dd, J = 2.0 Hz, J = 2.4 Hz, 1 H), 8.93 (t, J = 6.4 Hz, 1 H), 8.99 (d, J = 2.4 Hz, 1 H), 9.11 (d, J = 2.0 Hz, 1 H). | 1.86 Condition 37 550.0 |

Utility

In general, compounds of the present invention, such as particular compounds disclosed in the preceding examples, have been shown to inhibit the $K_v1$ subfamily of voltage-gated $K^+$ channels (for example, by displaying % inhibition values ≥14%, preferably ≥30%, more preferably ≥40%, even more preferably ≥50%, at 0.3 micromolar concentration in an assay such as those set forth below). By displaying activity as inhibitors of the $K_v1$ subfamily of voltage-gated $K^+$ channels, compounds of the present invention are expected to be useful in the treatment of human diseases associated with the $K_v1$ subfamily of voltage-gated $K^+$ channels.

Assays to determine the degree of activity of a compound as an $I_{Kur}$ inhibitor are well known in the art and are described in references such as *J. Gen. Physiol.*, 101(4):513-543 (April 1993), and *Br. J. Pharmacol.*, 115(2):267-274 (May 1995).

Assays to determine the degree of activity of a compound as an inhibitor of other members of the $K_v1$ subfamily are also well known in the art. For example, inhibition of $K_v1.1$, $K_v1.2$ and $K_v1.3$ can be measured using procedures described by Grissmer, S. et al., *Mol. Pharmacol.*, 45(6):1227-1234 (June 1994); inhibition of $K_v1.4$ can be measured using procedures described by Petersen, K. R. et al., *Pflugers Arch.*, 437(3): 381-392 (February 1999); inhibition of $K_v1.6$ can be measured using procedures described by Bowlby, M. R. et al., *J. Neurophysiol.* 73(6):2221-2229 (June 1995); and inhibition of $K_v1.7$ can be measured using procedures described by Kalman, K. et al., *J. Biol. Chem.*, 273(10):5851-5857 (Mar. 6, 1998).

Examples 1-50, as shown in Table 2, were assayed for block of $I_{Kur}$ current in patch clamped mammalian L-929 cells which were injected with human $K_v$ 1.5 mRNA and stably expressed $I_{Kur}$ protein (as described in the references described below). Inhibition data at 0.3 mM concentration for the Examples are shown in Table 2.

1. Synders, D. J.; et al., "A rapidly activating and slowly inactivating potassium channel cloned from human heart: functional analysis after stable mammalian cell culture expression", *J. Gen. Physiol.*, 101:513-543 (1993).

2. Zhou, Z. et al., "Block of HERG potassium channels by the antihistamine astemizole and its metabolites desmethylastemizole and norastemizole", *J. Cardiovasc. Electrophysiol.*, 10(6):836-843 (1999).

TABLE 2

| Example | KV1_5% Inh L929 @0.3 µM |
|---------|-------------------------|
| 1  | 79.54 |
| 2  | 83.91 |
| 3  | 77.31 |
| 4  | 95.43 |
| 5  | 76.05 |
| 6  | 38.28 |
| 7  | 15.97 |
| 8  | 90.47 |
| 9  | 87.07 |
| 10 | 51.09 |
| 11 | 78.75 |
| 12 | 91.58 |
| 13 | 43.04 |
| 14 | 70.96 |
| 19 | 72.53 |
| 20 | 92.79 |
| 21 | 97.87 |
| 22 | 91.54 |
| 23 | 83.5  |
| 24 | 96.52 |
| 25 | 80.15 |
| 26 | 93.11 |
| 27 | 77.97 |
| 28 | 41.49 |
| 29 | 68.07 |
| 30 | 92.48 |
| 31 | 87.44 |
| 32 | 53.19 |
| 33 | 71.14 |
| 34 | 84    |
| 35 | 86.26 |
| 36 | 91.1  |
| 37 | 78.56 |
| 38 | 94.93 |

TABLE 2-continued

| Example | KV1_5% Inh L929 @0.3 µM |
|---------|-------------------------|
| 39 | 78.37 |
| 40 | 90.25 |
| 41 | 93.55 |
| 42 | 91.25 |
| 43 | 86.78 |
| 44 | 96.45 |
| 45 | 75.61 |
| 46 | 51.14 |
| 47 | 96.4  |
| 48 | 71.12 |
| 49 | 93.86 |
| 50 | 98.56 |

Example 16 is a prodrug of Example 1. Pro-drug cleavage to the respective parent compound was demonstrated in in vivo rat PK evaluation and at all doses administered PO. Additionally, pro-drugs evaluated in rat to determine the effect of pH modulators on PO PK utilizing Pentagastrin or Famotidine pre-treatment demonstrated that the pro-drug mitigated the pH dependent absorption in this model. Therefore, Example 16 is useful in the inhibition of potassium channel function and is useful in the treatment and prevention of arrhythmia, $I_{Kur}$-associated disorders, and other disorders mediated by ion channel function, by providing Example 1 which has been shown to be an inhibitor of potassium channel function.

Compounds within the scope of the present invention inhibit the $K_v1$ subfamily of voltage-gated $K^+$ channels, and as such are believed to be useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents, including maintaining normal sinus rhythm; angina pectoris including relief of Prinzmetal's symptoms, vasospastic symptoms and variant symptoms; gastrointestinal disorders including reflux esophagitis, functional dyspepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are believed to be useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are suspected antiarrhythmic agents which are useful in the prevention and treatment (including partial alleviation or cure) of arrhythmias. As inhibitors of $K_v1.5$, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esophagitis, functional dyspepsia, constipation, asthma, and diabetes. Additionally, $K_v1.5$ is known to be expressed in the anterior pituitary. Thus, administration of an $I_{Kur}$ blocker can stimulate growth hormone secretion. $I_{Kur}$ inhibitors can additionally be useful in cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula (I), (Ia), or compounds exemplified in the examples. Other therapeutic agents such as those described below may be employed with the inventive compounds in the present methods.

In the methods of the present invention, such other therapeutic agent(s) may be administered prior to, simultaneously with or following the administration of the compound(s) of the present invention.

Dosage and Formulation

The present invention also provides pharmaceutical compositions comprising at least one of the compounds of the formula (I), (Ia), or compounds exemplified in the examples, or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula (I), (Ia), or compounds exemplified in the examples, may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula (I), (Ia), or compounds exemplified in the examples, are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I), (Ia), or compounds exemplified in the examples, may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, CELEBREX®, VIOXX® and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thrombin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., QUESTRAN®); antiproliferative agents such as cyclosporin A, TAXOL®, FK 506, and adriamycin; antitumor agents such as TAXOL®, adriamycin, epothilones, cisplatin and carboplatin; anti-diabetic agents such as biguanides (e.g., metformin), glucosidase inhibitors (e.g., acarbose), insulins, meglitinides (e.g., repaglinide), sulfonylureas (e.g., glimepiride, glyburide and glipizide), biguanide/glyburide combinations (i.e., GLUCO-VANCE®), thiozolidinediones (e.g., troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g., cilostazol), and PDE V inhibitors (e.g., sildenafil); protein tyrosine kinase inhibitors; steroidal anti-inflammatory agents such as prednisone, and dexamethasone; and other anti-inflammatory agents such as ENBREL®. The combinations can be co-formulated or in the form of kits packaged to provide appropriate dosages for co-administration.

The above other therapeutic agents, when employed in combination with the compounds of the present invention, may be used, for example, in those amounts indicated in the *Physicians' Desk Reference* (PDR) or as otherwise determined by one of ordinary skill in the art.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon particular embodiments, it will be obvious to those of ordinary skill in the art that variations in the particular compounds and methods may be used and that it is intended that the invention may be practiced otherwise than as specifically described herein. Accordingly, this invention includes all modifications encompassed within the spirit and scope of the invention as defined by the claims that follow.

What is claimed is:
1. A compound of formula I

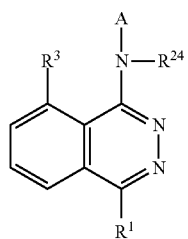

or an enantiomer, diastereomer, tautomer, or salt thereof wherein:

A is —$(CH_2)_m$—$R^2$, —$CH(R^{26})$—$R^2$, —$(CH_2)_{n-1}$—O—$R^2$, —$(CH_2)_{n-1}$—$NR^{25}$—$R^2$, —$CH(R^{26})$—$CO_2$—$R^2$, or —$(CH_2)_{n-1}$—$NR^{25}$—$CO_2$—$R^2$;

$R^1$ is $C_{1-10}$ alkyl substituted with 1-2 —OH, halo$C_{1-10}$ alkyl, $C_{2-12}$ alkenyl, $C_{3-10}$ cycloalkyl, wherein the cycloalkyl may be substituted with 0-2 $R^{13}$; or $R^1$ is

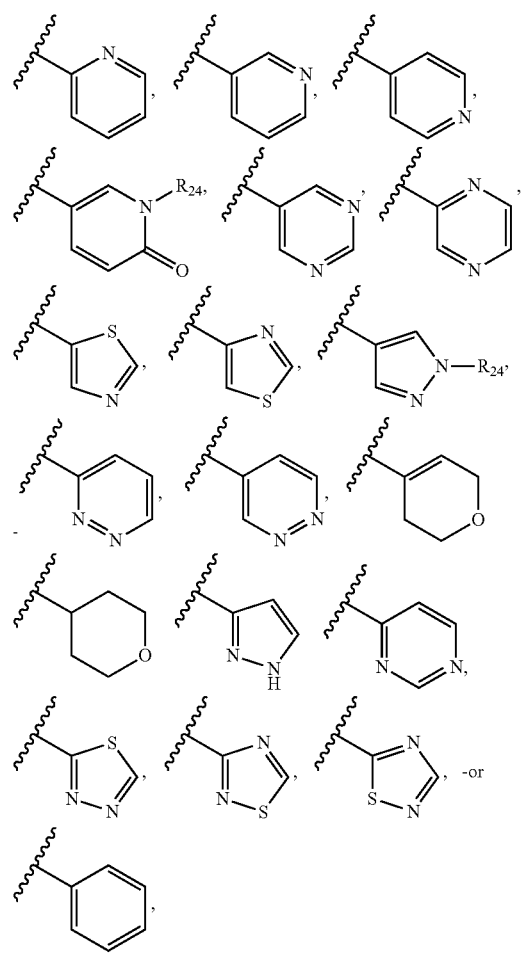

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyrans, or thiazolyl, any of which are substituted with 0-2 $R^{2a}$;

$R^{2a}$, at each occurrence, is independently H, —OH, F, Cl, Br, I, $C_{1-10}$alkyl, $C_{1-10}$alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R^{14}$, —$NR^{14}SO_2R^{14}$, =O, —$CONR^{14}R^{14}$, —$(CH_2)_m$—$SO_2NR^{14}R^{14}$, —$(CH_2)_m$—$NR^{14}SO_2R^{14}$, —$(CH_2)_n$—$NR^{14}SO_2NR^{14}R^{14}$, —$NR^{14}SO_2NR^{14}R^1_4$, —$CO_2NR^{14}R^{14}$, —$NR^{14}CO_2NR^{14}R^{14}$, —$NR^{14}COR^{14}$, —$SO_2NR^{14}COR^{14}$, —$SO_2NR^{14}CONR^{14}R^{14}$, —$NR^{14}CO_2R^{14}$, —$CO_2R^{14}$, —$NR^{14}R^{14}$, $NR^{14}CONR^{14}R^{14}$, —$C(=NOR^{14})NR^{14}R^{14}$, —$CONR^{14}OR^{14}$ or —$NCOR^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, or dihydropyran, tetrahydropyran any of which may be substituted with 0-1 $R^{3a}$;

$R^{3a}$ is halo, CN, $NH_2$, —O—$C_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R^{14}$, —$NR^{14}SO_2R^{14}$, =O, —$CONR^{14}R^{14}$, —$(CH_2)_m$—$SO_2NR^{14}R^{14}$, —$(CH_2)_m$—$NR^{14}SO_2R^{14}$, —$(CH_2)_n$—$NR^{14}SO_2NR^{14}R^{14}$, —$NR^{14}SO_2NR^{14}R^{14}$, —$CO_2NR^{14}R^{14}$, —$NR^{14}CO_2NR^{14}R^{14}$, —$NR^{14}COR^{14}$, —$SO_2NR^{14}COR^{14}$, —$SO_2NR^{14}CONR^{14}R^{14}$, —$NR^{14}CO_2R^{14}$, —$CO_2R^{14}$, —$NR^{14}R^{14}$, $NR^{14}CONR^{14}R^{14}$, —C(=$NOR^{14}$)$NR^{14}R^{14}$, —$CONR^{14}OR^{14}$ or —$NCOR^{14}$, $OR^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$ aryl, $C_{3-10}$cycloalkyl, a 4- to 12-membered heteroaryl, a 4- to 12-membered heterocyclyl, F, Cl, Br, I, —CN, —$NO_2$, —$CO_2R_{26}$, —$CO_2NR_{24}R_{24}$, —$OCF_3$, —$OR_{25}$, =O, —$CONR^{24}R^{24}$, —$COR^{24}$, —$SO_2R^{24}$, —$NR^{24}R^{24}$, —$NR^{24}CO_2R^{24}$, —$SO_2NR^{24}R^{24}$, or $C_{6-10}$aryl$C_{1-10}$ alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl; or $R^{25}$, at each occurrence, is independently selected from hydrogen, $C_{1-10}$alkyl, $C_{3-6}$cycloalkyl, or phenyl;

$R_{26}$, at each occurrence, is independently selected from hydrogen, $C_{1-10}$alkyl, $C_{3-6}$cycloalkyl, or phenyl;

m is 0 to 4;

n is 0 to 4; or n–1 is 2 to 4.

2. The compound of claim 1, wherein:

one of $R^1$ or $R^{1a}$ is $C_{1-10}$ alkyl substituted with 1-2 —OH, halo$C_{1-10}$ alkyl, $C_{3-10}$ cycloalkyl, wherein the cycloalkyl may be substituted with 0-2 $R^{13}$; or

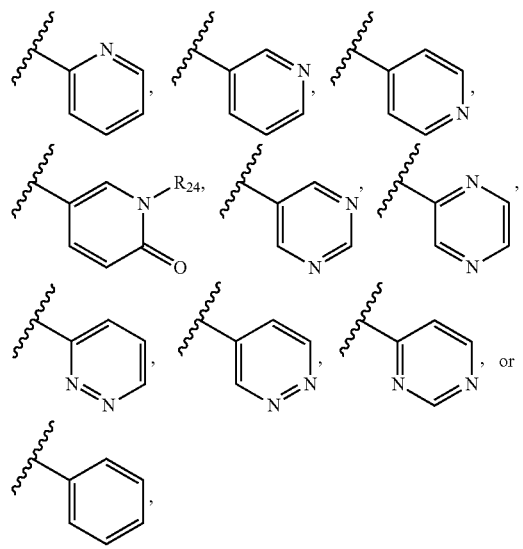

any of which may be substituted with 0-2 $R^{13}$.

3. The compound, of claim 2, wherein:

$R^{13}$, at each occurrence, is independently H, —OH, F, Cl, Br, I, $C_{1-6}$alkyl, $C_{1-6}$ alkoxy, halo$C_{1-6}$ alkyl, $C_{3-6}$cycloalkyl, phenyl, a 4- to 12-membered heteroaryl, wherein the heteroaryl is selected from tetrazolyl, —CN, —$NO_2$, —$(CH_2)_m$—$SO_2R^{14}$, —$NR^{14}SO_2R^{14}$, —$CONR^{14}R^{14}$, —$(CH_2)_m$—$SO_2NR^{14}R^{14}$, —$NR^{14}CO_2NR^{14}R^{14}$, —$NR^{14}CO_2NR^{14b}R^{14b}$, —$NR^{14}COR^{14}$, —$NR^{14}CO_2R^{14}$, —$CO_2R^{14}$, or —$NR^{14}R^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$ cycloalkyl, phenyl, wherein the alkyl, cycloalkyl, and phenyl, may be substituted with 0-3 $R^{14a}$; or alternatively, two $R^{14b}$'s are taken together with the atoms to which they are attached to form a cyclic ring, wherein the cyclic ring is morpholinyl, piperidinyl, or piperazinyl, and may be substituted with 0-1 $C_{1-6}$alkyl;

$R^{14a}$, at each occurrence, is independently selected from F, Cl, Br, I, $C_{1-6}$ alkyl, halo$C_{1-6}$alkyl, phenyl, $C_{3-6}$cycloalkyl.

4. The compound of claim 3, wherein:

A is —$(CH_2)_m$—$R^2$, —$CH(R^{26})$—$R_2$, —$(CH_2)_{n-1}$—O—$R_2$, —$(CH_2)_{n-1}$—$NR^{25}$—$R_2$, —$CH(R^{26})$—$CO_2$—$R^2$, or —$(CH_2)_{n-1}$—$NR^{25}$—$CO_2$—$R^2$;

$R^2$ is phenyl, pyridinyl, pyrazinyl, pyrimidinyl, piperidinyl, or pyridinone, any of which are substituted with 0-2 $R^{2a}$; or $R^{2a}$, at each occurrence, is independently H, —OH, F, $C_{1-6}$ alkyl, $C_{1-6}$ alkoxy, 6-$SO_2NR^{14}R^{14}$.

5. The compound of claim 4, wherein:

$R^1$ is $C_{1-10}$ alkyl substituted with 1-2 —OH, halo$C_{1-10}$ alkyl, $C_{3-10}$ cycloalkyl, wherein the cycloalkyl may be substituted with 0-1 $R^{13}$; or

101

$R^1$ is

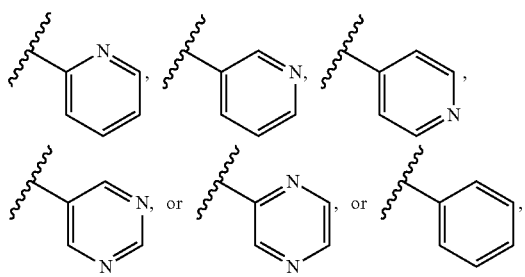

any of which may be substituted with 0-2 $R^{13}$.

6. The compound of claim 5, wherein:
$R^{13}$, at each occurrence, is independently H, $C_{1-6}$ alkyl, a 4- to 12-membered heteroaryl, wherein the heteroaryl is selected from tetrazolyl, —CN, —$NR^{14}SO_2R^{14}$, —$CONR^{14}R^{14}$, —$SO_2NR^{14}R^{14}$, —$NR^{14}CO_2NR^{14}R^{14}$, —$NR^{14}CO_2NR^{14b}R^{14b}$, —$NR^{14}COR^{14}$. —$CO_2R^{14}$, or —$NR^{14}R^{14}$, wherein the alkyl, and heteroaryl may be substituted with 0-2 $R^{14a}$;
$R^{14}$, at each occurrence, is independently selected from hydrogen, $C_{1-6}$ alkyl, $C_{3-6}$ cycloalkyl, phenyl, wherein the alkyl, cycloalkyl, and phenyl, may be substituted with 0-3 $R^{14a}$; or
two $R^{14b}$'s are taken together with the atoms to which they are attached to form a cyclic ring, wherein the cyclic ring is morpholinyl, and may be substituted with 0-1 $C_{1-6}$ alkyl;
$R^{14a}$, at each occurrence, is independently selected from F, Cl, Br, I, $C_{1-6}$ alkyl, halo$C_{1-6}$alkyl, phenyl, $C_{3-6}$ cycloalkyl.

7. The compound of claim 6, wherein:
A is —($CH_2$)—$R^2$;
$R^2$ is phenyl,

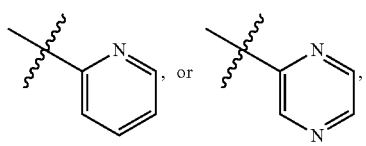 [SMILES: *c1ccccn1 ; *c1cnccn1]

any of which are substituted with 0-1 $R^{2a}$; or
$R^{2a}$, at each occurrence, is independently H, —OH, F, $C_{1-6}$alkyl, $C_{1-6}$alkoxy, $C_{1-6}$haloalkoxy, or $SO_2NR^{14}R^{14}$.

8. The compound of claim 7, wherein:
$R^3$ is phenyl.

9. The compound of claim 8, wherein:
$R^{24}$, at each occurrence, is independently selected from hydrogen, $C_{1-6}$alkyl, $C_{3-6}$cycloalkyl, or phenyl; or

102

$R^{25}$, at each occurrence, is independently selected from hydrogen, $C_{1-6}$alkyl, $C_{3-6}$cycloalkyl, or phenyl; or
$R_{26}$, at each occurrence, is independently selected from hydrogen, $C_{1-6}$alkyl, $C_{3-6}$cycloalkyl, or phenyl.

10. The compound of claim 9, wherein:
$R^{13}$, at each occurrence, is independently H, —CN, —$NHSO_2R^{14}$, —$CONH_2$, —$SO_2NR^{14}R^{14}$, —$NHCO_2NR^{14b}R^{14b}$, —$NHCOR^{14}$, or —$NH_2$;
$R^{14}$, at each occurrence, is independently selected from hydrogen, or methyl.

11. A compound, enantiomer, diastereomer, or salt thereof, selected from:

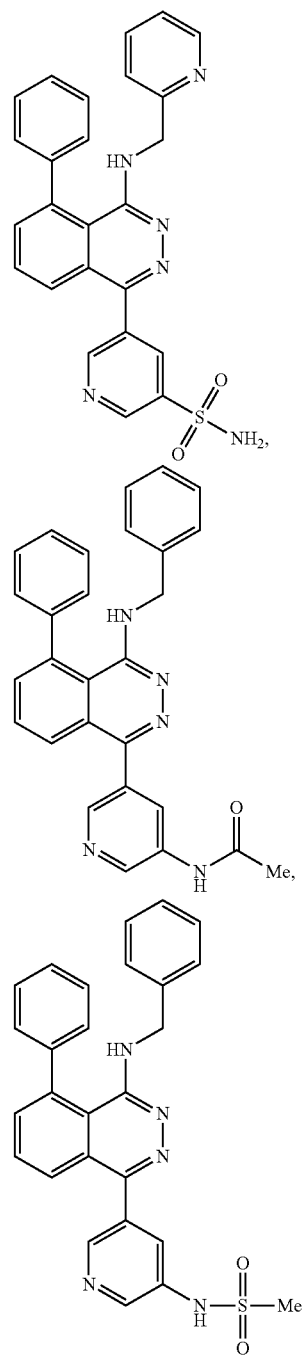

103

104

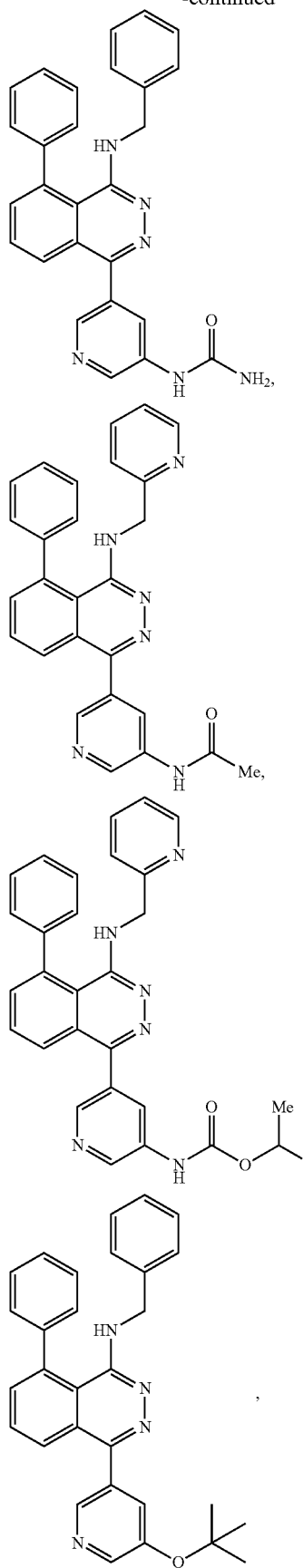
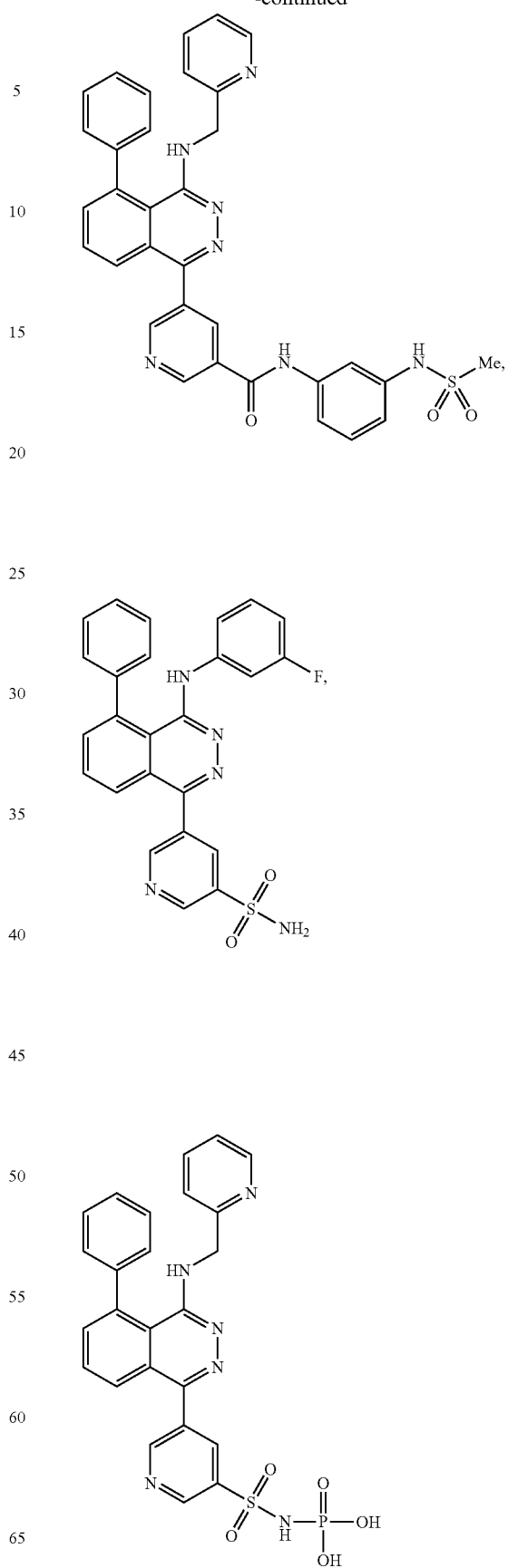

107
-continued
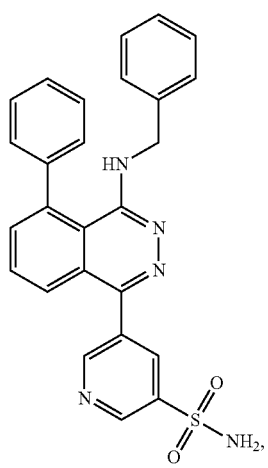
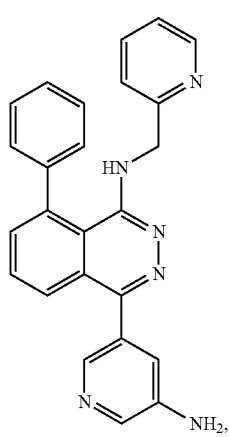
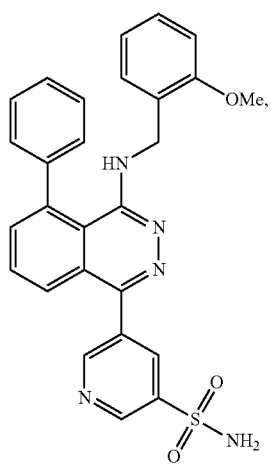
108
-continued
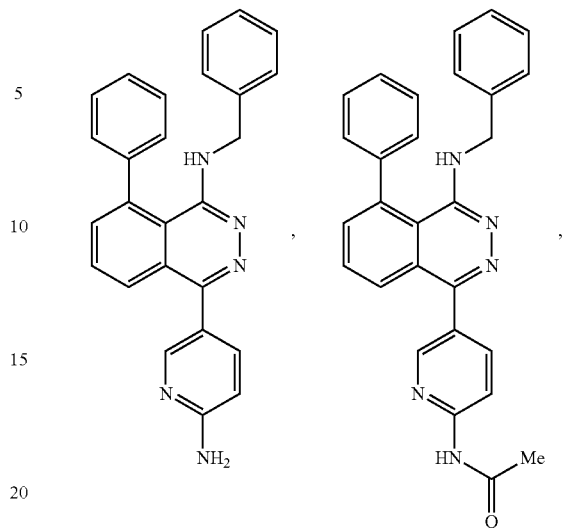
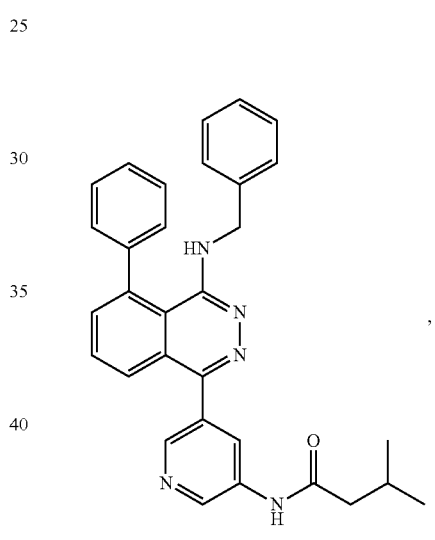
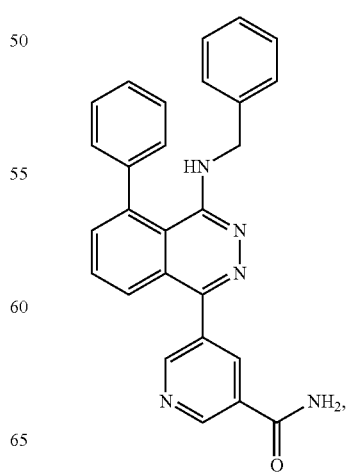

109
-continued
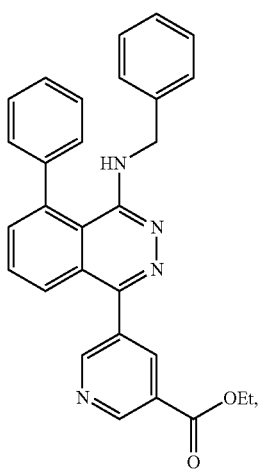
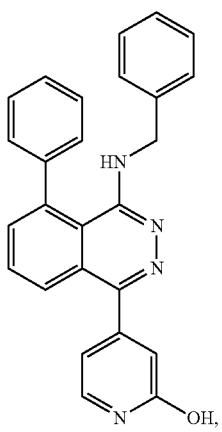
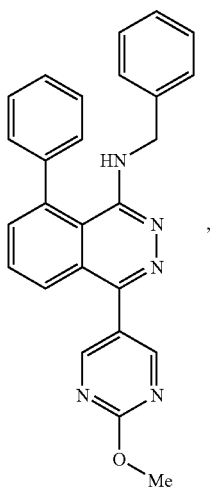
110
-continued
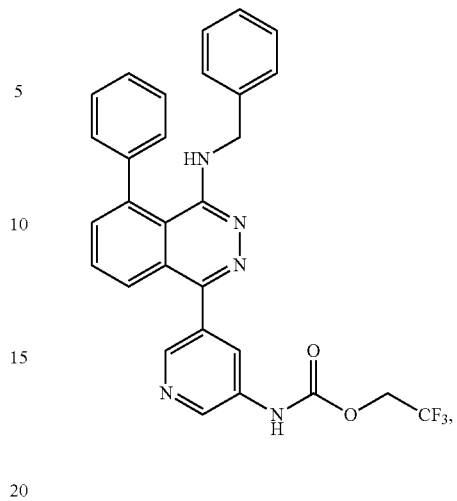
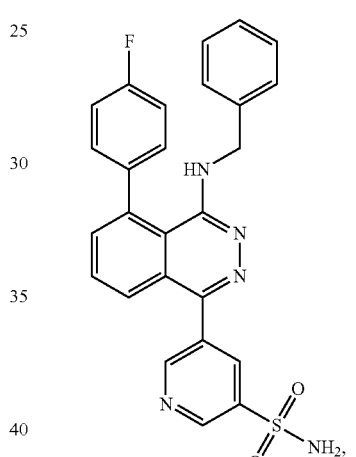
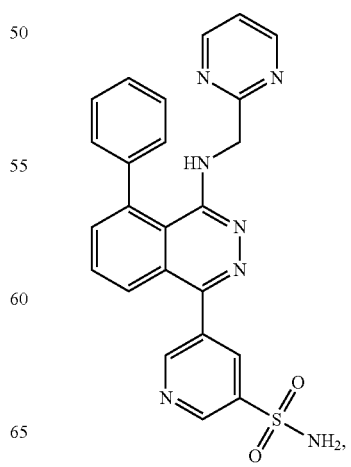

111
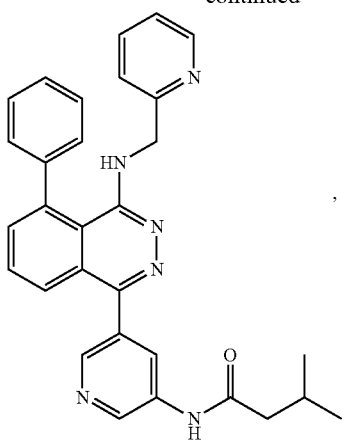
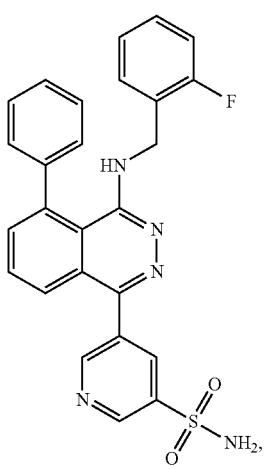
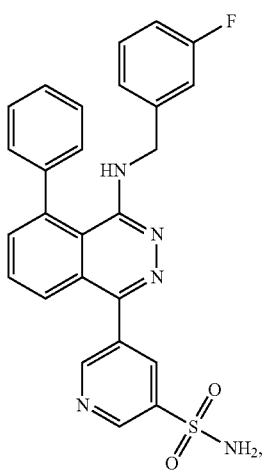
112
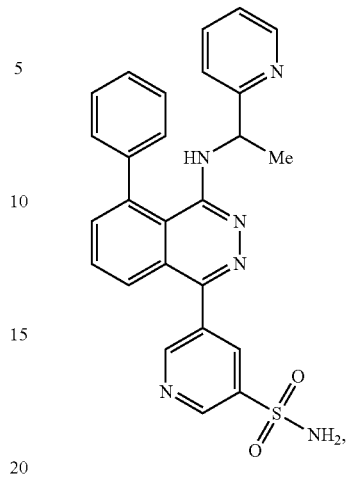
Enantiomer-1
Enantiomer-2
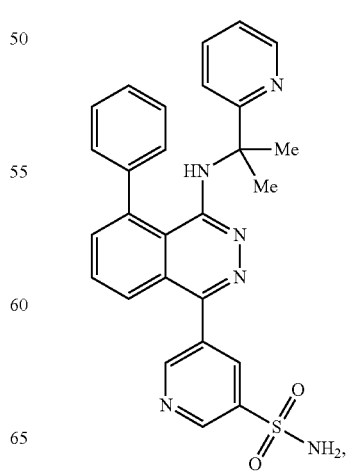

113
-continued
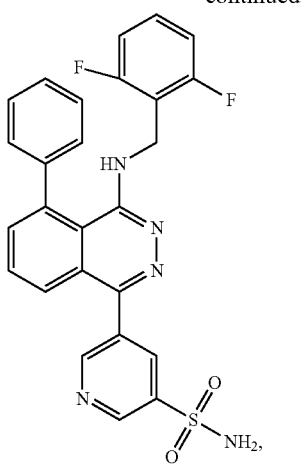
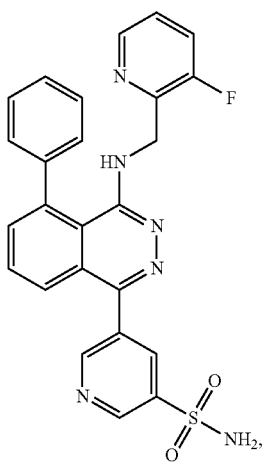
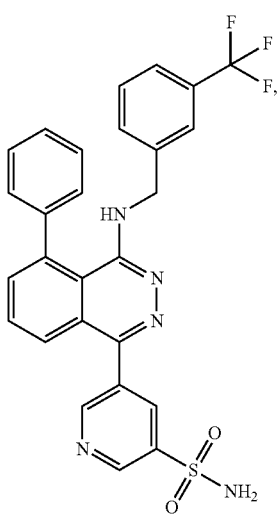
114
-continued
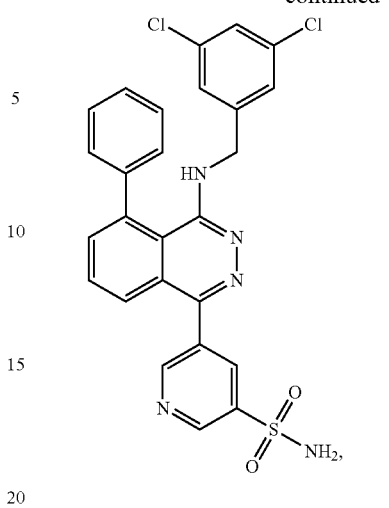
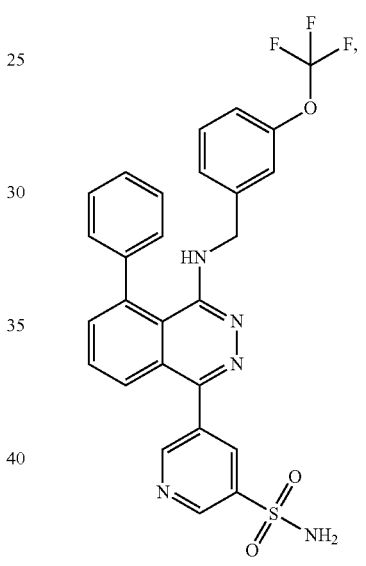
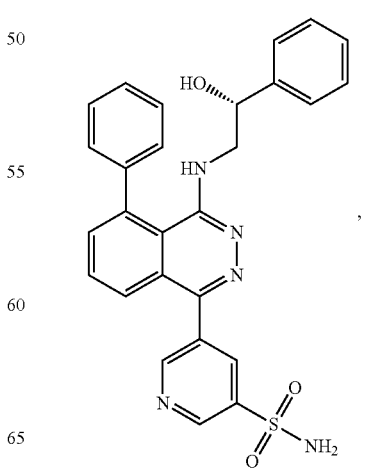

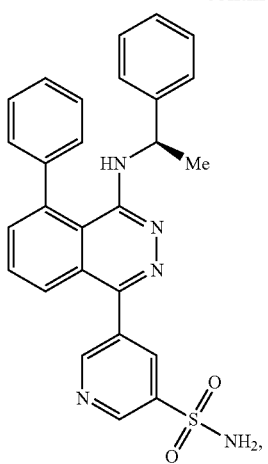
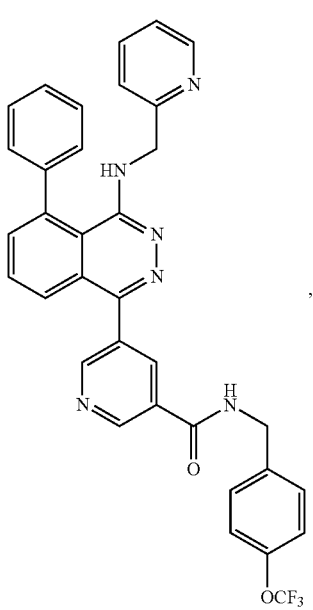
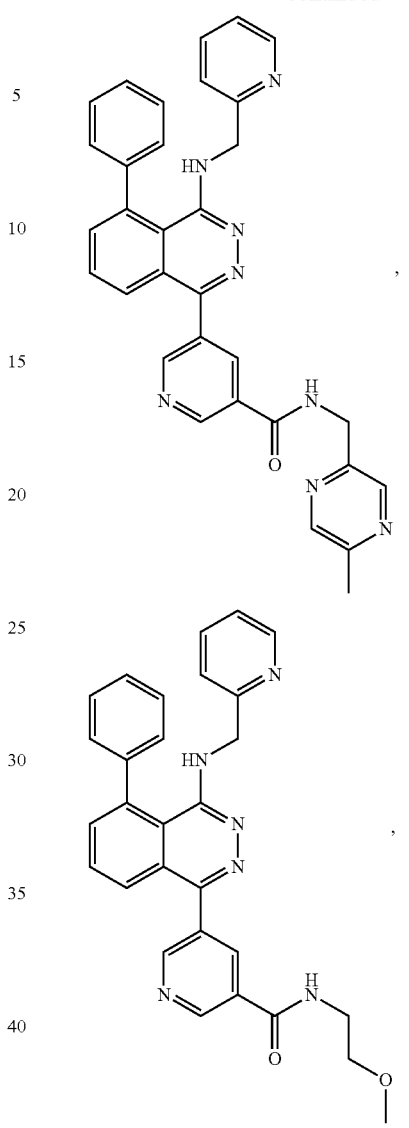

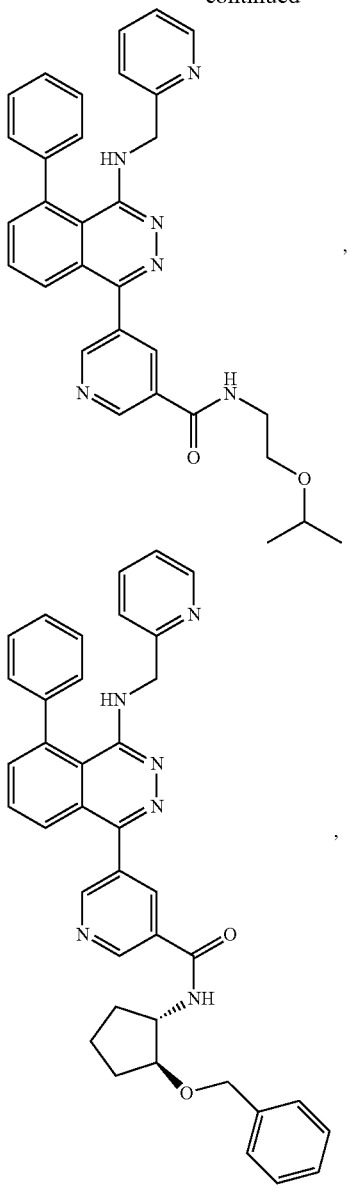

,   or

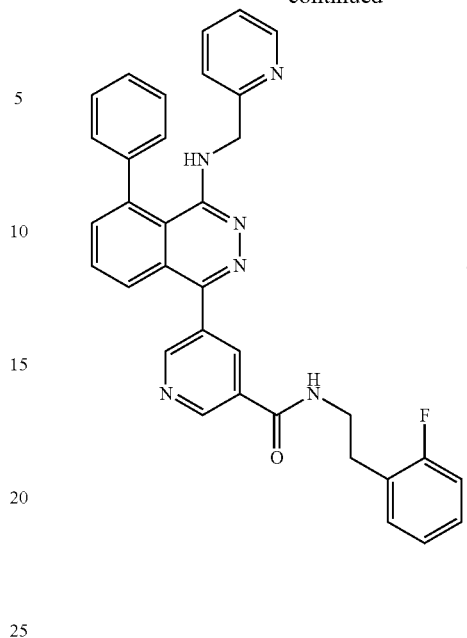

.

12. A pharmaceutical composition comprising a therapeutically effective amount of at least one compound of claim 1.

13. A pharmaceutical composition comprising a therapeutically effective amount of one or more compound of claim 11.

14. A method of treating arrhythmia comprising administering to a patient in need thereof an effective amount of at least one compound of claim 1.

15. A method of controlling heart rate comprising administering to a patient in need thereof an effective amount of at least one compound of claim 1.

16. A method of treating arrhythmia comprising administering to a patient in need thereof an effective amount of one or more compound of claim 11.

17. A method of controlling heart rate comprising administering to a patient in need thereof an effective amount of one or more compound of claim 11.

\* \* \* \* \*

UNITED STATES PATENT AND TRADEMARK OFFICE
CERTIFICATE OF CORRECTION

PATENT NO. : 9,242,966 B2  
APPLICATION NO. : 14/200063  
DATED : January 26, 2016  
INVENTOR(S) : Finlay et al.

Page 1 of 1

It is certified that error appears in the above-identified patent and that said Letters Patent is hereby corrected as shown below:

In the Claims

Claim 1, Column 98, Line 62, delete "$R^1{}_4$," and insert -- $R^{14}$, --, therefor.

Claim 1, Column 98, Line 66, delete "$NR^{14}$" and insert -- —$NR^{14}$ --, therefor.

Claim 1, Column 99, Line 23, delete "$NR^{14}$" and insert -- —$NR^{14}$ --, therefor.

Claim 3, Column 100, Line 26, delete "compound," and insert -- compound --, therefor.

Claim 5, Column 101, Lines 8-13, delete " 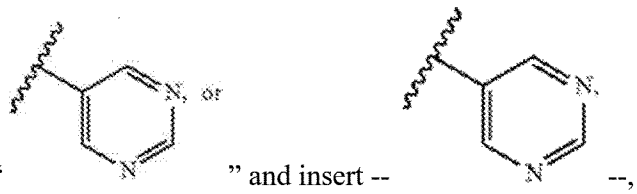 " and insert -- --, therefor.

Claim 6, Column 101, Line 26, delete "$COR^{14}$." and insert -- $COR^{14}$, --, therefor.

Signed and Sealed this  
Twenty-sixth Day of May, 2020

Andrei Iancu  
*Director of the United States Patent and Trademark Office*